(12) United States Patent  (10) Patent No.: US 9,028,549 B1
Wensel  (45) Date of Patent: May 12, 2015

(54) INTERVERTEBRAL FUSION DEVICE AND METHOD OF USE

(71) Applicant: Spinelogik, Inc., Eugene, OR (US)

(72) Inventor: Jeffrey Paris Wensel, Eugene, OR (US)

(73) Assignee: Spinelogik, Inc., Eugene, OR (US)

( * ) Notice: Subject to any disclaimer, the term of this patent is extended or adjusted under 35 U.S.C. 154(b) by 0 days.

(21) Appl. No.: 13/753,373

(22) Filed: Jan. 29, 2013

Related U.S. Application Data

(63) Continuation of application No. 12/383,950, filed on Mar. 27, 2009, now Pat. No. 8,382,839.

(60) Provisional application No. 61/148,036, filed on Jan. 28, 2009, provisional application No. 61/109,175, filed on Oct. 28, 2008, provisional application No. 61/040,136, filed on Mar. 27, 2008.

(51) Int. Cl.
*A61F 2/44* (2006.01)

(52) U.S. Cl.
CPC ........................ *A61F 2/447* (2013.01)

(58) Field of Classification Search
CPC ...................... A61F 2/44; A61F 2002/4475
USPC ................. 623/17.11, 17.15, 17.16
See application file for complete search history.

(56) References Cited

U.S. PATENT DOCUMENTS

| | | |
|---|---|---|
| 776,049 A | 11/1904 | Frühling |
| 4,554,914 A | 11/1985 | Kapp et al. |
| 4,904,260 A * | 2/1990 | Ray et al. ............ 623/17.12 |
| D312,309 S | 11/1990 | Michelson |
| 5,015,247 A | 5/1991 | Michelson |
| 5,314,477 A | 5/1994 | Marnay |
| 5,397,364 A | 3/1995 | Kozak et al. |
| 5,484,437 A | 1/1996 | Michelson |
| 5,505,732 A | 4/1996 | Michelson |
| 5,522,817 A | 6/1996 | Sander et al. |
| 5,522,899 A | 6/1996 | Michelson |
| D377,095 S | 12/1996 | Michelson |
| D377,096 S | 12/1996 | Michelson |
| D377,527 S | 1/1997 | Michelson |
| 5,593,409 A | 1/1997 | Michelson |

(Continued)

FOREIGN PATENT DOCUMENTS

| | | |
|---|---|---|
| DE | 19944681 | 3/2001 |
| RU | 2004218 | 12/1993 |

OTHER PUBLICATIONS

U.S. Appl. No. 12/705,978, filed Feb. 15, 2010, Wensel, Jeffrey Paris.

(Continued)

*Primary Examiner* — Thomas J Sweet
*Assistant Examiner* — Seema Mathew
(74) *Attorney, Agent, or Firm* — Adeli LLP

(57) ABSTRACT

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies, (2) a delivery mechanism that delivers and positions the fusion member between the vertebral bodies, and (3) an anchoring member that affixes the fusion member to the vertebral bodies.

20 Claims, 76 Drawing Sheets

(56) References Cited

U.S. PATENT DOCUMENTS

| | | | |
|---|---|---|---|
| 5,609,635 A * | 3/1997 | Michelson | 623/17.16 |
| 5,609,636 A * | 3/1997 | Kohrs et al. | 623/17.16 |
| 5,653,761 A * | 8/1997 | Pisharodi | 606/86 A |
| D392,387 S | 3/1998 | Michelson | |
| 5,741,253 A | 4/1998 | Michelson | |
| 5,766,254 A * | 6/1998 | Gelbard | 623/17.16 |
| 5,772,661 A | 6/1998 | Michelson | |
| 5,776,199 A | 7/1998 | Michelson | |
| 5,785,710 A | 7/1998 | Michelson | |
| 5,797,909 A | 8/1998 | Michelson | |
| 5,860,973 A | 1/1999 | Michelson | |
| D425,989 S | 5/2000 | Michelson | |
| 6,080,155 A | 6/2000 | Michelson | |
| 6,096,038 A | 8/2000 | Michelson | |
| 6,120,502 A | 9/2000 | Michelson | |
| 6,120,503 A | 9/2000 | Michelson | |
| 6,123,705 A | 9/2000 | Michelson | |
| 6,136,001 A | 10/2000 | Michelson | |
| 6,139,551 A * | 10/2000 | Michelson et al. | 606/79 |
| 6,149,650 A | 11/2000 | Michelson | |
| RE37,005 E | 12/2000 | Michelson et al. | |
| 6,159,215 A | 12/2000 | Urbahns et al. | |
| 6,190,388 B1 | 2/2001 | Michelson et al. | |
| 6,210,412 B1 | 4/2001 | Michelson | |
| RE37,161 E | 5/2001 | Michelson et al. | |
| 6,224,595 B1 | 5/2001 | Michelson | |
| 6,224,607 B1 | 5/2001 | Michelson | |
| 6,241,770 B1 | 6/2001 | Michelson | |
| 6,264,656 B1 | 7/2001 | Michelson | |
| 6,270,498 B1 | 8/2001 | Michelson | |
| 6,302,914 B1 | 10/2001 | Michelson | |
| 6,315,795 B1 | 11/2001 | Scarborough et al. | |
| 6,350,283 B1 | 2/2002 | Michelson | |
| 6,436,098 B1 | 8/2002 | Michelson | |
| 6,447,544 B1 | 9/2002 | Michelson | |
| 6,447,547 B1 | 9/2002 | Michelson | |
| 6,468,276 B1 | 10/2002 | McKay | |
| 6,478,823 B1 | 11/2002 | Michelson | |
| 6,485,517 B1 | 11/2002 | Michelson | |
| 6,500,205 B1 | 12/2002 | Michelson | |
| 6,537,320 B1 | 3/2003 | Michelson | |
| 6,554,836 B2 * | 4/2003 | Michelson | 606/86 R |
| 6,558,423 B1 * | 5/2003 | Michelson | 623/17.11 |
| 6,565,574 B2 | 5/2003 | Michelson | |
| 6,582,432 B1 | 6/2003 | Michelson | |
| 6,605,089 B1 | 8/2003 | Michelson | |
| 6,652,584 B2 | 11/2003 | Michelson | |
| 6,666,890 B2 | 12/2003 | Michelson | |
| 6,709,458 B2 | 3/2004 | Michelson | |
| 6,716,247 B2 | 4/2004 | Michelson | |
| 6,730,127 B2 | 5/2004 | Michelson | |
| 6,733,535 B2 | 5/2004 | Michelson | |
| 6,749,636 B2 | 6/2004 | Michelson | |
| 6,758,849 B1 | 7/2004 | Michelson | |
| 6,767,367 B1 * | 7/2004 | Michelson | 623/17.16 |
| 6,770,074 B2 | 8/2004 | Michelson | |
| 6,793,679 B2 | 9/2004 | Michelson | |
| 6,808,537 B2 | 10/2004 | Michelson | |
| 6,814,756 B1 | 11/2004 | Michelson | |
| 6,827,740 B1 | 12/2004 | Michelson | |
| 6,849,093 B2 | 2/2005 | Michelson | |
| 6,875,213 B2 | 4/2005 | Michelson | |
| 6,890,355 B2 | 5/2005 | Michelson | |
| 6,902,578 B1 | 6/2005 | Anderson et al. | |
| 6,923,810 B1 | 8/2005 | Michelson | |
| 6,923,830 B2 | 8/2005 | Michelson | |
| 6,946,000 B2 * | 9/2005 | Senegas et al. | 623/17.11 |
| 6,962,606 B2 | 11/2005 | Michelson | |
| 6,972,019 B2 | 12/2005 | Michelson | |
| 6,972,035 B2 | 12/2005 | Michelson | |
| 6,981,975 B2 | 1/2006 | Michelson | |
| 6,989,031 B2 | 1/2006 | Michelson | |
| 7,008,453 B1 | 3/2006 | Michelson | |
| 7,022,137 B2 | 4/2006 | Michelson | |
| 7,033,394 B2 | 4/2006 | Michelson | |
| 7,041,135 B2 | 5/2006 | Michelson | |
| 7,051,417 B2 | 5/2006 | Michelson | |
| 7,056,342 B2 | 6/2006 | Michelson | |
| 7,063,701 B2 | 6/2006 | Michelson | |
| 7,063,702 B2 | 6/2006 | Michelson | |
| 7,066,961 B2 | 6/2006 | Michelson | |
| 7,094,239 B1 | 8/2006 | Michelson | |
| 7,112,206 B2 | 9/2006 | Michelson | |
| 7,115,128 B2 | 10/2006 | Michelson | |
| 7,115,143 B1 | 10/2006 | Michelson | |
| 7,118,579 B2 | 10/2006 | Michelson | |
| 7,118,598 B2 | 10/2006 | Michelson | |
| 7,128,760 B2 | 10/2006 | Michelson | |
| 7,156,875 B2 | 1/2007 | Michelson | |
| 7,163,561 B2 | 1/2007 | Michelson | |
| 7,166,107 B2 | 1/2007 | Anderson | |
| 7,166,129 B2 | 1/2007 | Michelson | |
| 7,195,643 B2 | 3/2007 | Jackson | |
| 7,207,991 B2 | 4/2007 | Michelson | |
| 7,244,275 B2 | 7/2007 | Michelson | |
| 7,255,698 B2 | 8/2007 | Michelson | |
| 7,255,713 B2 | 8/2007 | Malek | |
| 7,264,622 B2 | 9/2007 | Michelson | |
| 7,288,093 B2 | 10/2007 | Michelson | |
| 7,291,149 B1 | 11/2007 | Michelson | |
| 7,320,686 B2 | 1/2008 | Serhan et al. | |
| 7,326,214 B2 | 2/2008 | Michelson | |
| 7,326,248 B2 | 2/2008 | Michelson | |
| 7,354,442 B2 * | 4/2008 | Sasso et al. | 606/280 |
| 7,387,643 B2 | 6/2008 | Michelson | |
| 7,396,365 B2 | 7/2008 | Michelson | |
| 7,399,303 B2 | 7/2008 | Michelson | |
| 7,410,501 B2 | 8/2008 | Michelson | |
| 7,431,722 B1 | 10/2008 | Michelson | |
| 7,435,262 B2 | 10/2008 | Michelson | |
| 7,442,209 B2 | 10/2008 | Michelson | |
| 7,445,636 B2 | 11/2008 | Michelson | |
| 7,452,359 B1 | 11/2008 | Michelson | |
| 7,455,672 B2 | 11/2008 | Michelson | |
| 7,455,692 B2 | 11/2008 | Michelson | |
| 7,462,195 B1 | 12/2008 | Michelson | |
| 7,491,205 B1 | 2/2009 | Michelson | |
| 7,497,859 B2 | 3/2009 | Zucherman et al. | |
| 7,503,933 B2 | 3/2009 | Michelson | |
| 7,534,254 B1 | 5/2009 | Michelson | |
| 7,540,882 B2 | 6/2009 | Michelson | |
| 7,569,054 B2 | 8/2009 | Michelson | |
| 7,608,107 B2 | 10/2009 | Michelson | |
| 7,611,536 B2 | 11/2009 | Michelson | |
| 7,618,423 B1 | 11/2009 | Valentine et al. | |
| 7,637,951 B2 | 12/2009 | Michelson | |
| 7,637,954 B2 | 12/2009 | Michelson | |
| 7,655,027 B2 | 2/2010 | Michelson | |
| 7,662,134 B2 | 2/2010 | Miller | |
| 7,662,184 B2 | 2/2010 | Edwards et al. | |
| 7,686,805 B2 | 3/2010 | Michelson | |
| 7,691,148 B2 | 4/2010 | Michelson | |
| 7,717,947 B1 * | 5/2010 | Wilberg et al. | 606/304 |
| 7,722,619 B2 | 5/2010 | Michelson | |
| 7,771,475 B2 | 8/2010 | Michelson | |
| 7,789,914 B2 | 9/2010 | Michelson | |
| 7,794,502 B2 | 9/2010 | Michelson | |
| 7,815,683 B2 | 10/2010 | Melkent et al. | |
| 7,828,800 B2 | 11/2010 | Michelson | |
| 7,833,271 B2 | 11/2010 | Mitchell et al. | |
| 7,887,565 B2 | 2/2011 | Michelson | |
| 7,892,286 B2 | 2/2011 | Michelson | |
| 7,914,530 B2 | 3/2011 | Michelson | |
| 7,914,554 B2 | 3/2011 | Michelson | |
| 7,922,729 B2 | 4/2011 | Michelson | |
| 7,931,840 B2 | 4/2011 | Michelson | |
| 7,935,116 B2 | 5/2011 | Michelson | |
| 7,935,149 B2 | 5/2011 | Michelson | |
| 7,942,933 B2 | 5/2011 | Michelson | |
| 7,959,675 B2 * | 6/2011 | Gately | 623/17.11 |
| 7,972,365 B2 | 7/2011 | Michelson | |
| 7,972,381 B2 | 7/2011 | Michelson | |
| 7,976,566 B2 | 7/2011 | Michelson | |
| 8,083,744 B2 | 12/2011 | Dorchak et al. | |

(56) References Cited

U.S. PATENT DOCUMENTS

| | | | |
|---|---|---|---|
| 8,167,915 B2* | 5/2012 | Ferree et al. ............... 606/279 |
| 8,182,532 B2* | 5/2012 | Anderson et al. ........... 623/17.11 |
| 8,182,539 B2* | 5/2012 | Tyber et al. ................ 623/17.16 |
| 8,206,449 B2 | 6/2012 | Jansen et al. |
| 8,231,676 B2* | 7/2012 | Trudeau et al. ............ 623/17.11 |
| 8,241,364 B2* | 8/2012 | Hansell et al. ............. 623/17.16 |
| 8,292,960 B2 | 10/2012 | Kleiner |
| 8,308,805 B2* | 11/2012 | Lynn et al. ................. 623/17.16 |
| 8,313,528 B1* | 11/2012 | Wensel ....................... 623/17.11 |
| 8,333,804 B1* | 12/2012 | Wensel ....................... 623/17.11 |
| 8,366,774 B1 | 2/2013 | Bruffey et al. |
| 8,372,126 B2 | 2/2013 | Trieu et al. |
| 8,382,808 B2* | 2/2013 | Wilberg et al. ............. 606/304 |
| 8,382,839 B1 | 2/2013 | Wensel |
| 8,454,623 B2* | 6/2013 | Patel et al. ................. 606/99 |
| 8,460,385 B1 | 6/2013 | Wensel |
| 8,523,945 B1 | 9/2013 | Wensel |
| 8,551,175 B1 | 10/2013 | Wensel |
| 2002/0099378 A1 | 7/2002 | Michelson |
| 2003/0187436 A1 | 10/2003 | Bolger et al. |
| 2003/0191371 A1 | 10/2003 | Smith et al. |
| 2004/0010316 A1* | 1/2004 | William et al. ............. 623/17.16 |
| 2005/0010294 A1 | 1/2005 | Michelson |
| 2005/0065519 A1 | 3/2005 | Michelson |
| 2005/0065607 A1 | 3/2005 | Gross |
| 2005/0070913 A1 | 3/2005 | Milbocker et al. |
| 2005/0137707 A1 | 6/2005 | Malek |
| 2005/0251257 A1 | 11/2005 | Mitchell et al. |
| 2005/0277930 A1 | 12/2005 | Parsons |
| 2005/0283246 A1 | 12/2005 | Cauthen, III et al. |
| 2006/0009850 A1 | 1/2006 | Frigg et al. |
| 2006/0036322 A1 | 2/2006 | Reiley |
| 2006/0058876 A1 | 3/2006 | McKinley |
| 2006/0079961 A1 | 4/2006 | Michelson |
| 2006/0089646 A1* | 4/2006 | Bonutti ....................... 606/61 |
| 2006/0106460 A1 | 5/2006 | Messerli et al. |
| 2006/0122623 A1 | 6/2006 | Truckai et al. |
| 2006/0206207 A1* | 9/2006 | Dryer et al. ................ 623/17.11 |
| 2006/0247600 A1 | 11/2006 | Yeung et al. |
| 2007/0038219 A1* | 2/2007 | Matthis et al. ............. 606/72 |
| 2007/0043441 A1 | 2/2007 | Pisharodi |
| 2007/0050030 A1 | 3/2007 | Kim |
| 2007/0055376 A1 | 3/2007 | Michelson |
| 2007/0219635 A1 | 9/2007 | Mathieu et al. |
| 2007/0225813 A1 | 9/2007 | Haines |
| 2007/0270858 A1* | 11/2007 | Trieu et al. ................. 606/73 |
| 2008/0015694 A1* | 1/2008 | Tribus ......................... 623/17.11 |
| 2008/0065215 A1 | 3/2008 | Reiley |
| 2008/0091200 A1* | 4/2008 | Kuiper et al. ............... 606/61 |
| 2008/0091205 A1 | 4/2008 | Kuiper et al. |
| 2008/0221695 A1* | 9/2008 | Jacofsky et al. ........... 623/17.16 |
| 2008/0269901 A1* | 10/2008 | Baynham et al. .......... 623/17.16 |
| 2008/0281428 A1 | 11/2008 | Meyers et al. |
| 2008/0319481 A1* | 12/2008 | Moore ......................... 606/246 |
| 2009/0138015 A1 | 5/2009 | Conner et al. |
| 2009/0149959 A1 | 6/2009 | Conner et al. |
| 2009/0164020 A1* | 6/2009 | Janowski et al. .......... 623/17.16 |
| 2009/0171389 A1* | 7/2009 | Sankaran ..................... 606/246 |
| 2009/0171461 A1* | 7/2009 | Conner et al. .............. 623/17.11 |
| 2009/0234392 A1* | 9/2009 | Dziedzic et al. ............ 606/279 |
| 2009/0265007 A1 | 10/2009 | Colleran |
| 2009/0292316 A1 | 11/2009 | Hess |
| 2010/0114317 A1* | 5/2010 | Lambrecht et al. ........ 623/17.11 |
| 2010/0160984 A1* | 6/2010 | Berry et al. ................. 606/86 A |
| 2010/0168861 A1 | 7/2010 | Yundt |
| 2010/0204796 A1* | 8/2010 | Bae et al. .................... 623/17.16 |
| 2010/0249935 A1* | 9/2010 | Slivka et al. ............... 623/17.16 |
| 2010/0263339 A1* | 10/2010 | Malinin et al. ............. 623/17.11 |
| 2010/0286777 A1 | 11/2010 | Errico et al. |
| 2011/0166660 A1 | 7/2011 | Laurence |
| 2011/0196494 A1* | 8/2011 | Yedlicka et al. ........... 623/17.16 |
| 2011/0208311 A1 | 8/2011 | Janowski |
| 2012/0078373 A1 | 3/2012 | Gamache et al. |
| 2012/0095561 A1 | 4/2012 | Voisard et al. |
| 2012/0191191 A1* | 7/2012 | Trieu .......................... 623/17.11 |
| 2012/0330426 A1 | 12/2012 | McLaughlin et al. |
| 2013/0030536 A1 | 1/2013 | Rhoda et al. |

OTHER PUBLICATIONS

U.S. Appl. No. 13/032,634, filed Feb. 22, 2011, Wensel, Jeffrey Paris.
U.S. Appl. No. 13/655,412, filed Oct. 18, 2012, Spinelogik, Inc.
U.S. Appl. No. 13/663,472, filed Oct. 30, 2012, Spinelogik, Inc.
U.S. Appl. No. 13/909,039, filed Jun. 3, 2013, Spinelogik, Inc.
Portions of prosecution history of U.S. Appl. No. 12/113,362, filed Oct. 17, 2012, Wensel, Jeffrey Paris.
Portions of prosecution history of U.S. Appl. No. 12/361,525, filed Nov. 14, 2012, Wensel, Jeffrey Paris.
Portions of prosecution history of U.S. Appl. No. 12/383,950, filed Jan. 22, 2013, Wensel, Jeffrey Paris.
Portions of prosecution history of U.S. Appl. No. 12/705,970, filed Aug. 5, 2013, Wensel, Jeffrey Paris.
Portions of prosecution history of U.S. Appl. No. 12/705,972, filed May 15, 2013, Wensel, Jeffrey Paris.
Portions of prosecution history of U.S. Appl. No. 12/705,974, filed Sep. 14, 2013, Wensel, Jeffrey Paris.
Portions of prosecution history of U.S. Appl. No. 12/705,978, filed Oct. 25, 2013, Wensel, Jeffrey Paris.
Portions of prosecution history of U.S. Appl. No. 13/032,634, filed Aug. 19, 2013, Wensel, Jeffrey Paris.
Portions of prosecution history of U.S. Appl. No. 13/655,412, filed Jan. 16, 2013, Spinelogik, Inc.
Portions of prosecution history of U.S. Appl. No. 13/663,472, filed Nov. 8, 2013, Spinelogik, Inc.
Updated portions of prosecution history of U.S. Appl. No. 13/663,472, filed Aug. 20, 2014, Wensel, Jeffrey Paris.
Portions of prosecution history of U.S. Appl. No. 13/909,039, filed Aug. 25, 2014, Wensel, Jeffrey Paris.
Updated portions of prosecution history of U.S. Appl. No. 12/705,978, filed Dec. 26, 2013, Wensel, Jeffrey Paris.
Updated portions of prosecution history of U.S. Appl. No. 13/032,634, filed Jan. 21, 2014, Wensel, Jeffrey Paris.
Updated portions of prosecution history of U.S. Appl. No. 13/663,472, filed Oct. 20, 2014, Spinelogik, Inc.
Updated portions of prosecution history of U.S. Appl. No. 13/655,412, filed Nov. 18, 2014, Spinelogik, Inc.
Updated portions of prosecution history of U.S. Appl. No. 13/909,039, filed Dec. 4, 2014, Spinelogik, Inc.
Updated portions of prosecution history of U.S. Appl. No. 13/032,634, filed Nov. 18, 2014, Wensel, Jeffrey Paris.

* cited by examiner

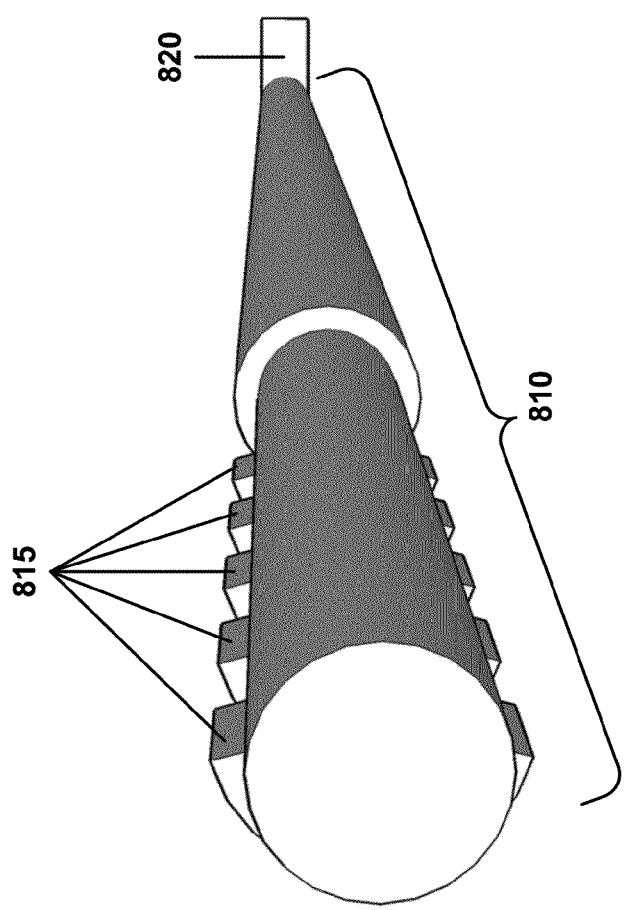

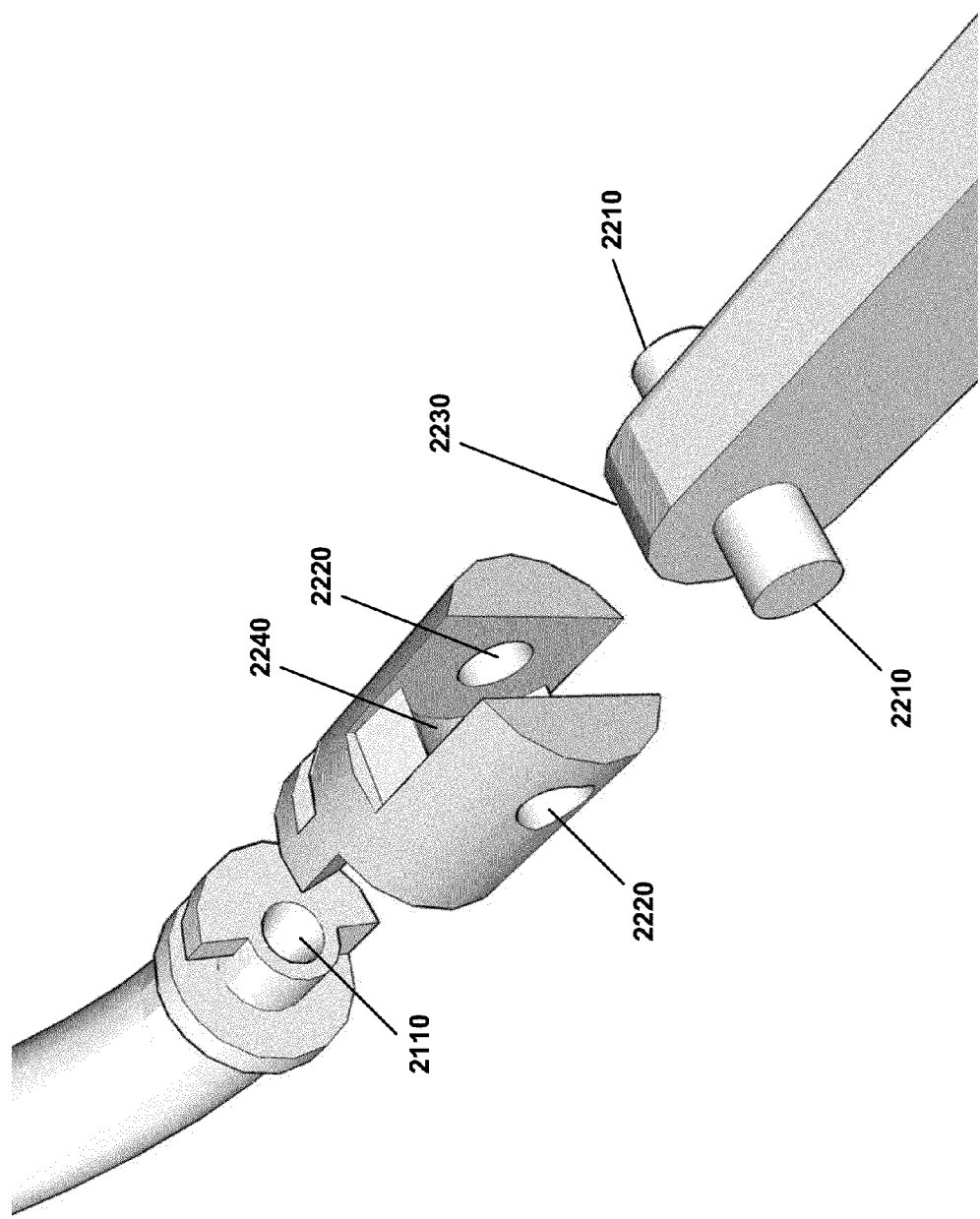

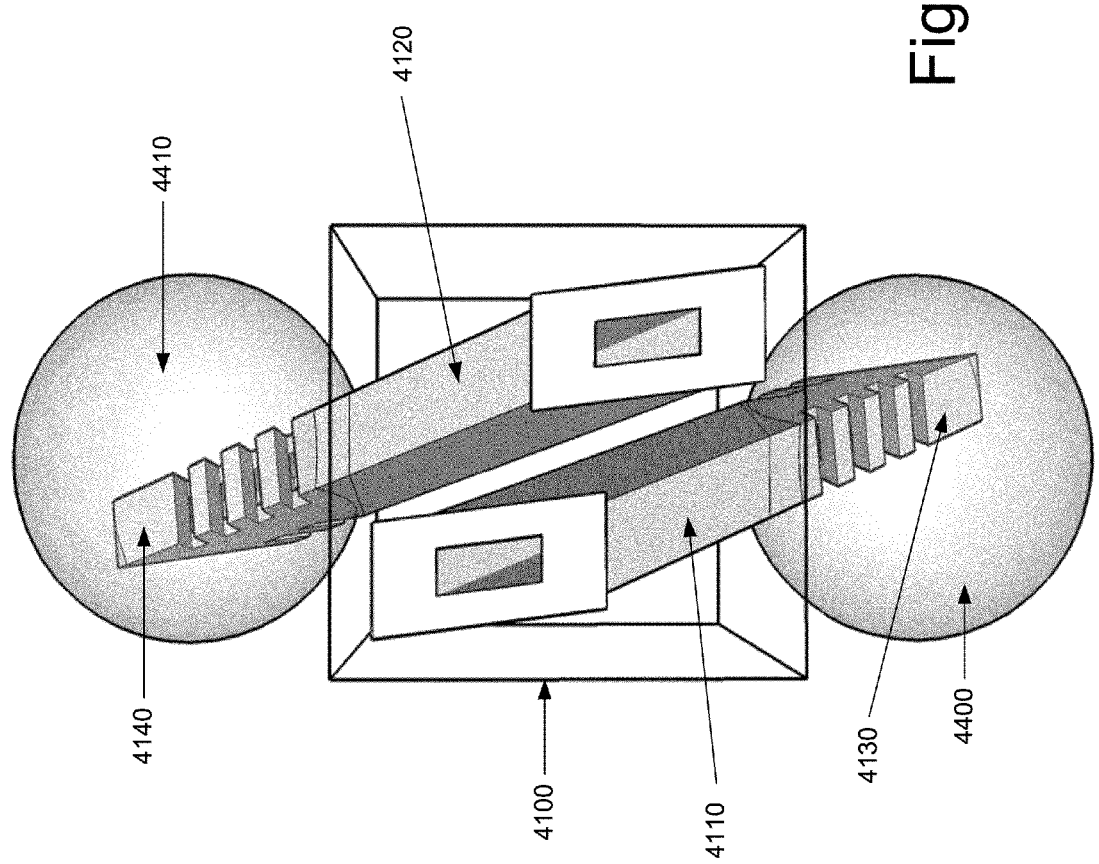

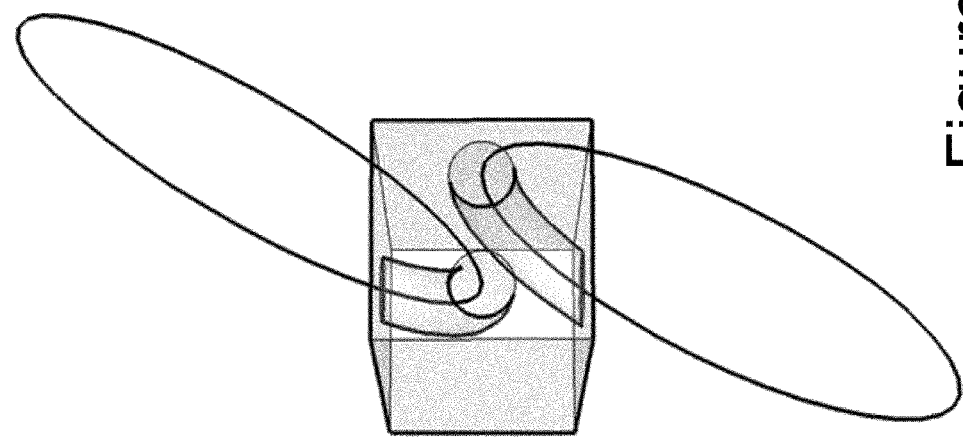
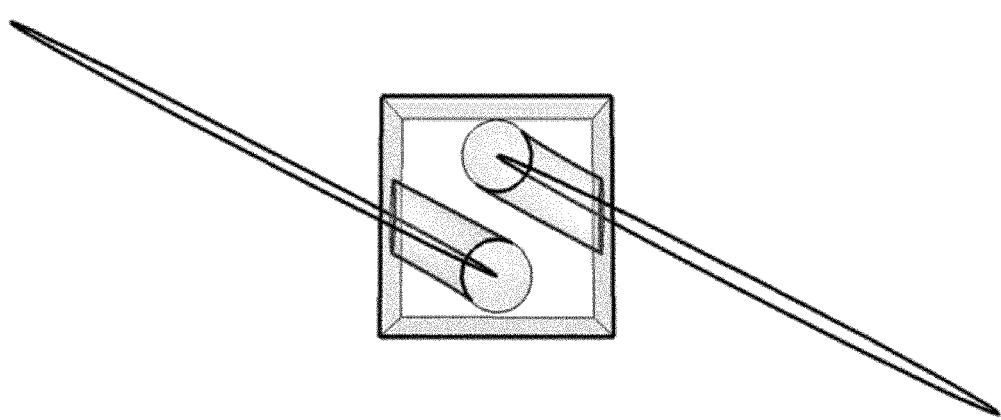
Figure 46B

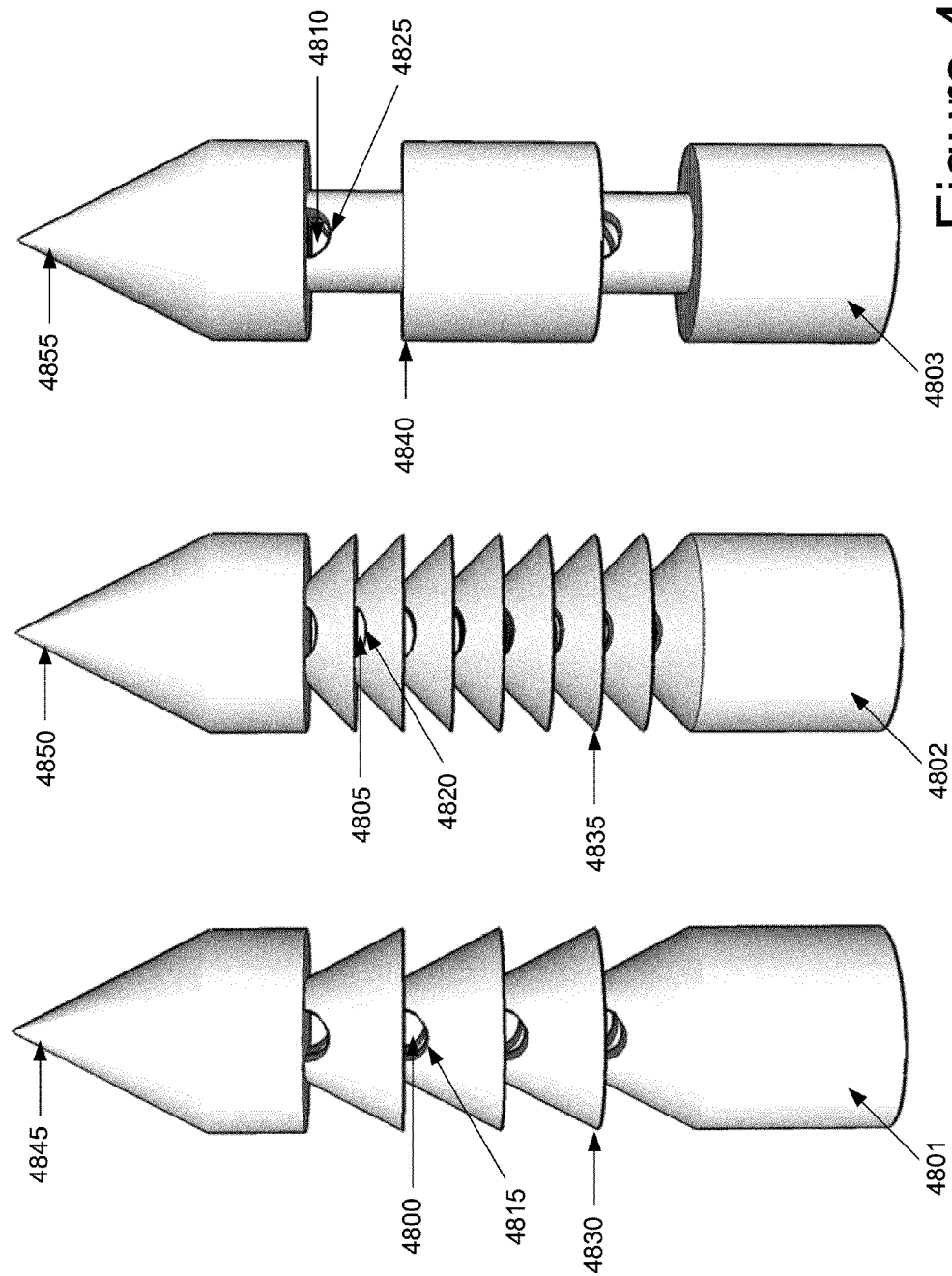

INTERVERTEBRAL FUSION DEVICE AND METHOD OF USE

CLAIM OF BENEFIT TO PRIOR APPLICATIONS

This application is a continuation application of U.S. patent application Ser. No. 12/383,950, filed Mar. 27, 2009, now issued as U.S. Pat. No. 8,382,839. U.S. patent application Ser. No. 12/383,950, now issued as U.S. Pat. No. 8,382,839, claims benefit to U.S. Provisional Patent Application 61/040,136, filed on Mar. 27, 2008; U.S. Provisional Patent Application 61/109,175, filed Oct. 28, 2008; and U.S. Provisional Patent Application 61/148,036, filed Jan. 28, 2009. U.S. patent application Ser. No. 12/383,950, now issued as U.S. Pat. No. 8,382,839, and the above-mentioned United States Provisional Patent Applications are incorporated herein by reference.

FIELD OF THE INVENTION

The invention pertains to spinal implants and surgical procedures for spinal fusion and stabilization.

BACKGROUND OF THE INVENTION

Back and neck pain are the leading causes of disability and lost productivity for American workers under the age of 45. Degenerative disc disease and its sequelae, whereby the fibrocartilaginous disc between adjacent vertebral bodies loses height, hydration and structural integrity, is one of the most common causes of back and neck pain and may develop secondary to traumatic injuries, inflammatory processes or various degenerative disorders. When conservative treatment fails, surgical fusion of the vertebral segments across the abnormal disc may be the only currently available procedure for pain relief. An increasing number of these spinal fusions are performed each year. It is estimated that over half a million of these procedures were performed in the United States last year alone.

Various surgical approaches to abnormal lumbar disc spaces are employed and include anterior interbody fusions, posterior interbody fusions and tranforaminal fusions. At cervical levels, an anterior approach is often employed. These procedures may be augmented by various posterior element instrumentation techniques. Regardless of the surgical approach, the goal is to achieve solid bony fusion between the involved endplates and eliminate the symptoms caused by motion and associated degenerative and other reactive changes between these unstable vertebral segments.

The first lumbar fusion procedures involved removal of a portion of the abnormal disc and placement of autologous bone graft material in the disc space without other instrumentation in the vertebral bodies or posterior elements. This approach often failed due to inadequate structural integrity. Subsequently, cortical bone dowels and femoral ring allografts were employed in an attempt to restore disc space height and augment structural integrity. After U.S. Pat. No. 4,961,740 ("Ray, et al.") introduced the concept of the threaded cylindrical interbody fusion cage in 1990, numerous other interbody fusion devices were developed. These devices include cylindrical, rectangular, and tapered cages and spacers composed of metals, polymers, human bone allograft and other materials. Some of these devices incorporate or are coated with human bone morphogenetic protein or other agents to promote new bone formation and accelerate fusion. Despite these advancements, failure rates for spinal fusion surgeries remain unacceptably high, greater than 10 percent in most series.

Therefore, there is a need in the art for an improved method to effect a more rapid, reliable fusion between unstable vertebral segments and avoid the considerable medical and economic impact of failed spinal fusions.

SUMMARY OF THE INVENTION

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies, (2) a delivery mechanism that delivers and positions the fusion member between the vertebral bodies, and (3) an anchoring member that affixes the fusion member to the vertebral bodies.

In some embodiments, the interbody fusion member is a shaped block (e.g., a rectangular or oblong block) with one or more channels (e.g., tubular channels). As mentioned above, this member is placed between endplates of adjacent vertebrae following a partial or complete discectomy. In this position, two or more sides of the fusion member are in contact with the opposed endplates. These contacting sides in some embodiments restore both disc height and physiologic lordosis. In some embodiments, these sides are parallel to each other, whereas in other embodiments, these sides are nonparallel such that the fusion member presents a tapered profile when viewed laterally. In this position, one or more anchoring members (e.g., one or more open-tipped or close-tipped needles) can be pushed through the one or more channels of the fusion member and into the marrow space of one or more of the vertebral bodies, in order to affix the fusion member to the vertebral bodies. This is further described below.

In some embodiments, the delivery mechanism that delivers the fusion member between vertebral bodies includes (1) a delivery housing that houses the anchoring mechanism and (2) a retention mechanism that couples the delivery housing to the fusion member. The delivery housing of some embodiments includes channels that run the entire length of the delivery housing that guide the anchoring mechanism to the proper channel opening of the fusion member. In some embodiments, the delivery housing also includes channels that guide retention rods toward the retention mechanism of some embodiments.

In some embodiments, the retention rods have retention teeth that mate with retention grooves on the fusion member. The retention rods, grooves, and teeth form the retention mechanism of some embodiments. Other embodiments might have different retention mechanisms. For instance, in some embodiments, the retention teeth are on the fusion member while the retention grooves are on the retention rod. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery mechanism to the fusion member.

The retention mechanism is used in some embodiments as a way of controllably detaching the delivery mechanism from the fusion member after the medical practitioner (1) determines that the fusion member is placed at the desired position between two vertebral bodies, and (2) inserts the anchoring members into the vertebral bodies in order to affix the fusion member to the vertebral bodies. When the medical practitioner determines (e.g., by viewing x-ray images of the patient) that the fusion member is not placed at an appropriate position between two vertebral bodies, the medical practitioner can use the delivery mechanism to reposition the fusion member to the desired location. One of ordinary skill will realize that the delivery mechanism and/or retention mechanism of some embodiments can be used for delivery of any type of interbody fusion members between two vertebral bodies (e.g., even those that do not utilize anchoring members).

As mentioned above, the anchoring members (e.g., large gauge needles 1-10 mm in outer diameter) are pushed through the channels of the delivery mechanism and the fusion member and into the marrow space of the vertebral bodies, in order to affix the fusion member to the vertebral bodies. Moreover, in some embodiments, polymethyl methacrylate (PMMA) or other bone cement or hardening polymer material, is injected through the anchoring members and into the vertebral bodies. In the marrow space of the vertebral bodies, this injected material forms a cloud around the tip of the anchoring member and hardens after a duration of time. Once this injected material hardens, it further solidifies the attachment of the fusion member to the vertebral bodies. To facilitate such injections, the anchoring members have hollow channels and perforated tips in some embodiments.

In some embodiments, the anchoring members are part of an anchoring mechanism that also includes driving members that advance the anchoring members through the fusion member channels into vertebral bodies. Some embodiments of the invention provide a coupling mechanism that couples each anchoring member to a corresponding driving member. In some embodiments, each driving member includes (1) a shaft that advances the anchoring member fully into the fusion member or withdraws the anchoring member from the fusion member and (2) a central lumen that provides a conduit for delivering polymers to the anchoring member.

The central lumen in the driving member aligns with the hollow channel (i.e., lumen) in its corresponding anchoring member once the anchoring member is in its desired position inside a vertebral body. Accordingly, once the driving members push the anchoring members into the vertebral bodies, hardening material (e.g., PMMA, bone cement, or other hardening polymer) may be injected through the central lumen of the driving and anchoring members. The polymer flows from the central lumen of the driving member, through the central lumen of the anchoring member, and into the marrow space of the vertebral bodies. This material passes through the perforations (i.e., openings) of the anchoring member into the marrow space of the vertebral body, contiguous with or adjacent to the anchoring member tip that is inside the marrow space. The polymer clouds in some embodiments form a spherical or ellipsoidal "cloud" of PMMA contiguous with the anchoring member tip. Once the polymer cloud hardens, the surface contours of the anchoring member serve to anchor this member to the vertebral body and prevent it from being withdrawn from the trabecular bone, and thereby enhances the structural integrity of the inserted fusion device yielding solid mechanical fusion.

To enhance the structural integrity of the coupling between the fusion device and the vertebral bodies, some embodiments define various surface contours along the anchoring member's tip. Examples of such contours include angled teeth and backfacing ridges. These contours (e.g., angled teeth and backfacing ridge) allow the anchoring member to pass through the fusion member's channel and into the bone (i.e., into the adjacent vertebral body). In some embodiments, hardening material might not be injected through the anchoring members. Instead, the insertion of the anchoring members and particular variations for the anchoring tip contours prevent the anchoring members from being easily withdrawn from the bone.

In some embodiments, the anchoring member and driving member coupled together form a unified needle. In such an embodiment, the anchoring member is the embedded portion that is embedded in the vertebral bodies while the driving member is the retractable portion that is removed once the fusion member has been affixed to the vertebral bodies between which it is placed.

Once the anchoring members are in place, and the polymers have been injected into the marrow space of the vertebral bodies, the driving members and delivery mechanism may be removed, as mentioned above.

BRIEF DESCRIPTION OF THE DRAWINGS

The novel features of the invention are set forth in the appended claims. However, for purpose of explanation, several embodiments of the invention are set forth in the following figures.

FIGS. 8-9 provide different perspectives of the retention rod of the delivery mechanism.

FIGS. 22A-22B illustrate exploded views of the pivoting mechanism from different perspectives.

FIGS. 44-45 illustrate different views of PMMA that has been injected and forms collections contiguous with the perforated, contoured tips of anchoring members within the marrow spaces of adjacent vertebral bodies.

FIGS. 46A, 46B, and 47 illustrate different views of an alternative fusion member embodiment comprising curved tubular channels that run in parallel planes with respect to each other but are nonparallel to the adjacent faces of the fusion block member.

FIGS. 48A-48D illustrate alternative anchoring member tips.

DETAILED DESCRIPTION OF THE INVENTION

Figure 1A:
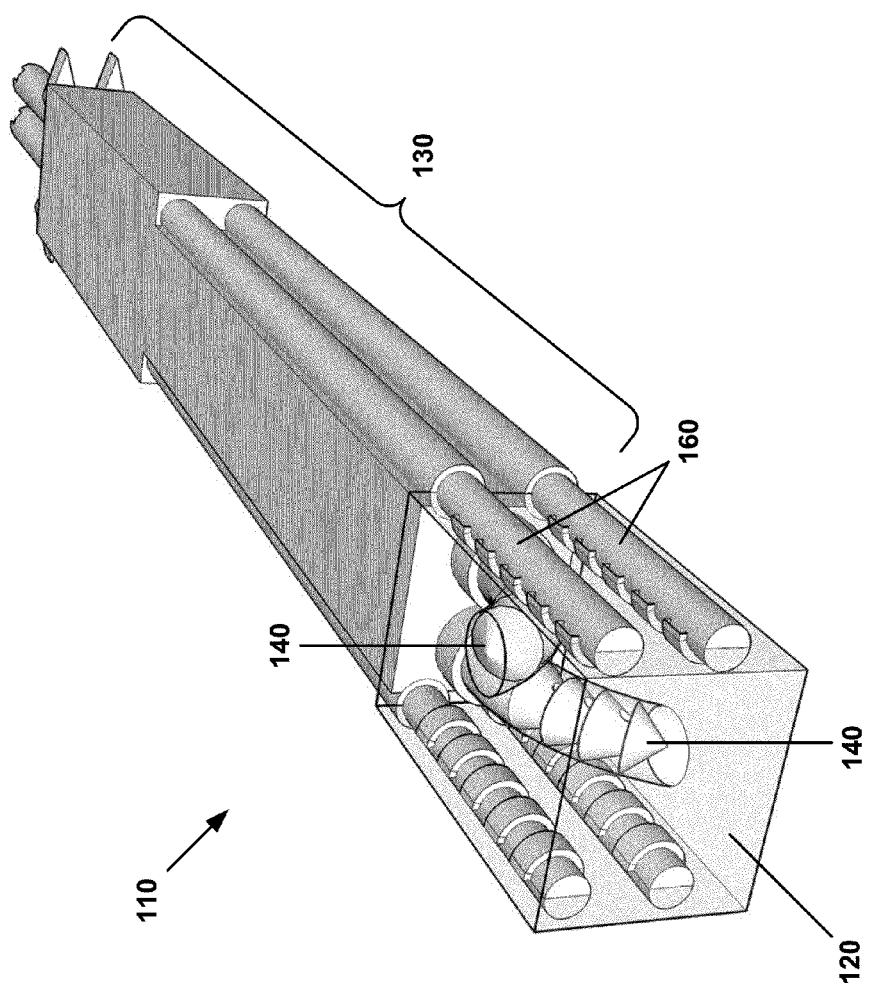
FIG. 1A provides a front perspective of the intervertebral apparatus.

In the following description, numerous details are set forth to provide a better understanding of the various embodiments of the invention. However, one of reasonable skill in the art will realize that the invention may be practiced without the use of the specific details presented herein. In some instances of describing the invention, well-known structures may be omitted or shown in block diagram form to avoid obscuring the description of the invention with unnecessary detail. Therefore, the examples provided herein for description and clarification should not be interpreted as in anyway limiting the language of the claims.

I. Overview

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies. In some embodiments, the apparatus includes (1) a fusion member that is delivered and positioned between the vertebral bodies, (2) a delivery mechanism that delivers and positions the fusion member between the vertebral bodies, and (3) an anchoring member that affixes the fusion member to vertebral bodies.

In some embodiments, the interbody fusion member is a shaped block (e.g., a rectangular or oblong block) with one or more channels (e.g., tubular channels). As mentioned above, this member is placed between endplates of adjacent vertebrae following a partial or complete discectomy. In this position, two or more sides of the fusion member are in contact with the opposed endplates. These contacting sides may be parallel to each other, or nonparallel such that the fusion member presents a tapered profile when viewed laterally so as to restore both disc height and physiologic lordosis. In this position, one or more anchoring members (e.g., one or more open-tipped or close-tipped needles) can be pushed through the one or more channels of the fusion member and into the marrow space of one or more of the vertebral bodies, in order to affix the fusion member to the vertebral bodies. This is further described below.

In some embodiments, the delivery mechanism that delivers the fusion member between vertebral bodies includes (1) a delivery housing that houses the anchoring mechanism and (2) a retention mechanism that couples the delivery housing to the fusion member. In some embodiments, the delivery housing also includes channels that guide retention rods of the retention mechanism of some embodiments.

In some embodiments, the retention rods have retention teeth that mate with retention grooves on the fusion member. The retention rods, grooves, and teeth form the retention mechanism of some embodiments. Other embodiments might have different retention mechanisms. For instance, in some embodiments, the retention teeth are on the fusion member while the retention grooves are on the retention rod. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery mechanism to the fusion member.

The retention mechanism is used in some embodiments as a way of controllably detaching the delivery mechanism from the fusion member after the medical practitioner (1) determines that the fusion member is placed at the desired position between two vertebral bodies, and (2) inserts the anchoring members into the vertebral bodies in order to affix the fusion member to the vertebral bodies. When the medical practitioner determines (e.g., by viewing x-ray images of the patient) that the fusion member is not placed at an appropriate position between two vertebral bodies, he can use the delivery mechanism to reposition the fusion member to the desired location. One of ordinary skill will realize that the delivery mechanism and/or retention mechanism of some embodiments can be used for delivery of any type of interbody fusion members between two vertebral bodies (e.g., even those that do not utilize anchoring members and/or PMMA or bone cement).

As mentioned above, the anchoring members (e.g., large gauge needles 1-10 mm in outer diameter) are pushed through the channels of the delivery mechanism and the fusion member and into the marrow space of the vertebral bodies, in order to affix the fusion member to the vertebral bodies. Moreover, in some embodiments, polymethyl methacrylate (PMMA) or other bone cement or hardening polymer material, is injected through the anchoring members and into the vertebral bodies. In the marrow space of the vertebral bodies, this injected material forms a cloud around the tip of the anchoring member and hardens after a duration of time. Once this injected material hardens, it further solidifies the attachment of the fusion member to the vertebral bodies. To facilitate such injections, the anchoring members have hollow channels and perforated tips in some embodiments.

In some embodiments, the anchoring members are part of an anchoring mechanism that also includes driving members that advance the anchoring members through the fusion member channels into vertebral bodies. Some embodiments of the invention provide a coupling mechanism that couples each anchoring member to a corresponding driving member. In some embodiments, each driving member includes (1) a shaft that advances the anchoring member fully into the fusion member or withdraws the anchoring member from the fusion member and (2) a central lumen that provides a conduit for delivering polymers to the anchoring member.

The central lumen in the driving member aligns with the hollow channel (i.e., lumen) in its corresponding anchoring member once the anchoring member is in its desired position inside a vertebral body. Accordingly, once the driving members push the anchoring members into the vertebral bodies, hardening material (e.g., PMMA, bone cement, or other hardening polymer) may be injected through the central lumen of the driving and anchoring members. The polymer flows from the central lumen of the driving member, through the central lumen of the anchoring member, and into the marrow space of the vertebral bodies. This material passes through the perforations (i.e., openings) of the anchoring member into the marrow space of the vertebral body, contiguous with or adjacent to the anchoring member tip that is inside the marrow space. The polymer clouds in some embodiments form a spherical or ellipsoidal "cloud" of PMMA contiguous with the anchoring member tip. Once the polymer cloud hardens, the surface contours of the anchoring member serve to anchor this member to the vertebral body and prevent it from being withdrawn from the trabecular bone, and thereby enhances the structural integrity of the inserted fusion device yielding solid mechanical fusion.

To enhance the structural integrity of the coupling between the fusion device and the vertebral bodies, some embodiments define various surface contours along the anchoring member's shaft. Examples of such contours include angled teeth and backfacing ridges. These contours (e.g., angled teeth and backfacing ridge) allow the anchoring member to pass through the fusion member's channel and into the bone (i.e., into the adjacent vertebral body). In some embodiments, hardening material might not be injected through the anchoring members. Instead, the insertion of the anchoring members and particular variations for the anchoring tip contours prevent the anchoring members from being easily withdrawn from the bone.

In some embodiments, the anchoring member and driving member coupled together form a unified entity, the anchoring member. In such an embodiment, the anchoring member is the embedded portion that is embedded in the vertebral bodies while the driving member is the retractable portion that is removed once the fusion member has been affixed to the vertebral bodies between which it is placed.

Once the anchoring members are in place, and the polymers have been injected into the marrow space of the vertebral bodies, the driving members and delivery mechanism may be removed, as mentioned above.

One of ordinary skill will realize that although several embodiments have been described above, other embodiments might be implemented or operated differently. For instance, before advancing the anchoring members into the vertebral bodies as described above, some embodiments first advance a smaller gauge anchoring member into the marrow space of the adjacent vertebral body before placement of the larger gauge anchoring member. This creates a guide to help ensure that the larger gauge anchoring member will be advanced into the proper position within the trabecular bone of the vertebral body.

To better understand these embodiments, it is helpful to understand relevant terminology and describe examples of the invention in use. Therefore, the following sections present relevant terminology, and provide an overview of an exemplary fusion procedure of some embodiments and of a number of more specific design features and variations.

II. Definitions and Terminology

The spinal column of humans and other vertebrates comprises vertebral bodies and posterior osseous elements that provide structural support and also serve to protect the spinal cord and other spinal canal contents. The vertebral bodies are the cylindrical segmental osseous structures that form the anterior margin of the spinal canal and are separated from each other by fibrocartilaginous intervertebral discs. In the present discussion, the term "fusion member" refers to a device positioned between vertebral bodies. In some embodiments, the fusion member has one or more channels for the passage of contoured anchoring members and/or the retention and positioning of bone graft material or bone graft substitutes between adjacent vertebral bodies.

III. Components of the Fusion Member, Delivery Mechanism, and Anchoring Member(s)

Some embodiments of the invention provide an apparatus that (1) delivers a fusion member between two vertebral bodies after at least a portion of the fibrocartilaginous disc between the vertebral bodies has been removed, and (2) affixes the fusion member to the vertebral bodies.

Figure 1B:
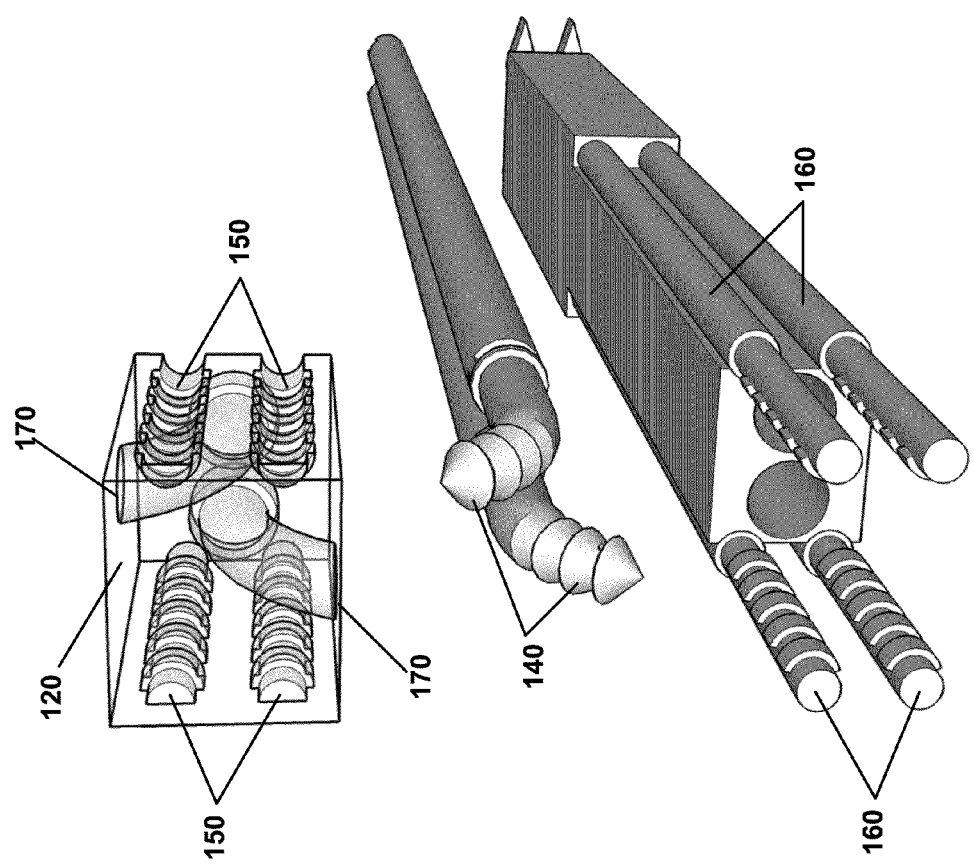
FIGS. 1B and 1C provide different perspectives of an exploded view of the intervertebral apparatus.
Figure 1C:
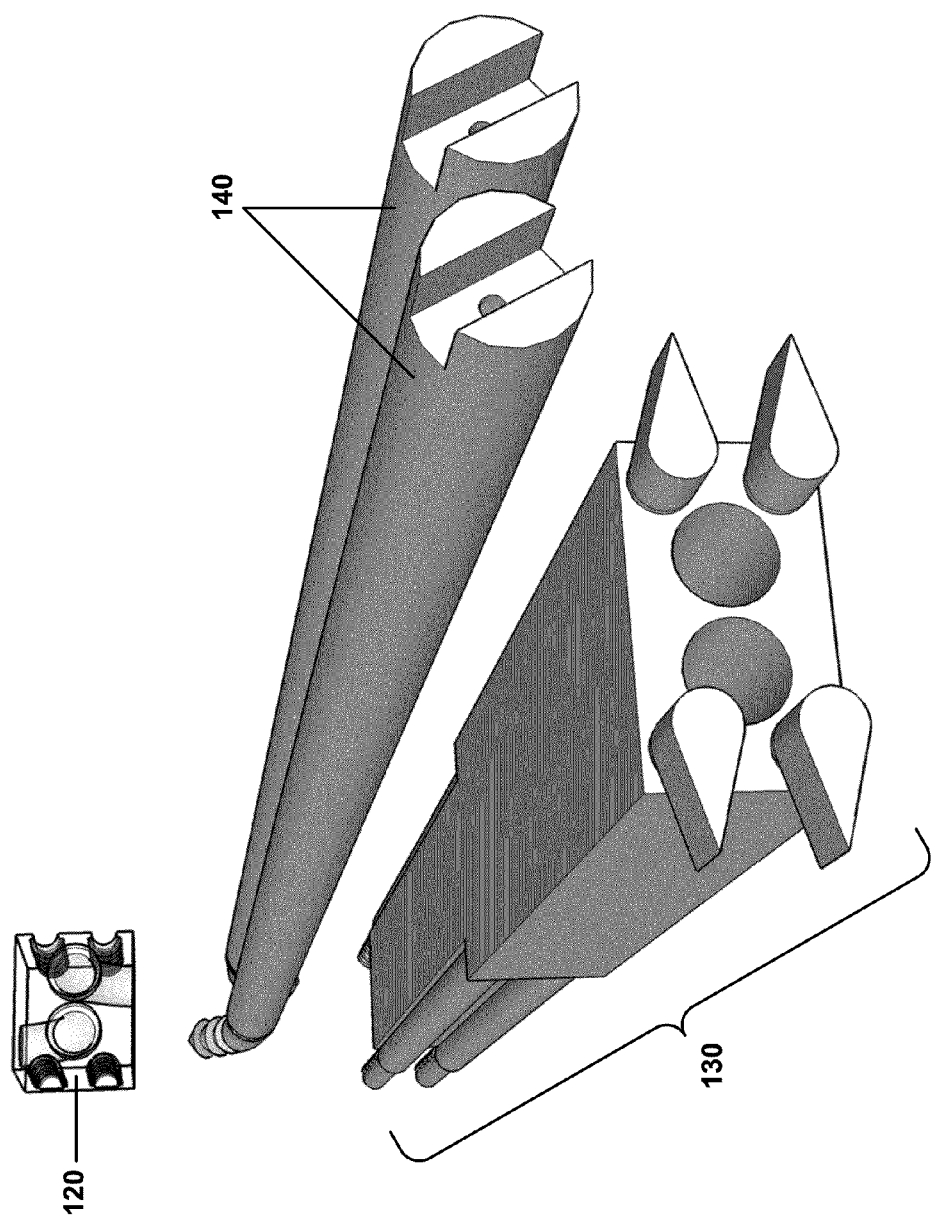
Figure 2:
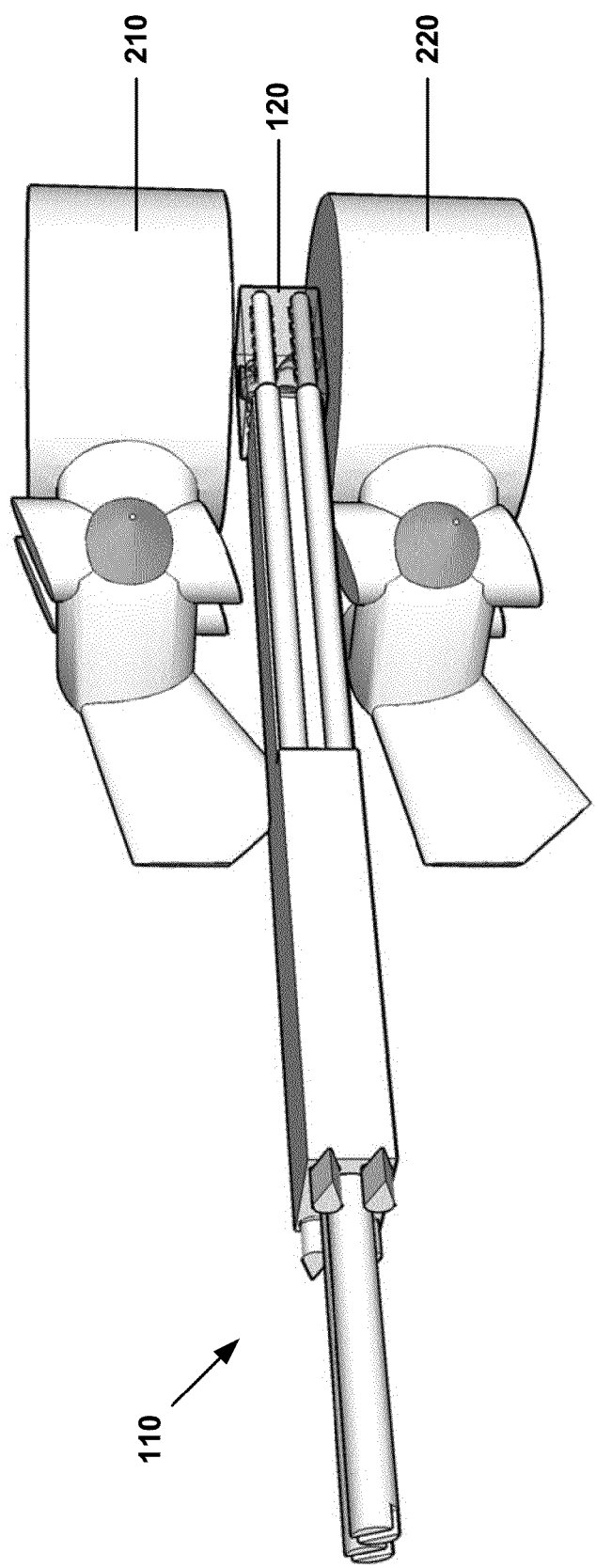
FIGS. 2-3 illustrate the intervertebral apparatus in relation to two vertebral bodies between which the fusion member is placed.
Figure 3:
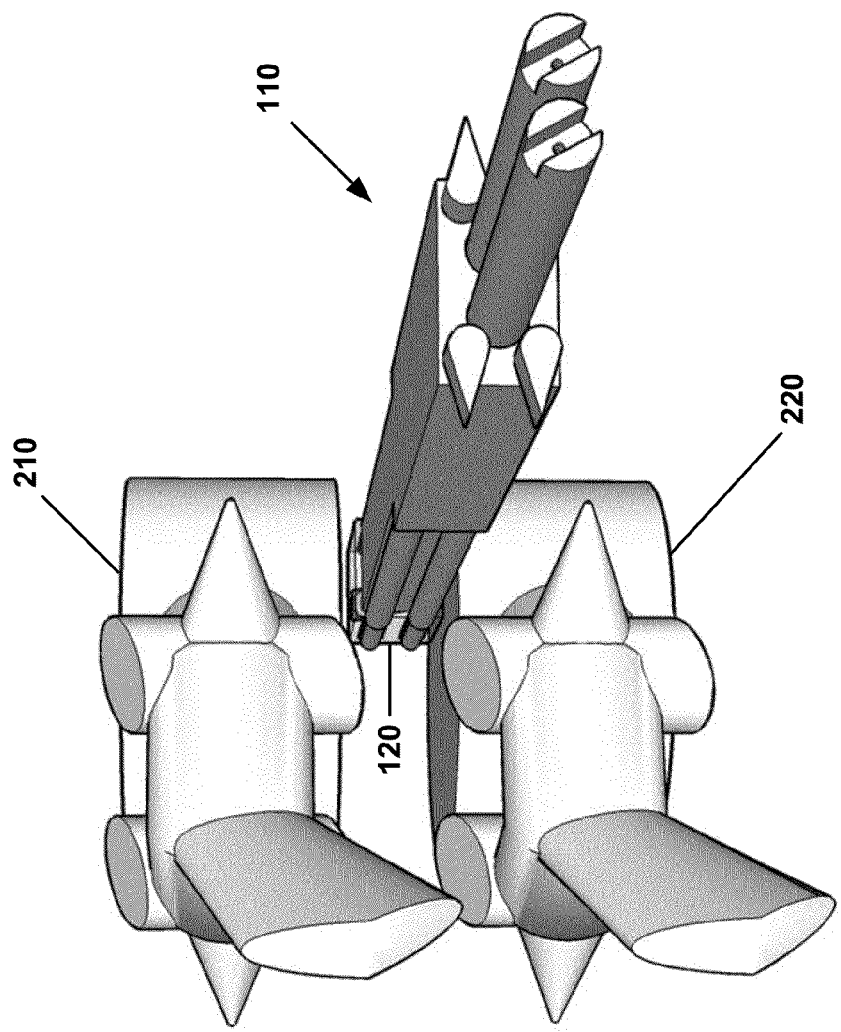

FIGS. 1-3 illustrate an example of one such apparatus according to some embodiments. FIG. 1A provides a front view of the apparatus 110. FIGS. 1B and 1C provide different perspectives of an exploded view of the apparatus 110. FIG. 2 provides a side view of the apparatus 110 in relation to two vertebral bodies 210-220 between which a fusion member 120 is placed. FIG. 3 provides a rear view of the apparatus 110 in relation to the two vertebral bodies 210-220 between which the fusion member 120 is placed.

As shown in these figures, the apparatus 110 includes (1) a fusion member 120 that is delivered and positioned between the vertebral bodies 210-220, (2) a delivery mechanism 130 that delivers and positions the fusion member 120 between the vertebral bodies 210-220, and (3) anchoring mechanisms 140 that affix the fusion member 120 to the vertebral bodies 210-220. Each of these components will be described in further detail below.

A. Fusion Member

As mentioned above, the apparatus 110 includes a fusion member 120 that is delivered and positioned between the vertebral bodies 210-220. The fusion member 120 includes (1) two channels 170 through which two anchoring mechanisms can be advanced, and (2) retention grooves 150 of a retention mechanism for attaching the fusion member to the delivery mechanism.

Figure 4:
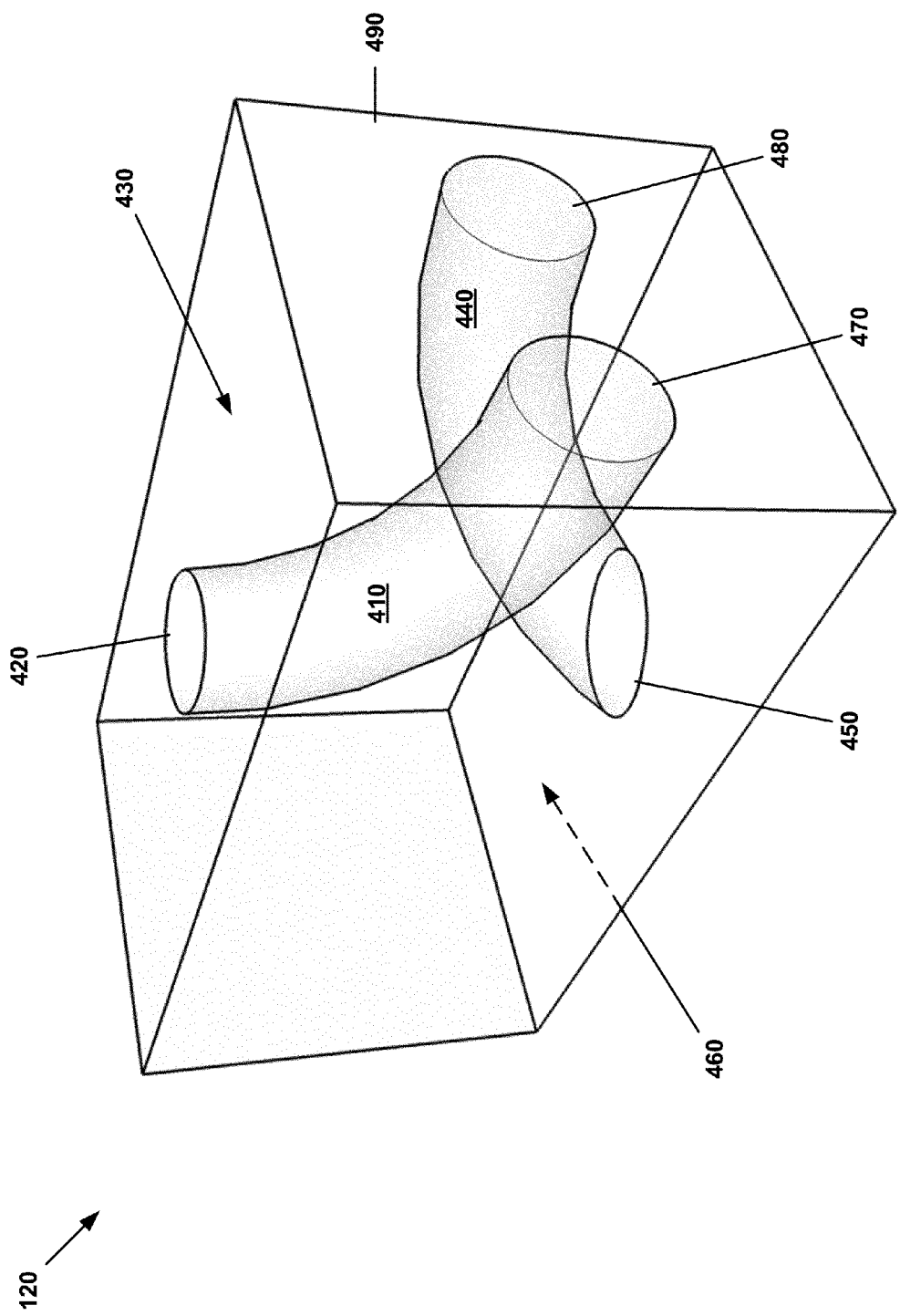
FIG. 4 illustrates one perspective of the fusion member which includes channels through which anchoring mechanisms can be inserted and advanced.

FIG. 4 illustrates a perspective view of the fusion member 120 of some embodiments of the invention. In this and some of the subsequent figures, fusion members are shown transparently to facilitate an appreciation of the spatial relationships between multiple channels and their openings upon multiple faces of the fusion member.

As shown in FIG. 4, the fusion member 120 includes channels 410 and 440 through which anchoring mechanisms can be inserted and advanced. Channel 410 has a distal opening 420 on the superior face 430 of the fusion member 120. Channel 440 has a distal opening 450 on the inferior face 460 of the fusion member 120. Channel 410 has a proximal opening 470 on the proximal face 490 of the fusion member 120. Channel 440 also has a proximal opening 480 on the proximal face 490 of the fusion member 120. Some embodiments of the fusion member provide a recess of increased diameter (e.g., flange cavity, anchoring member cavity, etc.) on the channel opening on the proximal face of the fusion member (one such example will be described below by referring to the anchoring member cavity 1685-1690 of FIG. 16 and the anchoring member cavity 1720 of FIG. 17).

As shown in the example illustrated in FIG. 4, the cross-sectional planes of the fusion member channels 410 and 440 are parallel to each other, but are not parallel to the right and left face of the fusion member 120. This allows the distal opening 420 of channel 410 to be located on the center of the superior 430 face of the fusion member, and the distal opening 450 of channel 440 to be located on the center of the inferior 460 face of the fusion member even though their proximal opening 470 and 480 start on the same proximal face 490. Even though the fusion member channels shown in these figures are curved and tubular, one of ordinary skill in the art will know that the channels may be other shapes or configurations in other embodiments as later described in Section V.

Figure 5A:
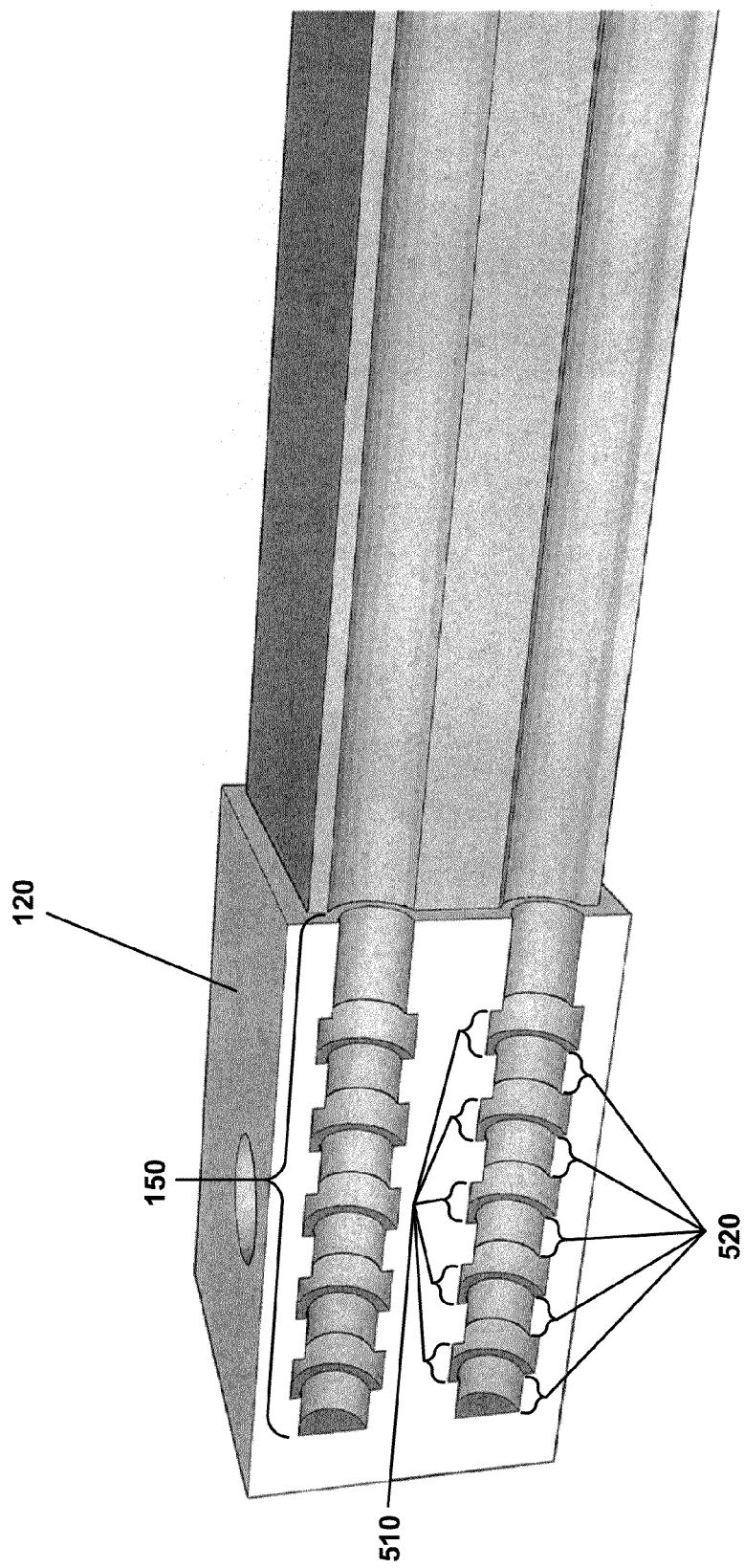
FIG. 5A-5B provide an illustration of the fusion member and retention grooves without the retention rods of the delivery mechanism.
Figure 5B:
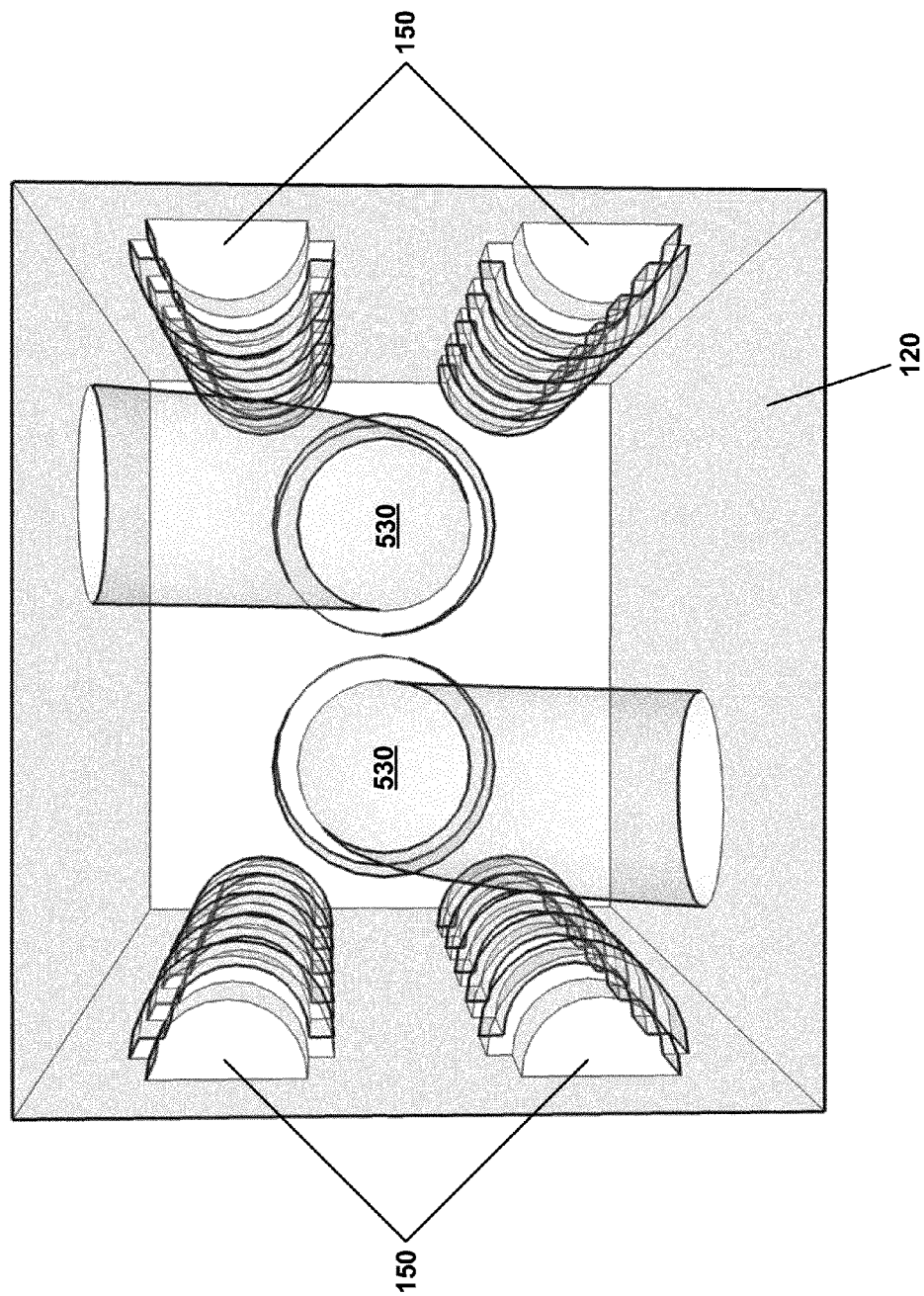

FIG. 5A provides an illustration of the fusion member 120 and two sets of retention grooves 150 located on the left side of the fusion member 120 without the retention rods of the delivery mechanism. The two sets of retention grooves on the right side of the fusion member are not shown in this figure. FIG. 5B provides a front perspective of the fusion member 120 with the two sets of retention grooves 150 located on the left side of the fusion member 120 and two sets of retention grooves 150 located on the right side of the fusion member 120. The two sets of retention grooves couple with the retention rods of the delivery mechanism. Both the delivery mechanism and the retention rods will be described in further detail below.

As shown in FIG. 5A-5B, each set of retention grooves 150 includes two subsets of grooves (i.e., indentations, cavities, etc.) that differ in diameter, a first set of grooves 520 having a smaller diameter than a second set of grooves 510. These figures show the first subset of grooves 520 with six indentations that are smaller in diameter than the second subset of grooves 510 with five indentations that are larger in diameter. The first subset of grooves 520 couples with the shaft of a retention rod while the second subset of grooves 510 couples with the teeth of the retention rod as further described below. In some embodiments, the retention grooves of the fusion member couple with retention rods of the delivery mechanism to form a retention mechanism. The retention teeth of the rods are the male coupling members of the retention mechanism while the retention grooves of the fusion members are the female coupling members of this mechanism.

In the example illustrated in FIGS. 5A-5B, two subsets of retention grooves 150 are located on the left side of the fusion member and two subsets of retention grooves are located on the right side of the fusion member. However, one of ordinary skill in the art will realize that the retention mechanism and retention grooves can be in another location on the fusion member, such as in the interior of the fusion member, and can vary in shape, size, and number. Also, other embodiments might have different retention mechanisms. For instance, in some embodiments, the retention teeth are on the fusion member while the retention grooves are on the retention rod. Moreover, instead of, or in conjunction with, this tooth and groove approach, one of ordinary skill will realize that other embodiments use other retention structures (e.g., other male/female structures, other structures such as expandable clasps that encapsulate the lateral edges of the fusion member, other structures such as a clamp, etc.) to affix the delivery mechanism to the fusion member.

Also, in the example illustrated in FIG. 5B, the cross-sectional view of the two channels 530 that go through the fusion member 120 are parallel to the right and left side of the fusion member 120. This is a different channel implementation than the channels 410 and 440 of the example illustrated in FIG. 4. As mentioned above, the cross-section planes of those two channels 410 and 440 are not parallel to the right and left sides of the fusion member, even though they are parallel to each other.

In some embodiments, the fusion member can be composed of any number of materials, such as metals (e.g., stainless steel, titanium, or nitinol), various polymers (e.g., PMMA or polyetheretherketone), carbon fiber, etc. The fusion member can also be partially or be completely made of bioabsorbable or biodegradable materials, so that it can be partially or be completely absorbed. In some embodiments, the fusion member's faces that are in contact with the vertebral endplates may have surface contours such as ridges to enhance stability. The fusion member can also include additional channels or cavities to be packed with bone graft material or bone graft substitutes to enhance progressive solid bony fusion. Bone graft material and bone graft substitutes can also be packed into the intervertebral space surrounding and between the fusion members to enhance progressive solid bony fusion. The fusion member can also be coated with or partially be composed of human bone morphogenetic protein or other bone growth inducing substances.

Typically, the fusion member is inserted between adjacent vertebral bodies after at least some of the fibrocartilaginous disc between the adjacent vertebral bodies is removed during a partial or complete discectomy. Once the fusion member is delivered to the proper location between adjacent vertebral bodies, two or more sides of the fusion member may be in contact with the opposed endplates of the adjacent vertebral bodies. These contacting sides in some embodiments restore both disc height and physiologic lordosis. In some embodiments, these sides are parallel to each other, whereas in other embodiments, these sides are nonparallel such that the fusion member presents a tapered profile when viewed laterally. The delivery mechanism that inserts the fusion member between the vertebral bodies will be described below.

B. Delivery Mechanism

Figure 6:
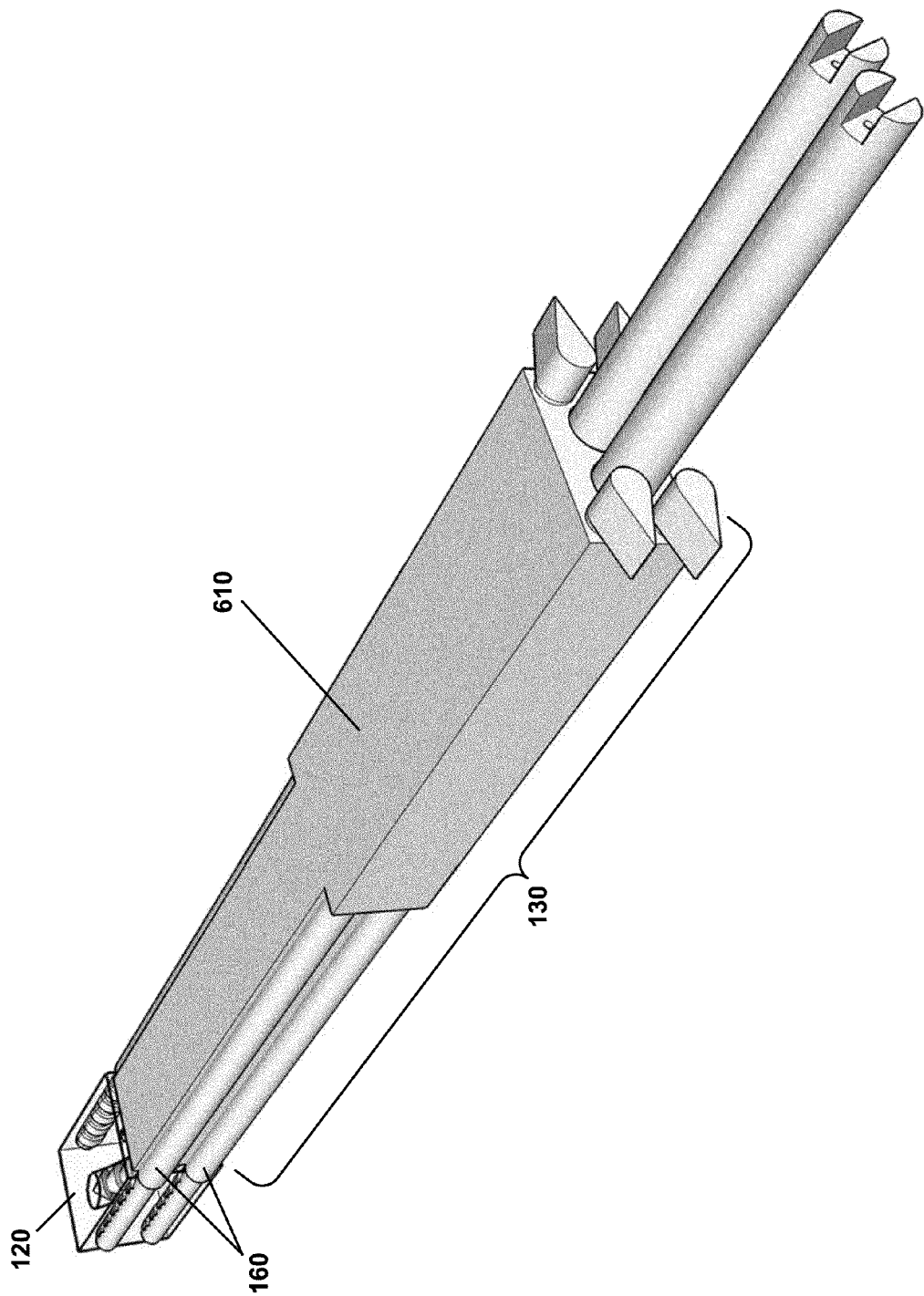
FIG. 6 shows a perspective view of the delivery mechanism coupled with the fusion member.

As mentioned above, the delivery mechanism delivers the fusion member between adjacent vertebral bodies. FIG. 6 shows a perspective view of the delivery mechanism 130 coupled with the fusion member 120. The delivery mechanism includes (1) a delivery housing 610 that houses the anchoring mechanism and retention rods 160, and (2) four retention rods 160 that couple the delivery housing 610 with the fusion member 120. From this perspective, only three of the four retention rods can be seen.

Figure 7A:
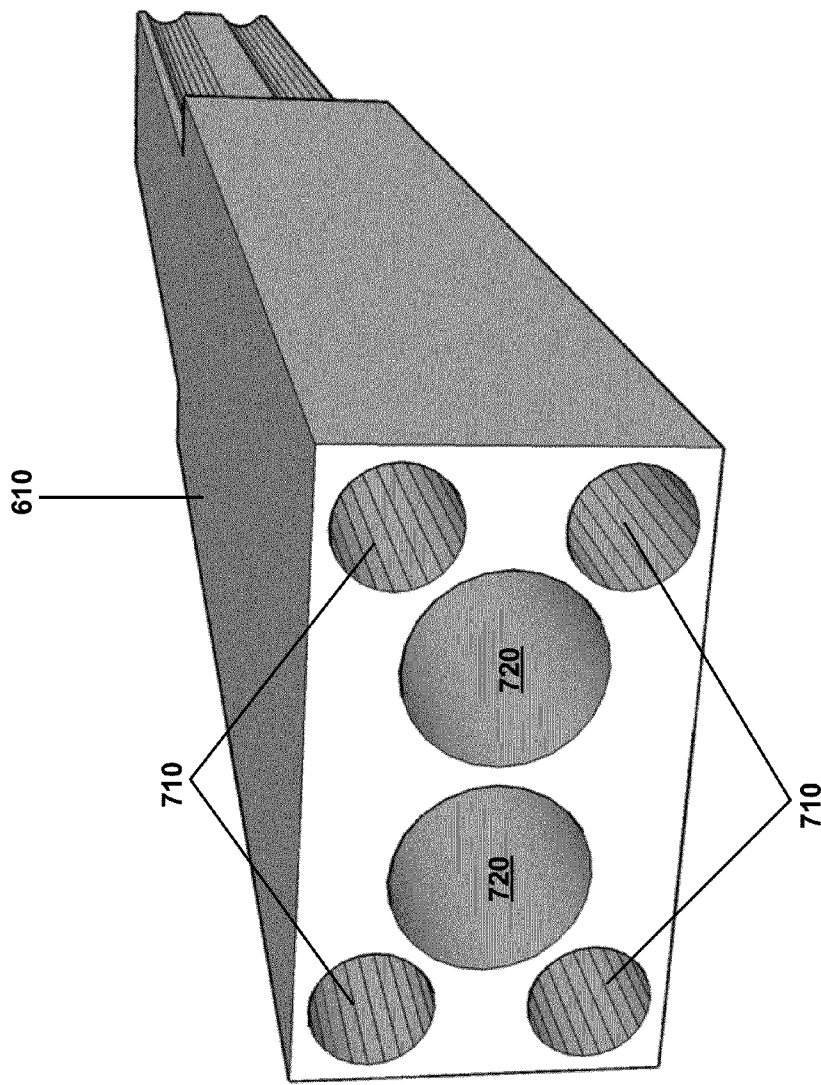
FIG. 7A illustrates the delivery housing from the perspective of the operator.
Figure 7B:
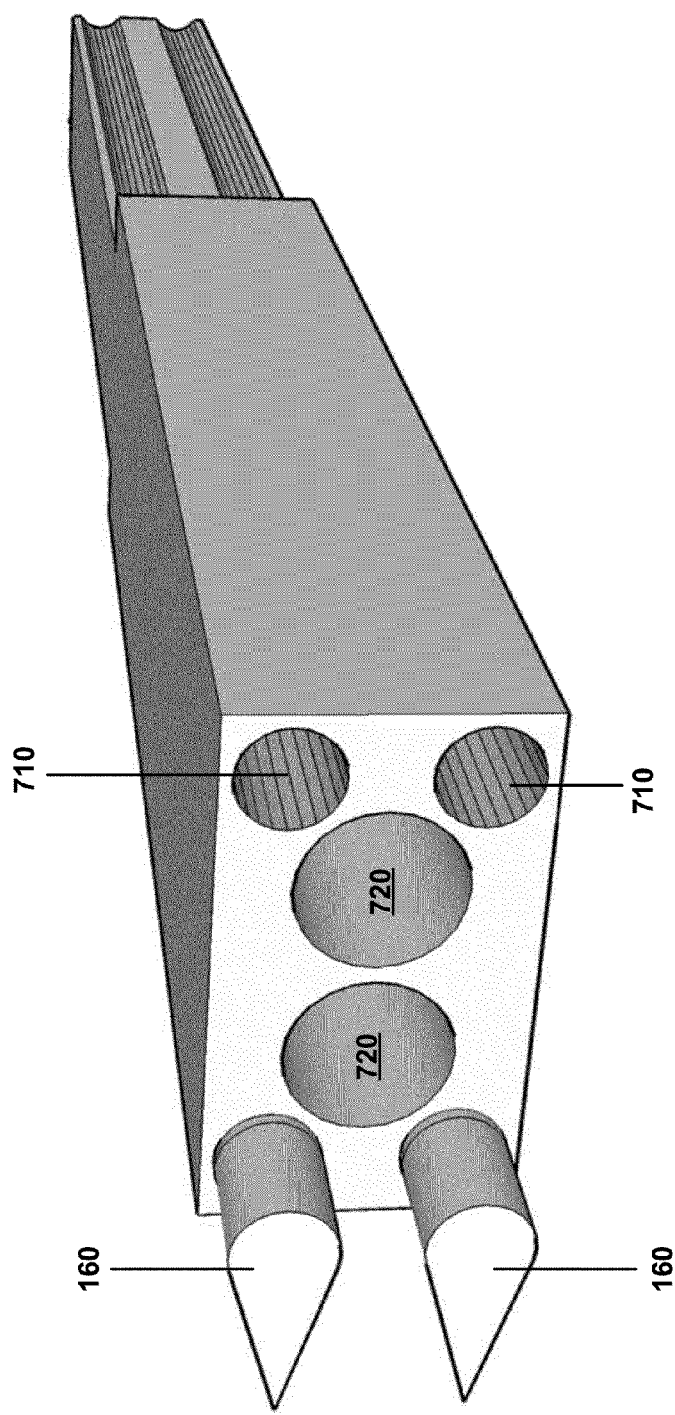
FIGS. 7B-7C illustrate the delivery housing with two retention rods in the delivery housing channels from the perspective of the operator and from the perspective opposite of the operator.
Figure 7C:
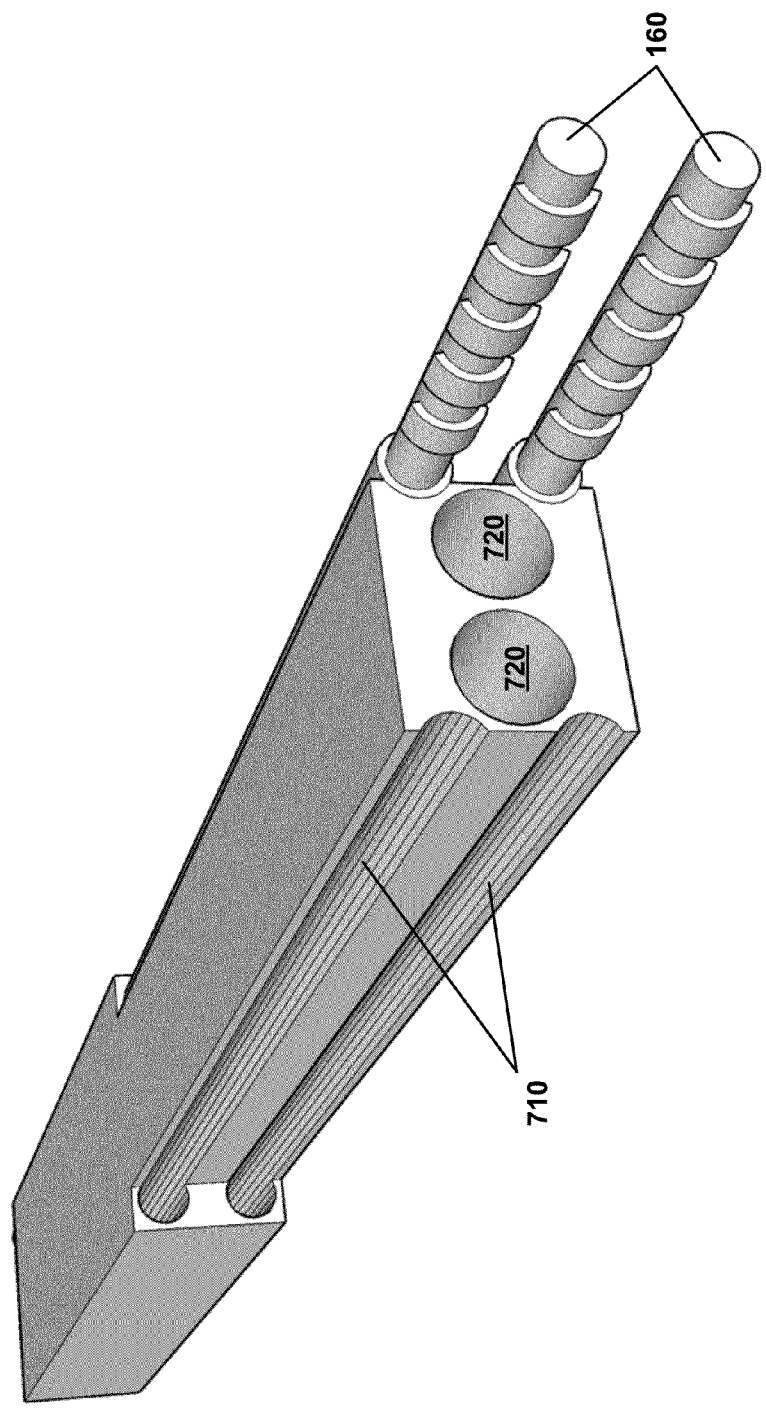

FIG. 7A illustrates the delivery housing 610 from the perspective of the operator during an operation (i.e., the backside of the delivery mechanism during an operation). FIGS. 7B and 7C illustrate the delivery housing with two retention rods 160 in channels 710 from the perspective of the operator and from the perspective opposite of the operator during an operation (i.e., from the front side of the delivery mechanism during an operation).

As shown in FIGS. 7A and 7B, the delivery housing 610 includes circular channels 710 and 720 that run the entire length of the delivery housing 610, from the distal end of the delivery housing to the proximal end of the delivery housing. In some embodiment, these channels have the same diameter throughout the entire length of the channel. The two channels 720 house and guide the anchoring mechanism (not pictured) to the proper channel opening of the fusion member, whereas the four channels 710 house and retain the retention rods. One of ordinary skill in the art will realize that any number of channels that house the retention rods and the anchoring mechanism can be used. The delivery housing channels can be of various shapes and sizes to accommodate the various shapes and sizes of the anchoring mechanism and retention rods. The anchoring mechanism will be described in further detail in Section C.

As mentioned above, the retention mechanism attaches the delivery housing to the fusion member. In some embodiments, the retention mechanism is used as a way of controllably detaching the delivery mechanism from the fusion member after the medical practitioner determines that the fusion member is placed at the desired position between two vertebral bodies.

Figure 8:
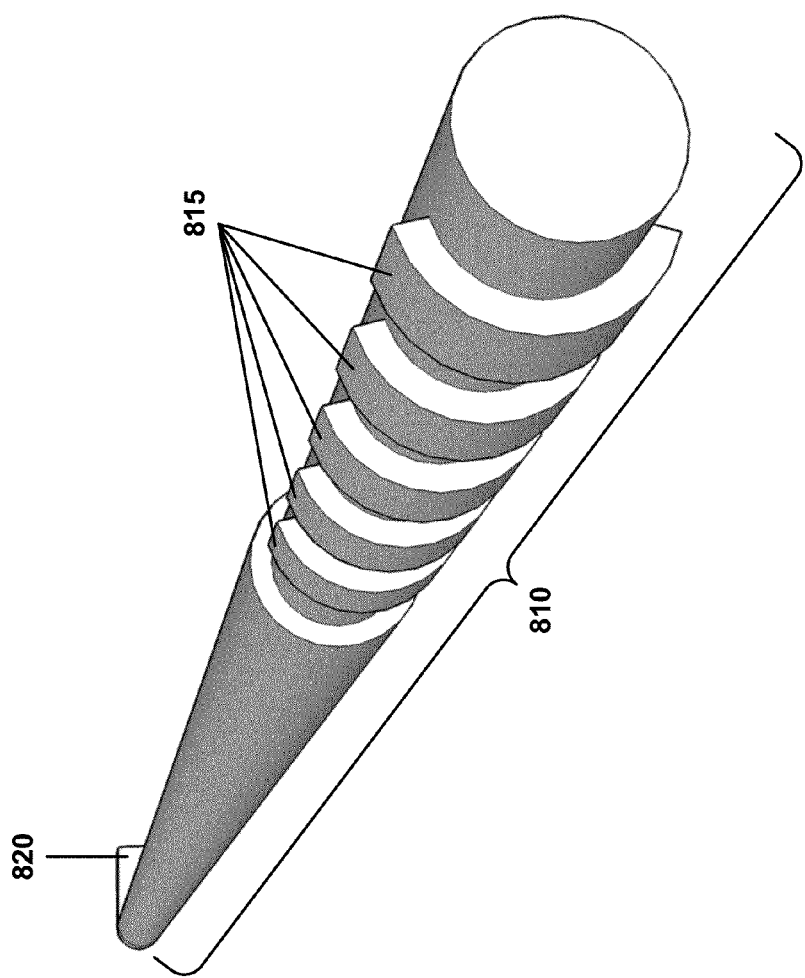

The retention mechanism that is illustrated in FIGS. 6-7 includes (1) retention rods 160 of the delivery mechanism 130, and (2) sets of retention grooves 150 of the fusion member 120, which couple with retention rods 160 of the delivery mechanism 130. As shown in FIGS. 8-9 each retention rod in some embodiments includes (1) a shaft 810 with a distal end that couples with the subset of smaller retention grooves 520, (2) retention teeth 815 on the distal end of the shaft 810 that couple with the subset of larger retention grooves 510, and (3) a handle 820 on the proximal end of the shaft that rotates the retention rod.

Figure 10A:
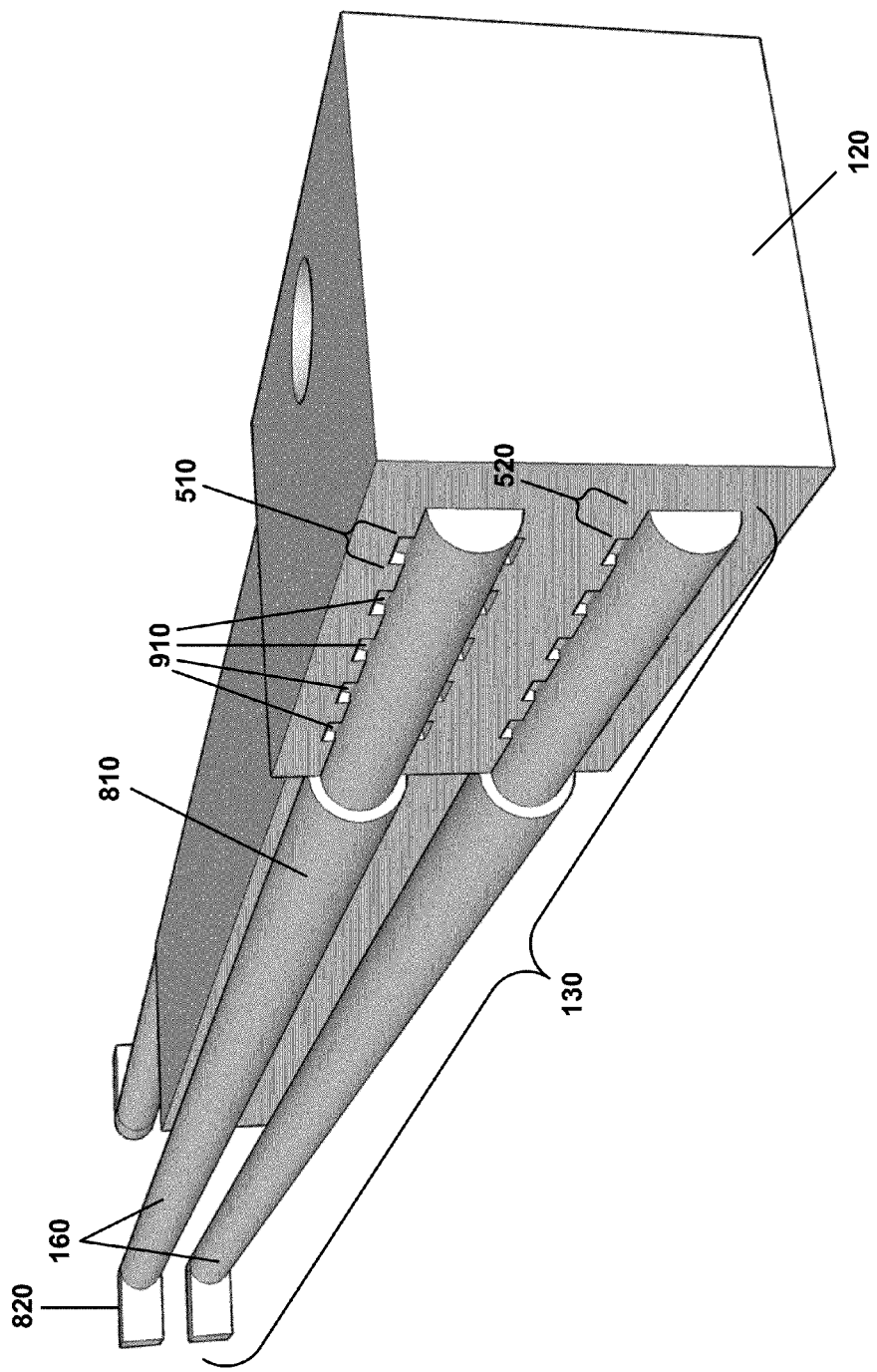
FIGS. 10A-10C (1) illustrate an example of the process of controllably detaching the delivery mechanism from the fusion member and (2) provide a detailed view of one of the retention rods.
Figure 10B:
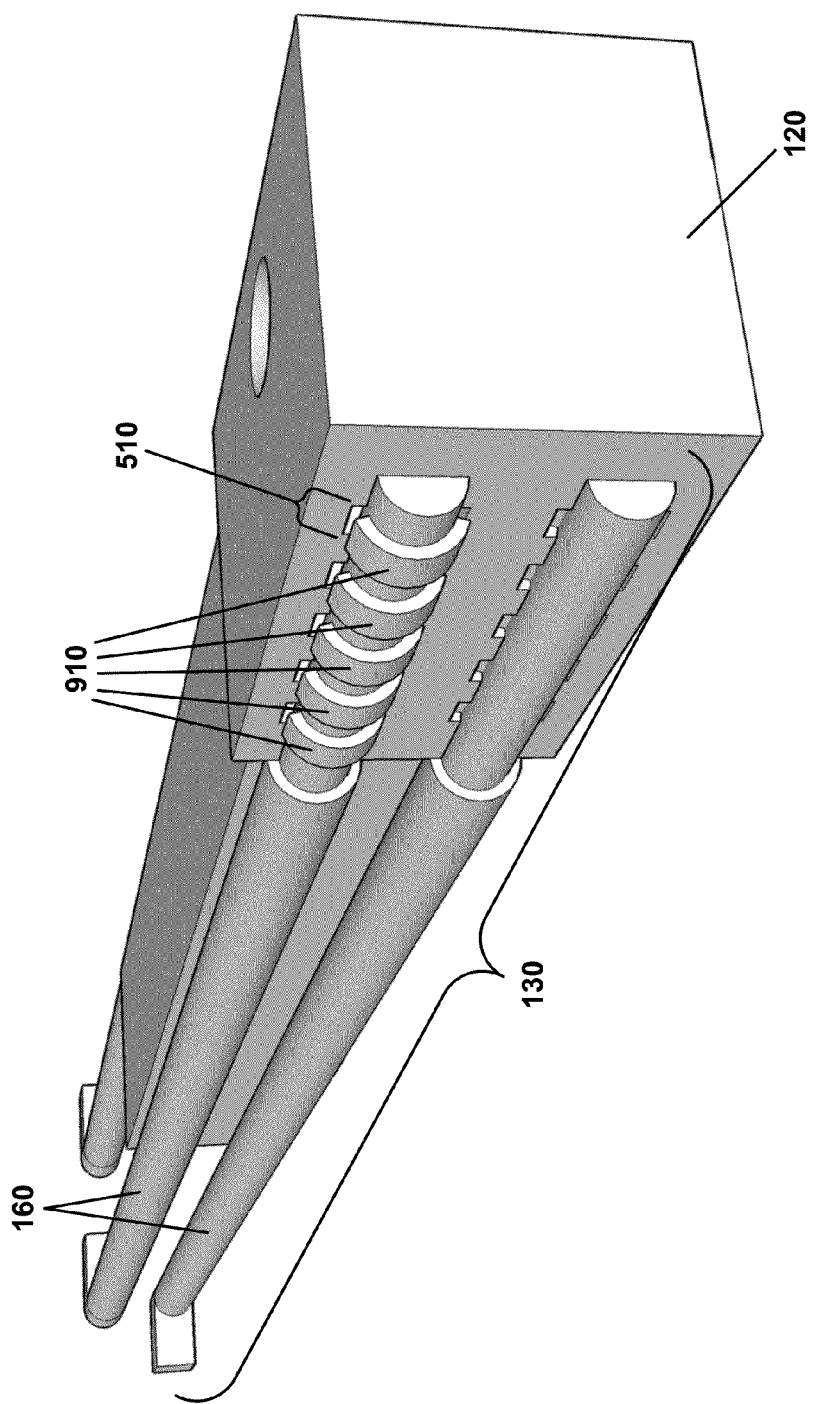
Figure 10C:
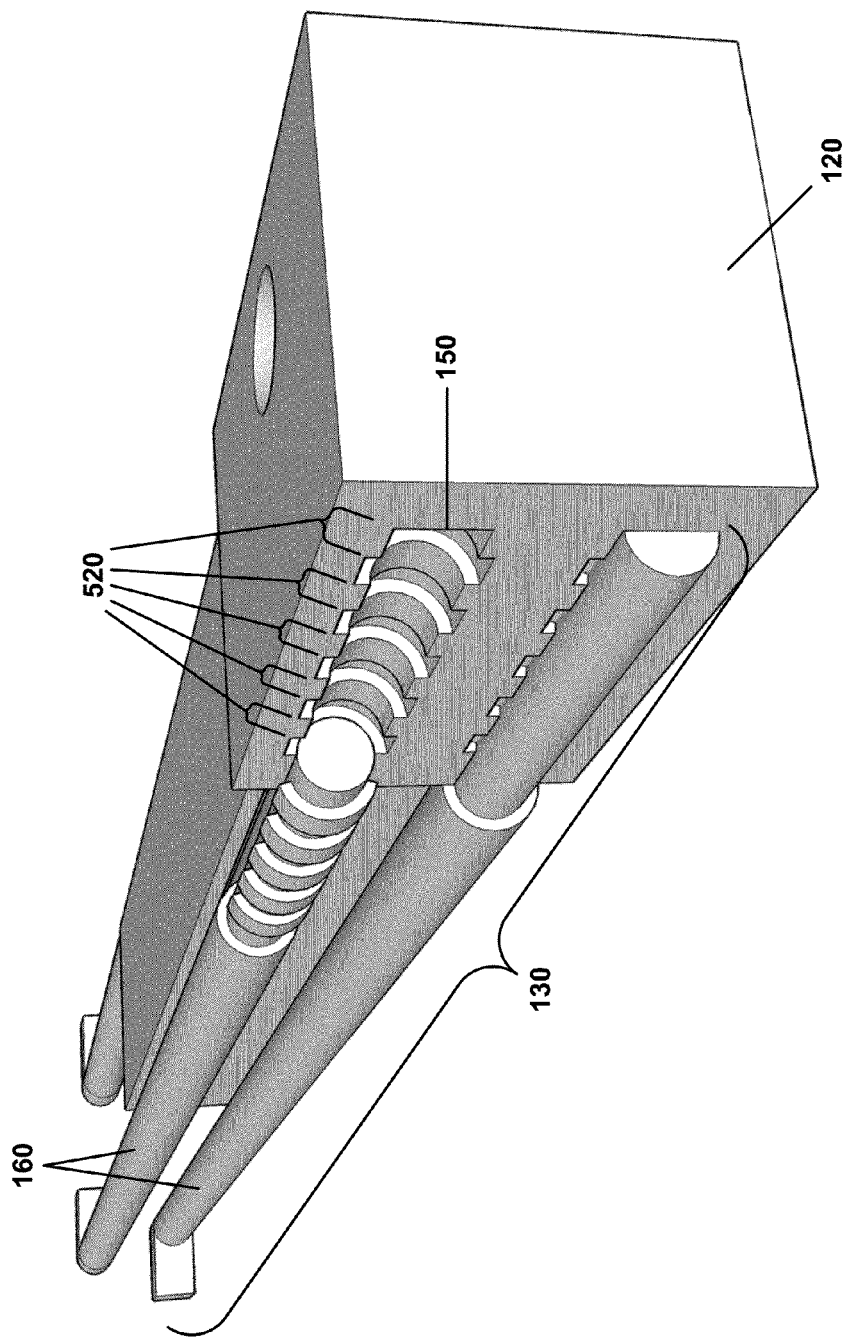

FIGS. 10A-10C step through an example of the process of controllably detaching the delivery mechanism 130 from the fusion member 120 once the delivery mechanism is no longer needed. FIG. 10A shows the initial configuration of two retention rods 160 of the delivery mechanism 130 fully coupled with two sets of retention grooves of the fusion member 120. In this figure, the retention rod 160 is fully coupled with retention grooves of the fusion member 120. In this configuration, the delivery rod 160 and delivery housing (e.g., the delivery mechanism 130) is tightly coupled with the fusion member 120. This configuration allows the fusion member 120 to be delivered between adjacent vertebral bodies. After the fusion member 120 has been delivered, a medical practitioner determines (e.g., by viewing x-ray images of the patient) whether the fusion member is in the correct position. If a determination is made that fusion member is not in the correct position between two vertebral bodies, the delivery mechanism can be used to reposition the fusion member to the desired location. When the medical practitioner determines that the fusion member is placed at the desired position between two vertebral bodies, and anchoring members have affixed the fusion member to the vertebral bodies, the retention mechanism can be used to controllably detach the delivery mechanism 130 from the fusion member 120. The controllable detachment of the delivery mechanism from the fusion member is initiated by the uncoupling of each retention rod from each set of retention grooves.

FIG. 10B shows a single retention rod 160 partially uncoupled from the retention grooves of the fusion member. In this configuration, the retention rod 160 is rotated 180 degrees so that the retention teeth 910 are disengaged from the subset of larger retention grooves 510. This configuration allows the retention rod 160 to be withdrawn from the retention grooves of the fusion member.

FIG. 10C shows the distal end of the shaft of the retention rod 160 after the shaft has been pulled away from the fusion member so that it is barely in contact with the subset of smaller retention grooves 520 (i.e., it has been removed from all but the last smaller retention groove). Once the shaft of the retention rod has been withdrawn from the retention grooves and from the fusion member, the process can be repeated to uncouple the remaining retention rods from the fusion member. When all of the retention rods have been uncoupled from the fusion member, the delivery mechanism can be detached from the fusion member and removed from the patient.

Figure 11:
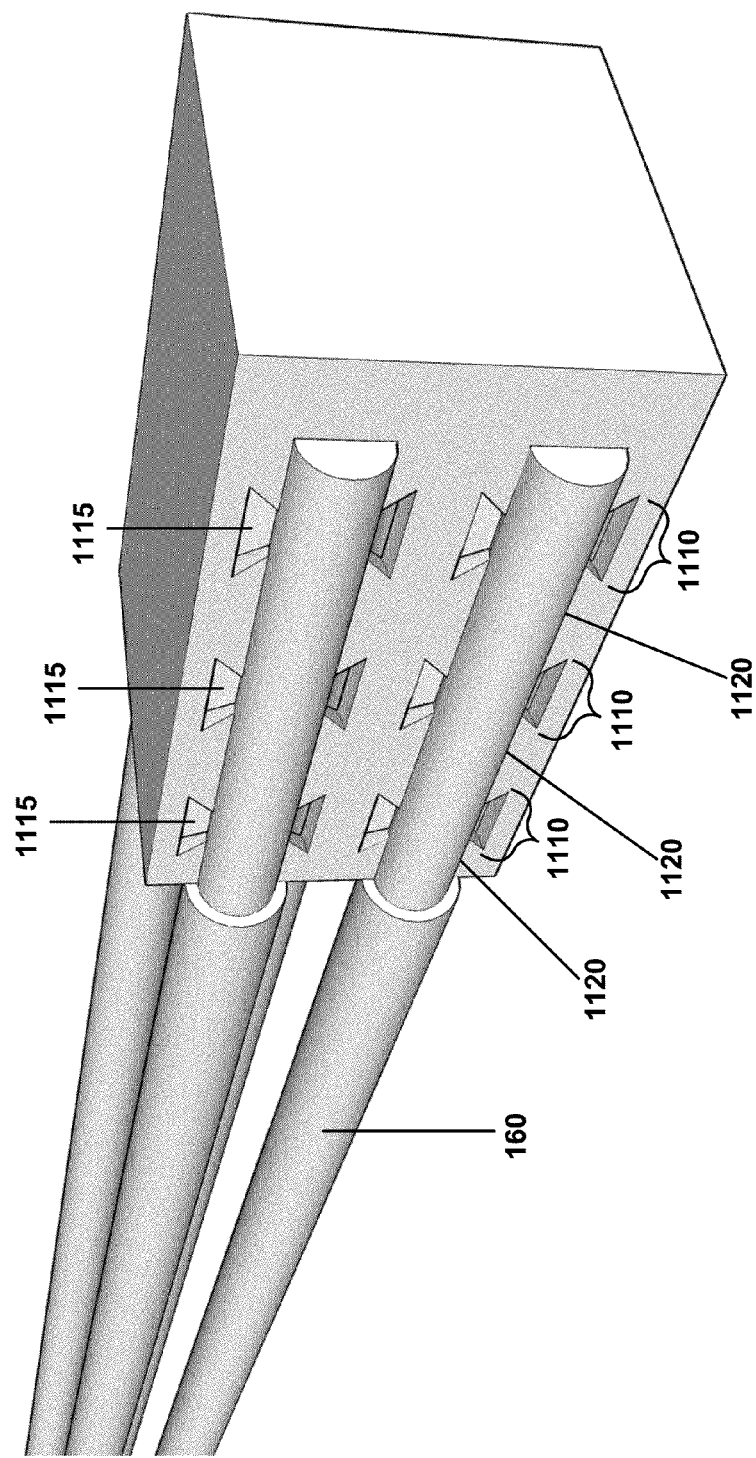
FIG. 11 illustrates a detailed view of the retention rod teeth coupled with the retention groove.
Figure 12:
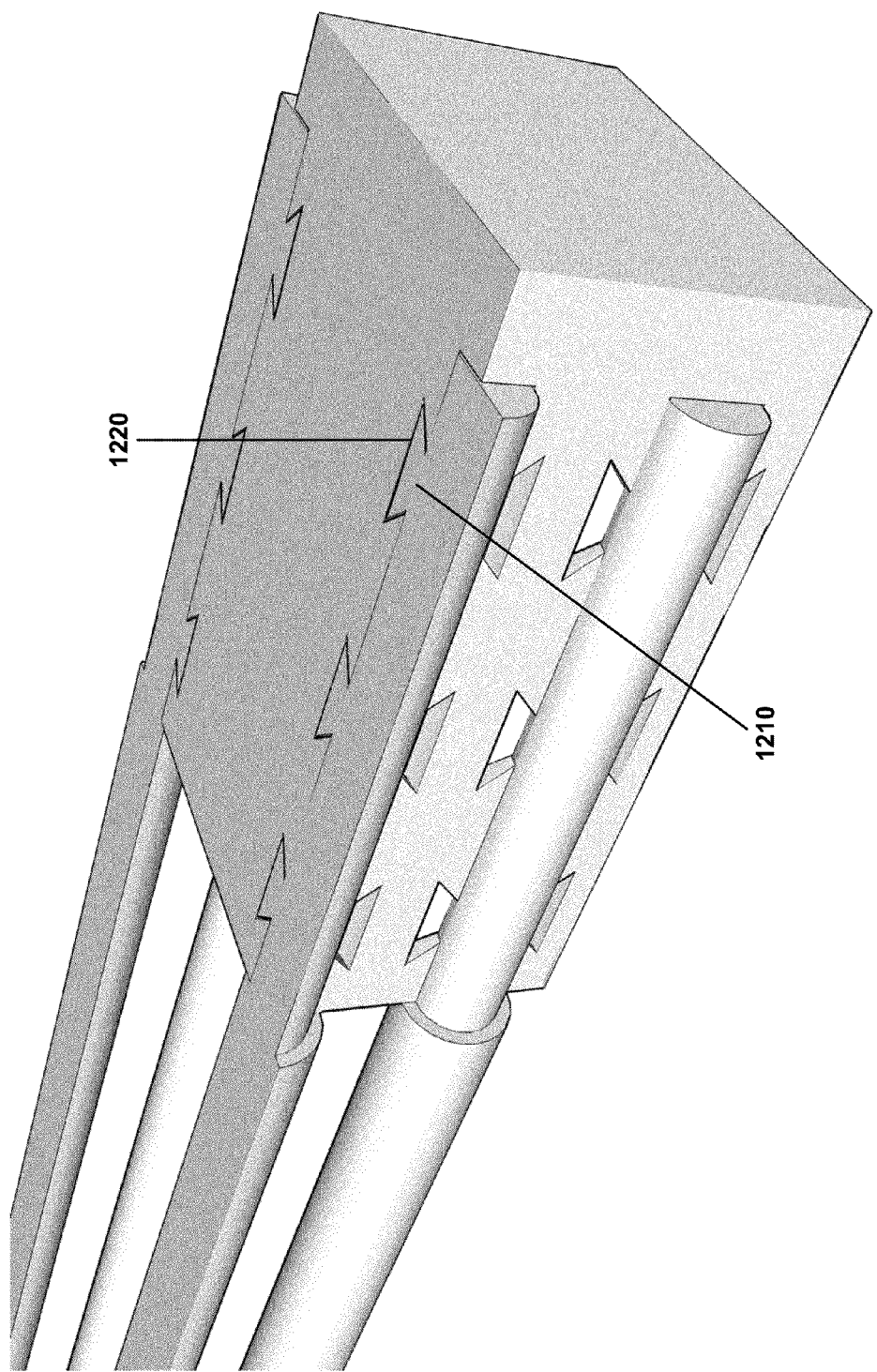
FIG. 12 illustrates a cross-section of the retention rod coupled with the retention groove.

FIGS. 11-12 illustrate another example of the retention grove and teeth structures of some embodiments. In this example, the retention teeth 1115 encompass less than 180 degrees of the retention rod shaft. This facilitates clearance between the retention teeth 1115 and the larger-diameter retention grooves 1110 when uncoupling the retention teeth 1115 from these grooves 1110 and when withdrawing the retention rod 160 away from the fusion member and out of the smaller-diameter retention grooves 1120. This example also shows the flared shape of the subset of larger retention grooves 1110. The flared shape of the retention grooves 1110 match the flared shape of the retention teeth 1115 in order to secure the retention teeth 1115 to the retention grooves 1110.

FIG. 12 illustrates a cross-section of the retention teeth 1115 fully coupled with the larger-diameter retention grooves 1110 to show the flared shape of the retention teeth. The width of the retention teeth increases as the distance increases from its base 1210 (i.e., where the retention teeth 1115 attach to the retention rod 160). The tip 1220 of each retention tooth has the largest width while the base 1210 of each retention tooth has the smallest width. This flared shape prevents any movement of the retention rod along the plane of the x, y, or z axis (i.e., prevents any horizontal or vertical movement, including the outward lateral movement of the retention rod from the fusion member) when the teeth of the retention rod are fully coupled with the larger-diameter retention grooves.

Figure 13:
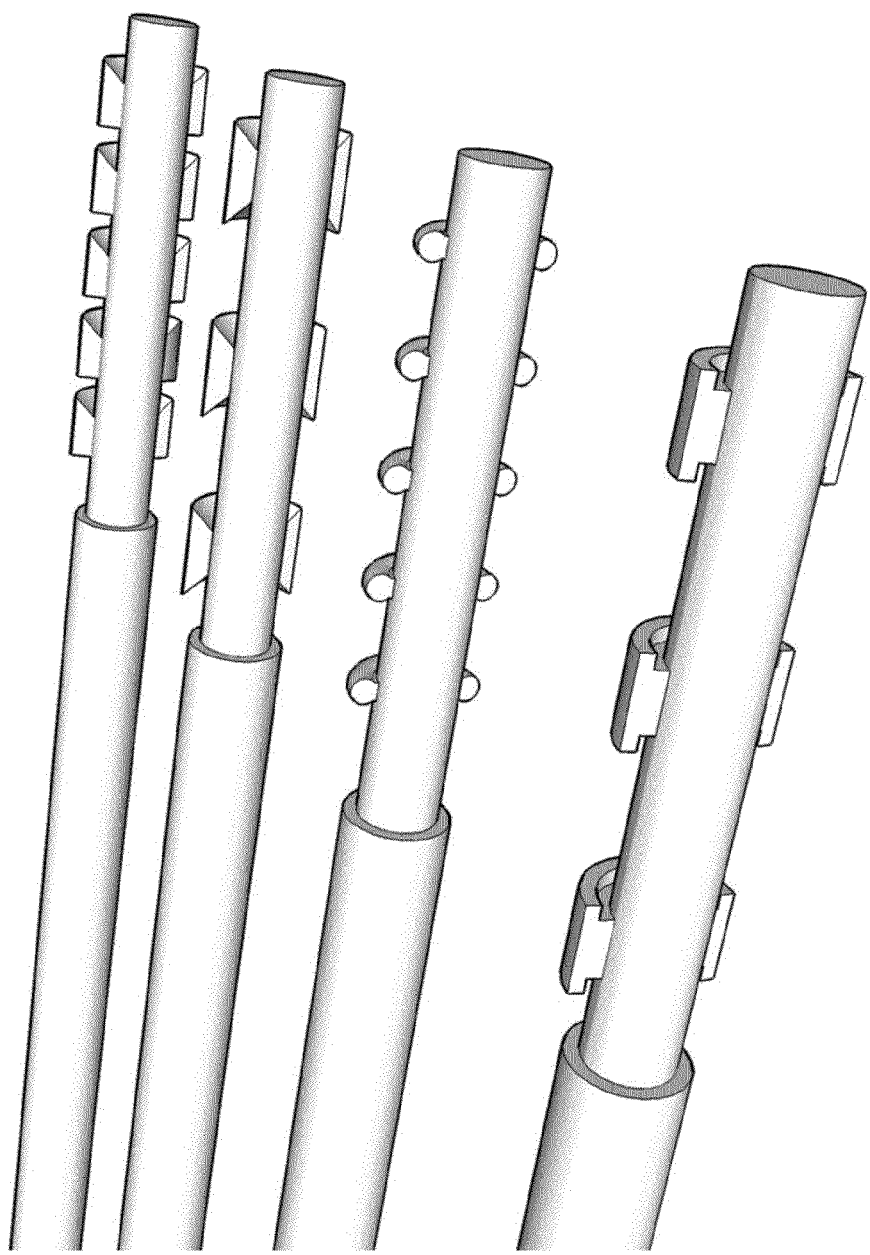
FIG. 13 shows alternative embodiments of retention teeth of the retention rods.

One of ordinary skill in the art will realize that even more alternative structures can be used for the retention groove and teeth structures than those illustrated in FIGS. 8-12. For instance, FIG. 13 illustrates a number of other teeth structures that are used in some embodiments.

Moreover, one of ordinary skill in the art will also realize that different configurations and different numbers of retention teeth can be utilized to affix the delivery mechanism to the fusion member. In some embodiments, the retention teeth may be on the fusion member and the retention groove may be on the retention rod. Instead of, or in conjunction with, this tooth and groove approach, other embodiments of the invention can use other structures (e.g., other male/female structures, other structures such as expandable clasps that encapsulate the lateral edges of the fusion member, other structures such as a clamp, etc.) to affix the delivery mechanism to the fusion member.

As mentioned above, the delivery housing channels house and guide the anchoring mechanism to the proper location in the fusion member. Different embodiments have different housing channels for guiding the anchoring mechanism to the proper location in the fusion member. In some embodiments, a circular channel with a constant diameter throughout its entire length can guide the anchoring mechanism as shown in FIGS. 7A-7C. Other embodiments have channels of different shapes and sizes. One such alternative embodiment is a square or rectangular channel with increasing and decreasing diameter towards the distal end of the delivery housing as will be described in the next section in reference to FIG. 14.

C. Anchoring Mechanism

Different embodiments of the invention use different anchoring mechanisms. Some embodiments use an anchoring mechanism formed by three pieces—an anchoring/embedded member, an intervening member, and a driving/retractable member. In some embodiments, the anchoring/embedded member, intervening member, and the driving/retractable member couple with each other to form a unified needle.

Other embodiments use an anchoring mechanism formed by two pieces—an anchoring/embedded member and a driving/retractable member. In some embodiments, the anchoring/embedded member and the driving/retractable member couple with each other to form a unified needle. The different embodiments of the anchoring mechanism will now be described in detail below.

1. Pivoting Anchoring Mechanism with Intervening Member

Figure 14:
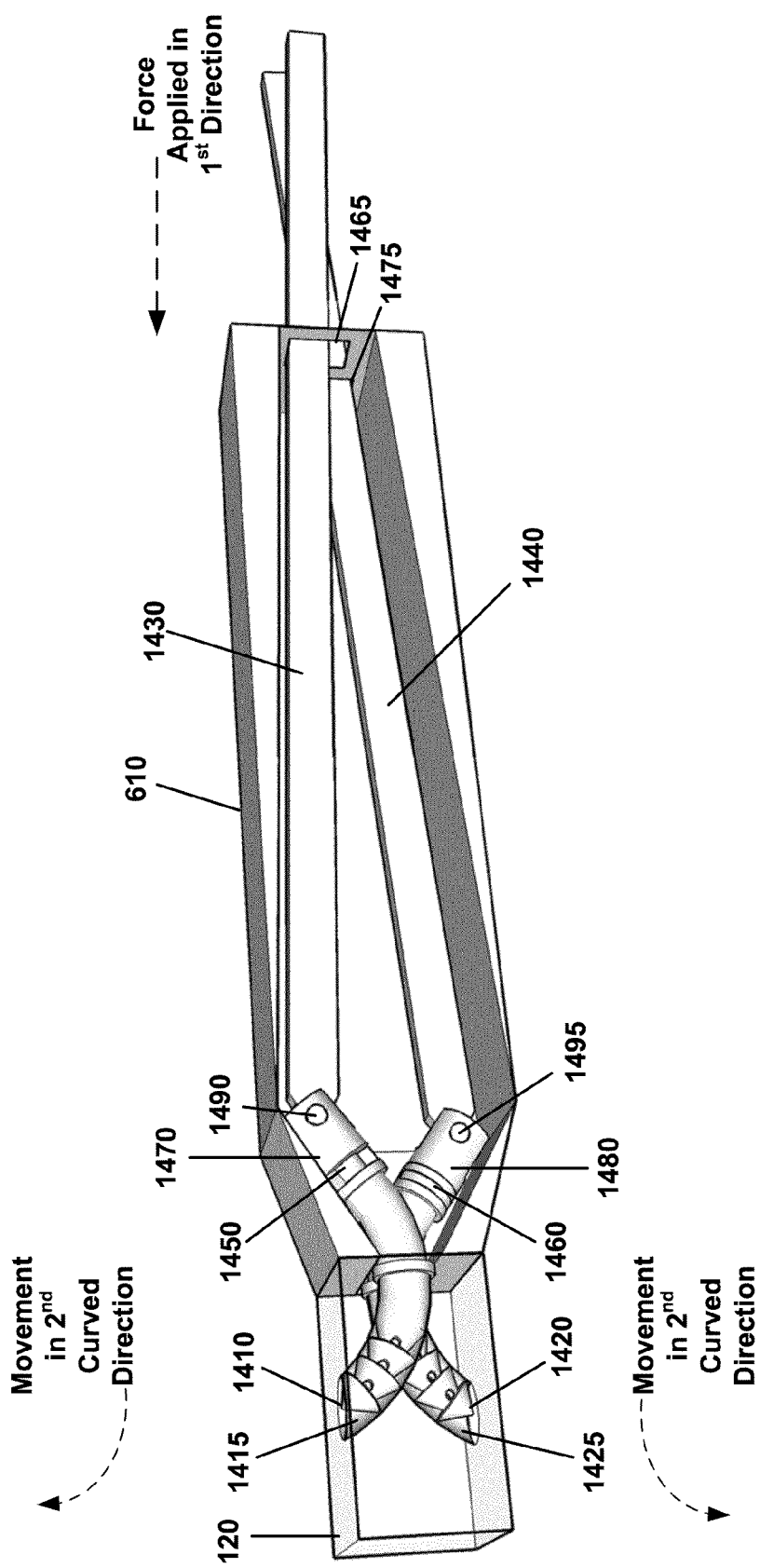
FIG. 14 shows two anchoring mechanisms in their initial configuration inside the channels of the delivery housing and fusion member.

As mentioned above, some embodiments use an anchoring mechanism formed by three pieces—an anchoring/embedded member, an intervening member, and a driving/retractable member. FIG. 14 shows one such embodiment of the anchoring mechanism. In this figure, two anchoring mechanisms are in their initial configuration inside the channels 1465 and 1475 of the delivery housing 610 and the fusion member 120. The anchoring mechanisms include (1) anchoring members 1410-1420 that affix the fusion member 120 to adjacent vertebral bodies, (2) intervening members 1470 and 1480, and (3) driving members 1430-1440 that advance the anchoring members 1410-1420 through the fusion member channels into the vertebral bodies. The driving members 1430-1440 include (1) shafts that advance the anchoring members 1410-1420 fully into the fusion member 120 or withdraw the anchoring members 1410-1420 from the fusion member 120 and (2) central lumens that provide a conduit for delivering polymers to the anchoring members 1410-1420. The intervening members 1470 and 1480 have central lumens (e.g., channels) as well. The central lumen in the driving members 1430-1440 and intervening members 1470 and 1480 align with the hollow channels (i.e., lumen) of their corresponding anchoring members 1410-1420 once the anchoring members 1410-1420 are advanced to their desired position inside the vertebral bodies.

Two delivery housing channels are shown in this figure. The first channel is shown with an opening 1465 on the proximal end of the delivery housing. The second channel is shown with the opening 1475 also on the proximal end of the delivery housing. Moreover, in FIG. 14, both channels are shown as transparent so that the second driving and anchoring members can be seen. However, these channels are similar to the channels 720 in FIGS. 7A-7C, except for their shape, which is further described below.

In some embodiments, the anchoring members are initially configured to be inserted in the entirety of the fusion member channels or in part of it, during the manufacturing of the fusion member delivery apparatus that contains these anchoring members. In other embodiments, they are initially configured to be fully contained in the housing of the delivery mechanism before they are inserted into the fusion member on their way for inserting into the vertebral bodies during an operation.

Figure 15:
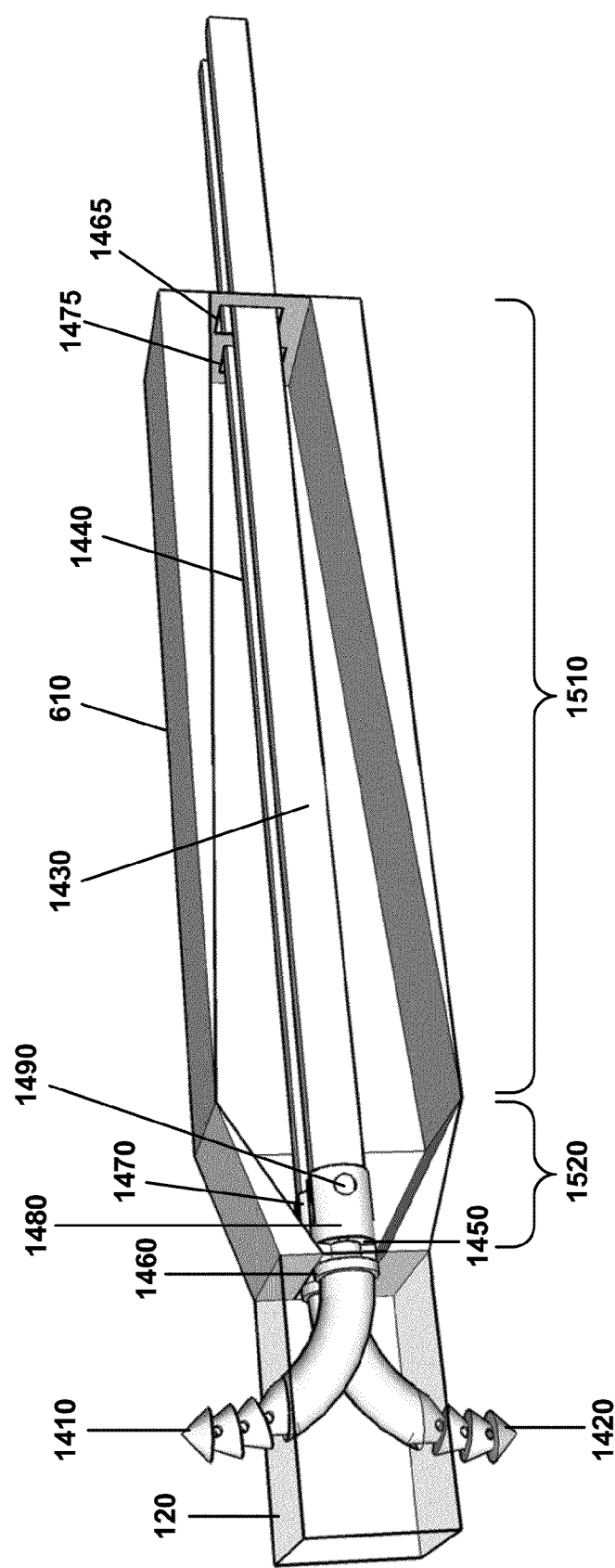
FIG. 15 shows two anchoring mechanisms in their final configuration after the anchoring members have been advanced into the vertebral bodies.

FIG. 15 shows the anchoring mechanisms in a configuration after the anchoring members 1410-1420 have been advanced into the vertebral bodies (which are not shown in this figure). When the anchoring mechanisms are fully advanced, the tips of the anchoring members 1410-1420 extend out of the fusion member channels and beyond the boundaries of the fusion member 120 into the marrow space of adjacent vertebral bodies. In this configuration; the anchoring members 1410-1420, the driving members 1430-1440, and intervening members 1470 and 1480 as well as their central lumens are aligned. This alignment provides an unobstructed pathway for the polymer to flow from the driving members 1430-1440 through the intervening members 1470 and 1480 and into the anchoring members 1410-1420.

FIGS. 14 and 15 also show an alternative embodiment of the delivery housing channels as mentioned above. As shown in these figures, the delivery housing channels 1465 and 1475 has two sections 1510 and 1520. A first section 1510 of the delivery housing channel has a diameter that increases towards the distal end of the delivery housing 610 (i.e., has increasing cross sections along the anchoring mechanism's path of the movement). In this section, the top side and bottom side of the delivery housing channel taper away from each other (i.e., the top side inclines away from the proximal opening while the bottom side declines away from the proximal opening). The increasing diameter provides sufficient space to allow the anchoring members 1410 and 1420 and the intervening members 1470 and 1480 to be at an angle with the driving members 1430 and 1440 as shown in its initial configuration. In addition, the increased diameter provides sufficient space to allow the anchoring members 1410 and 1420 and the intervening members 1470 and 1480 to pivot with the driving members 1430 and 1440.

A second section 1520 of the delivery housing channel has a diameter that decreases towards the distal end of the delivery housing 610 (i.e., has decreasing cross sections along the anchoring mechanism's path of movement). In this section, the top side and bottom side of the delivery housing channel taper toward each other (i.e., the top side declines towards the distal opening while the bottom side inclines towards the distal opening). The tapered (i.e. angled) top and bottom sides of this section (1) allow the anchoring member to pivot at an angle with the driving member and (2) guide the driving member towards the distal opening of the delivery housing channel. In some embodiments, each channel's longitudinal cross-section (i.e., cross-section that runs the length of the delivery housing) is in the shape of two trapezoids where the bases of the trapezoids are facing each other.

The transition of the anchoring mechanism from its initial configuration to its final configuration involves the tapered sides of the delivery housing channel's second section. As mentioned above, the tapered top and bottom sides of the second section allow the anchoring member to pivot with the driving member. While the anchoring mechanism is in its initial configuration illustrated in FIG. 14, force can be applied to the driving member in a first direction illustrated in FIG. 14 to advance the driving member towards the distal end of the delivery housing channel. When the driving member is advanced to the tapered sides of the delivery housing channel's second section, the tapered sides cause the anchoring member to pivot at an angle with the driving member. As the driving member is further advanced in this first direction, the distal end of the driving member travels down the tapered side toward the distal opening of the delivery housing. Since the anchoring member is at an angle with the driving member, the anchoring member is advanced in a second curvilinear direction that is at an angle with the first direction. The anchoring member is advanced through the curved fusion member channel and into the vertebral body. As the fusion member channel is curved, the path that the anchoring member travels is also curved. In other words, the anchoring member traverses in a second direction that is curved throughout its advancement through the fusion member channel. Accordingly, from the initial configuration of the anchoring mechanism to its final configuration, the tip of the anchoring member travels in a semi-circular path of movement.

Once the driving members 1430-1440 push the anchoring members 1410-1420 into the vertebral bodies, hardening material (e.g., PMMA, bone cement, or other hardening polymer) may be injected through the central lumen of the driving members, through the central lumen of the anchoring members, and into the marrow space of the vertebral bodies.

Figure 16:
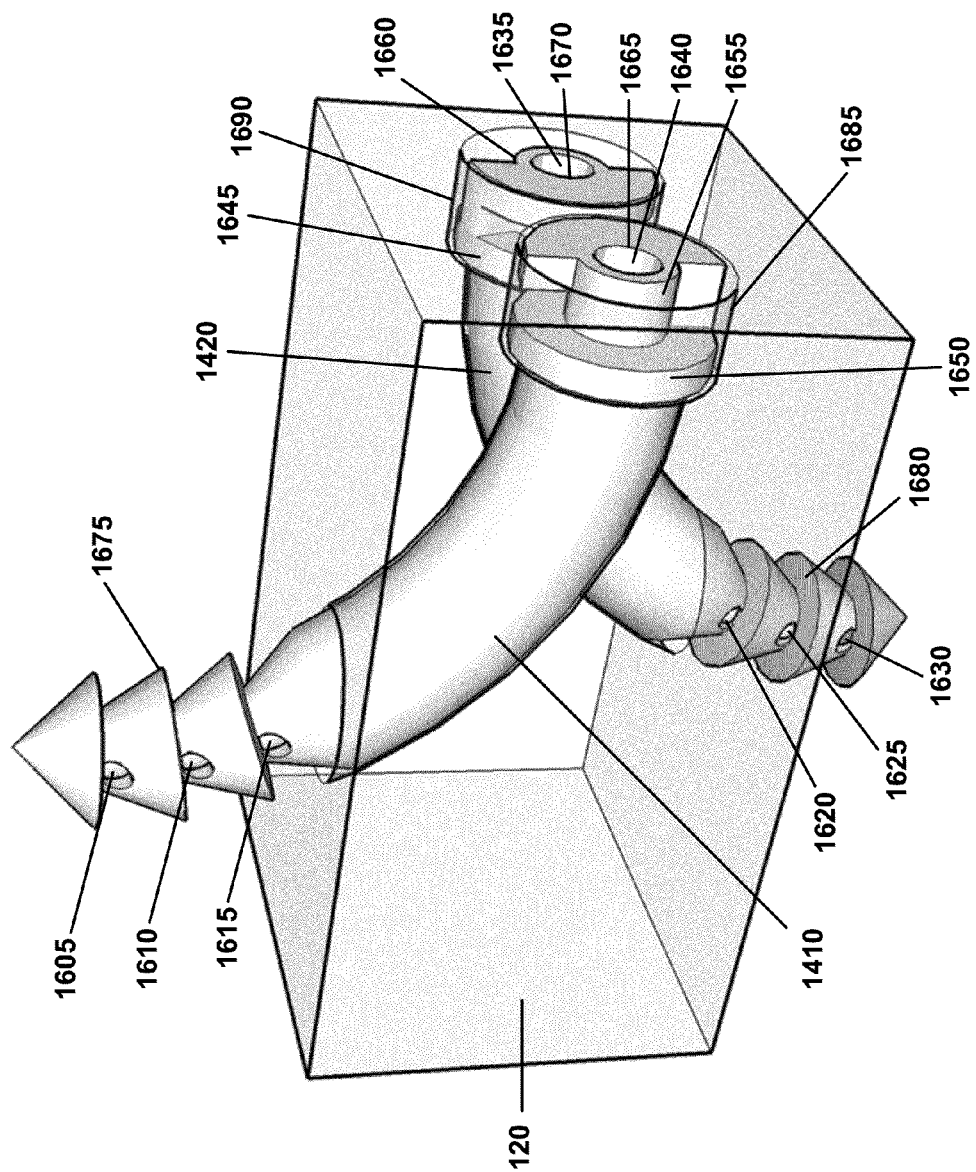
FIG. 16 illustrates a perspective view of two anchoring members inside the fusion member channels.

FIG. 16 illustrates a perspective view of the anchoring members 1410-1420. As shown in this figure, the anchoring members 1410-1420 have (1) several (e.g., three) distal perforations 1605-1630, (2) central lumens 1635-1640, (3) flanged bases 1645-1650, and (4) female coupling components 1655-1660 that couple with male coupling components of intervening or driving members, as further described below.

The distal perforations 1605-1630 of the anchoring members 1410-1420 communicate directly with the central lumens 1635-1640 of the anchoring member. These lumens 1635-1640 extend from the distal perforations 1605-1630 to the flanged bases 1645-1650 and their proximal openings 1665-1670. Polymer material can be injected through the central lumen of the driving and intervening members, into the openings 1665-1670 of the anchoring members 1410-1420, through the central lumens 1635-1640 of the anchoring members 1410-1420, and out of the perforations 1605-1630 to be delivered to the marrow space of vertebral bodies.

As shown in FIG. 16, the anchoring members 1410-1420 in some embodiments have surface contours 1675-1680 along their distal segment. In some embodiments, these surface contours may be angled teeth, back-facing retention ridges, or other surface contours. These surface contours assist in the retention of the anchoring members 1410-1420 within the vertebral bodies after injection and hardening of PMMA thereby further solidifying the anchoring of the fusion member 120 between the vertebral bodies.

Figure 17:
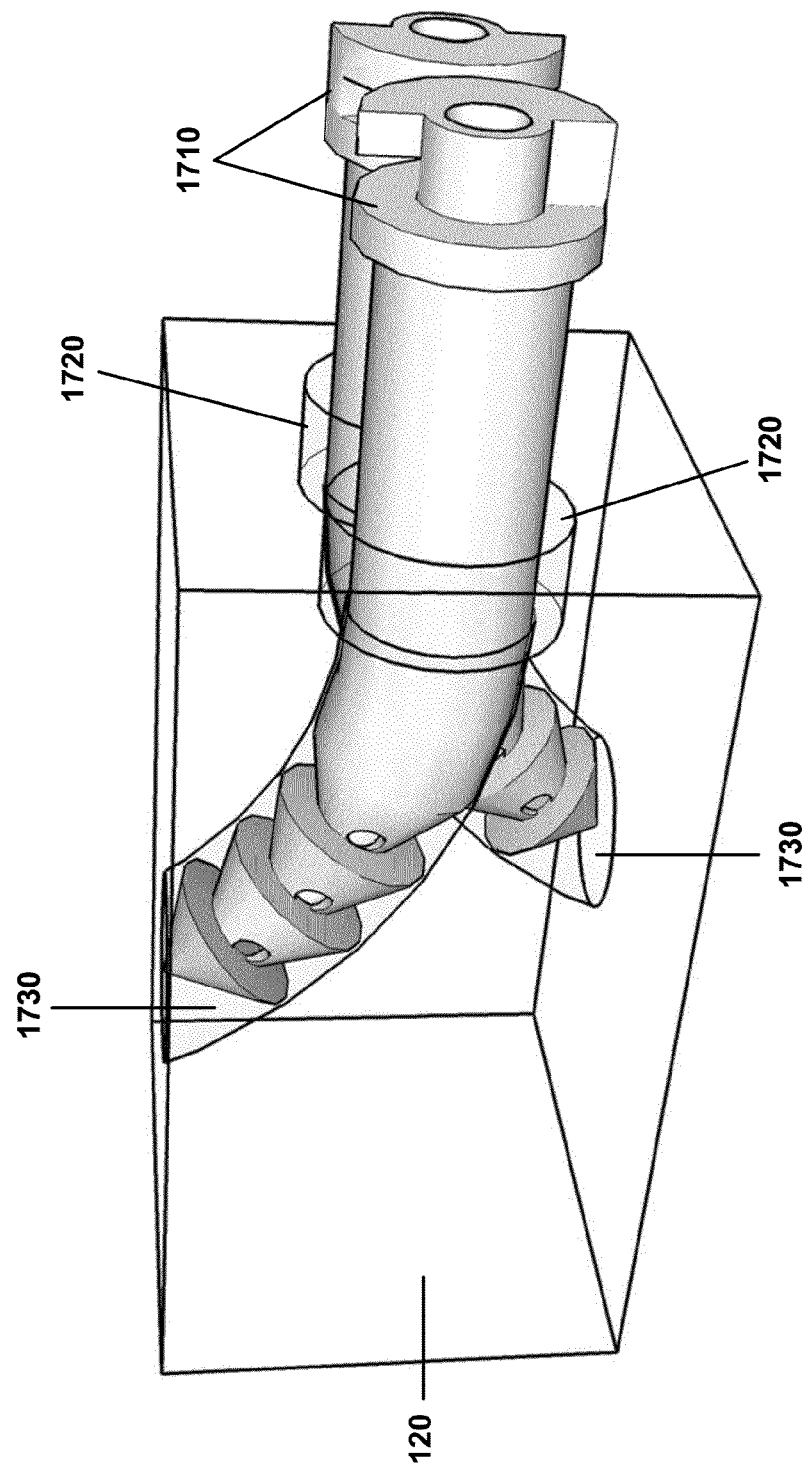
FIG. 17 depicts two anchoring members that have almost been fully advanced through the fusion member channels.

As shown in FIG. 16, flanges 1645-1650 at the base of the anchoring members 1410-1420 fit into recesses (i.e., flange cavity, anchoring member cavity, etc.) 1685-1690 of the fusion member channels locking the anchoring members 1410-1420 to the fusion member 120 once the anchoring members are fully advanced through the fusion member's channels. FIG. 17 illustrates the flange cavities 1720 at the proximal end of each fusion member channel 1730 that aid in affixing each anchoring member to the fusion member 120 when the anchoring members are fully advanced. In this figure, the anchoring members have not been fully advanced through the fusion member's channels to provide a clear illustration of fusion member's flange cavities 1720 and the flange bases 1710 of the anchoring members.

In some embodiments, the flange cavity's shape and the anchoring member's base shape may slightly differ. This shape difference still allows the anchoring member to be inserted into fusion member channel, but provides friction between the flange base of the anchoring member and the flange cavity of the fusion member channel, when the anchoring member has been fully advanced, to lock the anchoring member to the fusion member. In some embodiments, the flange cavity may have at least one tooth (not pictured) protruding toward the center of the cavity opening that locks the anchoring member to the fusion member when the anchoring member is fully advanced through the fusion member's channels. In addition, this tooth prevents the anchoring member from rotating when the driving member is uncoupled from the anchoring member, which will be described detail in FIGS. 24A-24B.

Figure 18:
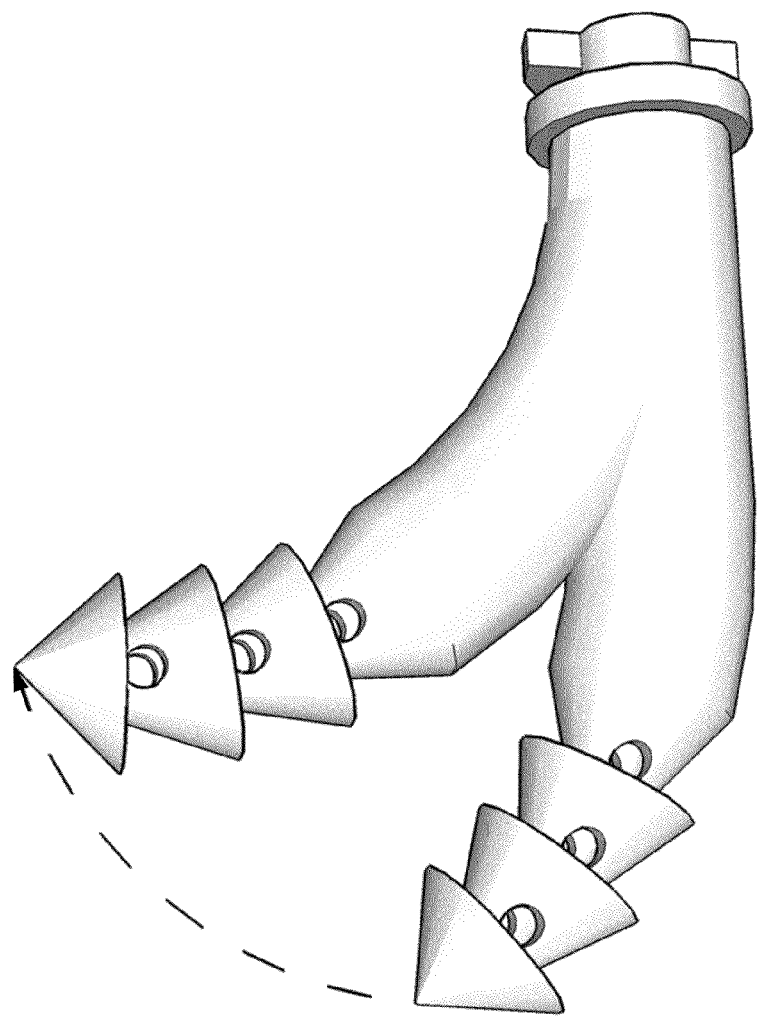
FIG. 18 depicts the flexibility of the anchoring member.

In some embodiments, the anchoring member can be composed of a material or a combination of materials that provides flexibility as shown in FIG. 18. To provide flexibility, the anchoring member can be composed of materials such as nitinol, stainless steel, titanium or other metals, metallic alloys, or high density polymers, carbon fiber, collagen or other biological materials, completely absorbable or partially absorbable material, or of a combination of these materials. In some embodiments, the tip of the anchoring member may be open or closed.

As mentioned above, some embodiments of the invention provide coupling mechanisms that couple the anchoring members directly to their corresponding driving members 1430-1440. As illustrated in FIG. 14, other embodiments include intervening members 1470-1480 that (1) couple the driving members 1430-1440 with the anchoring members 1410-1420 and (2) provide pivoting mechanisms 1490-1495 for enabling the anchoring members 1410-1420 and the intervening members 1470-1780 to pivot with the driving members 1430-1440. In some embodiments, the anchoring members, driving members, and intervening members all couple together to form a unified needle.

Figure 19:
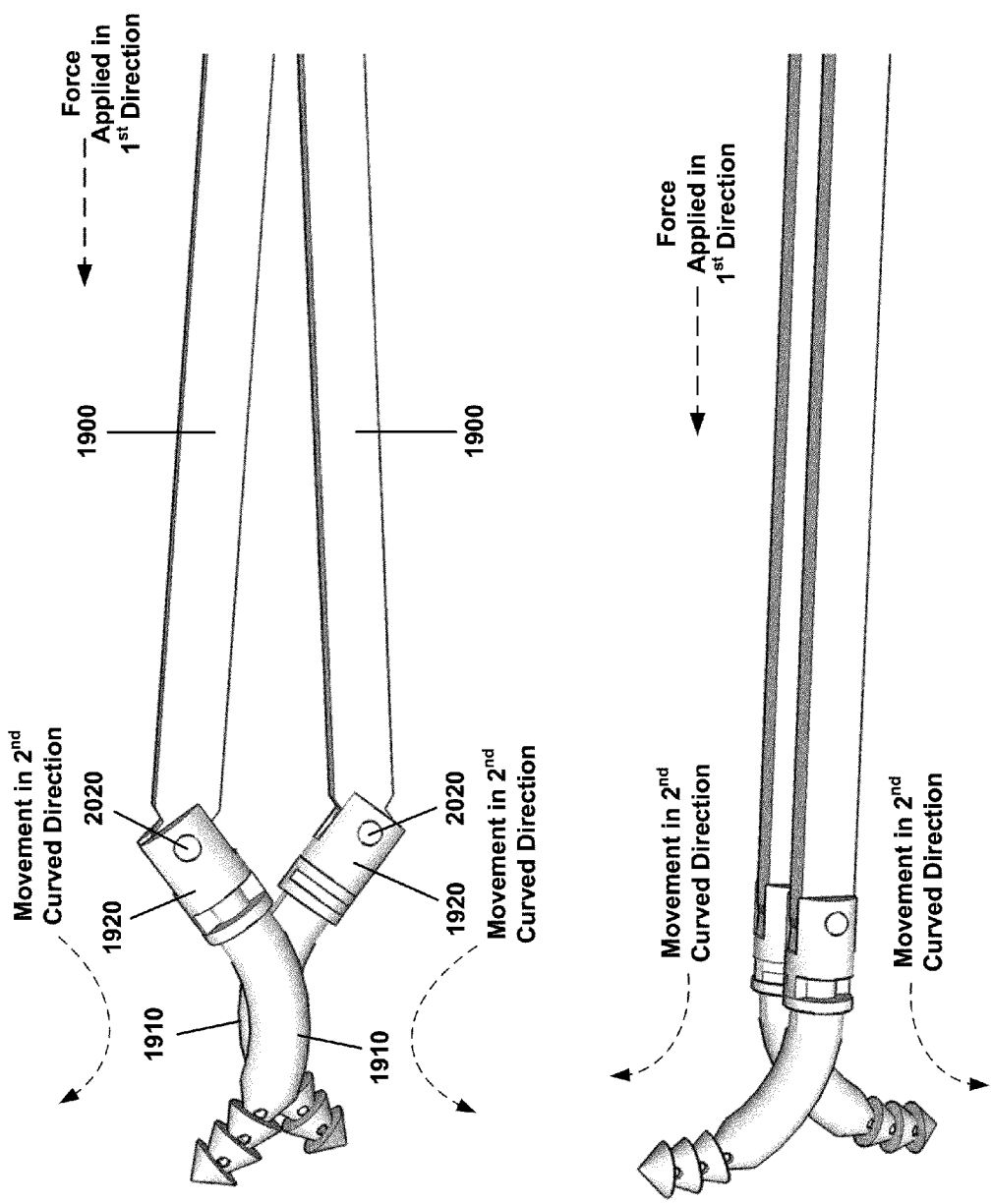
FIGS. 19-21 illustrate different views of the driving members and the anchoring members coupled and decoupled with the intervening members.
Figure 20:
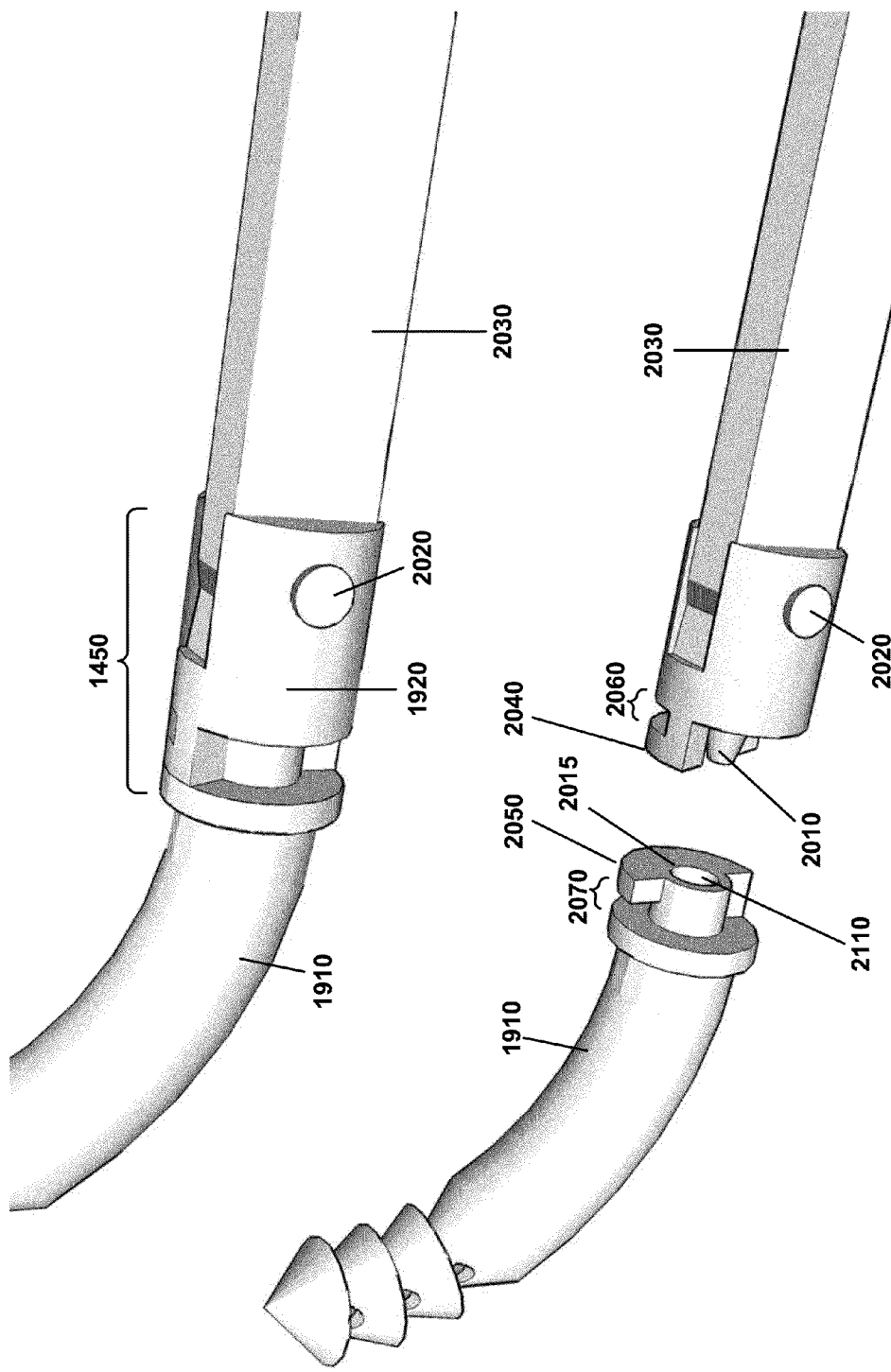
Figure 21:
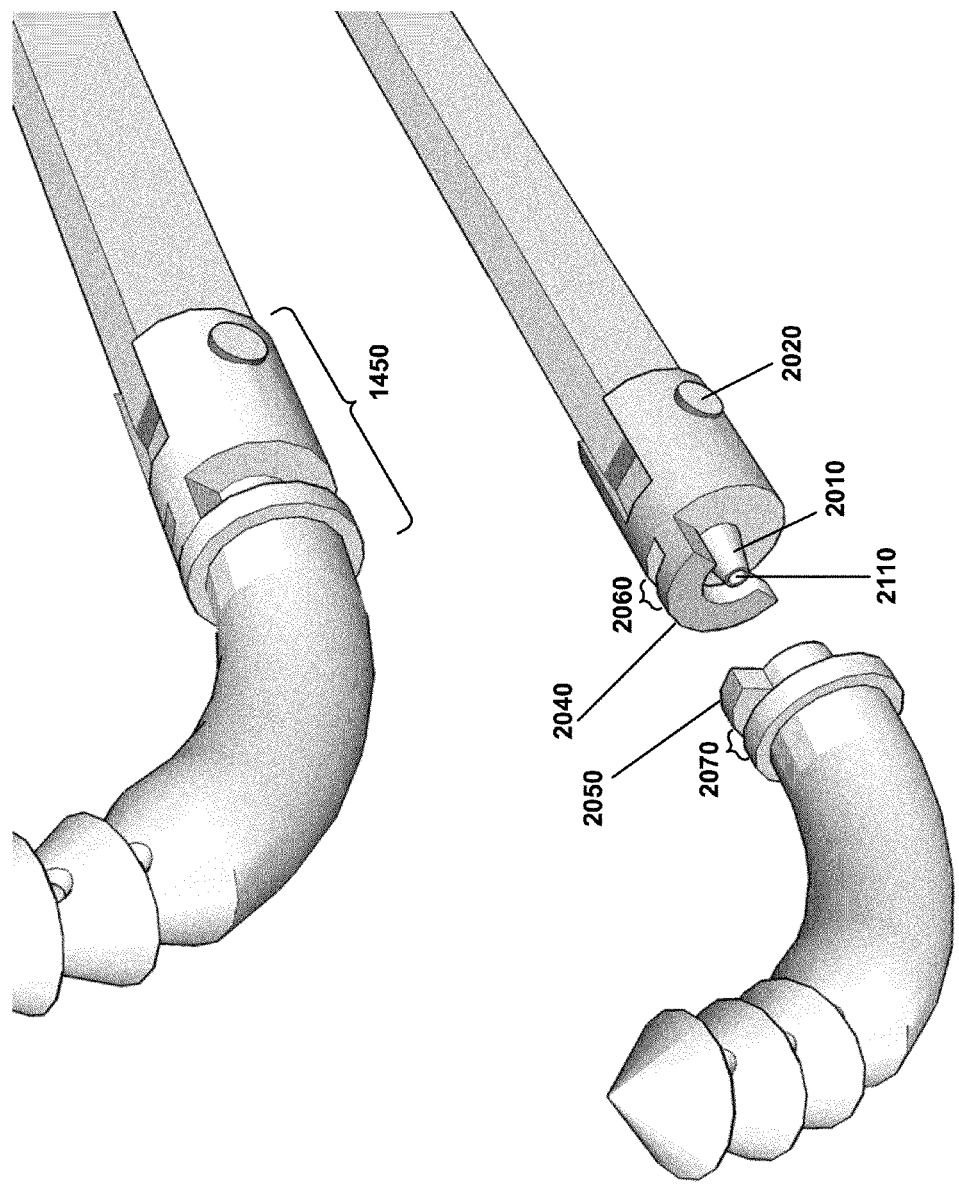

FIGS. 19-21 illustrate the driving members 1900 and the anchoring members 1910 coupled with the intervening members 1920. As shown in these figures, each driving member includes a shaft 2030 that can advance the anchoring member 1910 fully into the fusion member (not pictured) and can withdraw the anchoring member 1910 partially or fully from the fusion member. Each driving member also includes two pins 2020 that mate with two holes in an intervening member 1920 to enable the pivoting of the intervening member 1920 about the driving member 1900. Lastly, each driving member includes a central lumen 2110 (as shown in FIG. 21) that provides a conduit for delivering polymers to the anchoring member 1910. The central lumen extends the entire length of the driving member 1900, the intervening member 1920, and the anchoring member 1910.

FIGS. 20-21 show different views of the distal end of the driving member 1900 and the intervening member 1920 in relation to the anchoring member 1910. In these figures, the driving member 1900 and intervening member 1920 are shown in their coupled and decoupled configurations with the anchoring member 1910. The driving member 1900 and the intervening member 1920 couple via the coupling mechanism 1450. The coupling mechanism includes a male member 2010 located on the intervening member 1920 and a female member 2015 located on the anchoring member 1910. The male member 2010 includes a protruding stub encompassing the central lumen 2110 of the intervening member 1920. It also includes an arm 2040 and a slot 2060 behind the arm 2040. The female member 2015 includes an indentation that leads to the central lumen 2110 of the anchoring member 1910. It also includes an arm 2050 and a slot behind the arm 2070 that complements and rotatably couples with the slot 2060 and the arm 2040 of the male member 2010. To separate the coupling mechanism 1450, the intervening member 1920 may be rotated by rotating the driving member shaft 2030 until the interlocking arms 2040-2050 exit the slots 2060-2070 in which they were inserted, and the arms 2040 of the male member 2010 and arms 2050 of the female member 2015 clear each other, as further described below by reference to FIGS. 24A-24B.

Figure 22B:
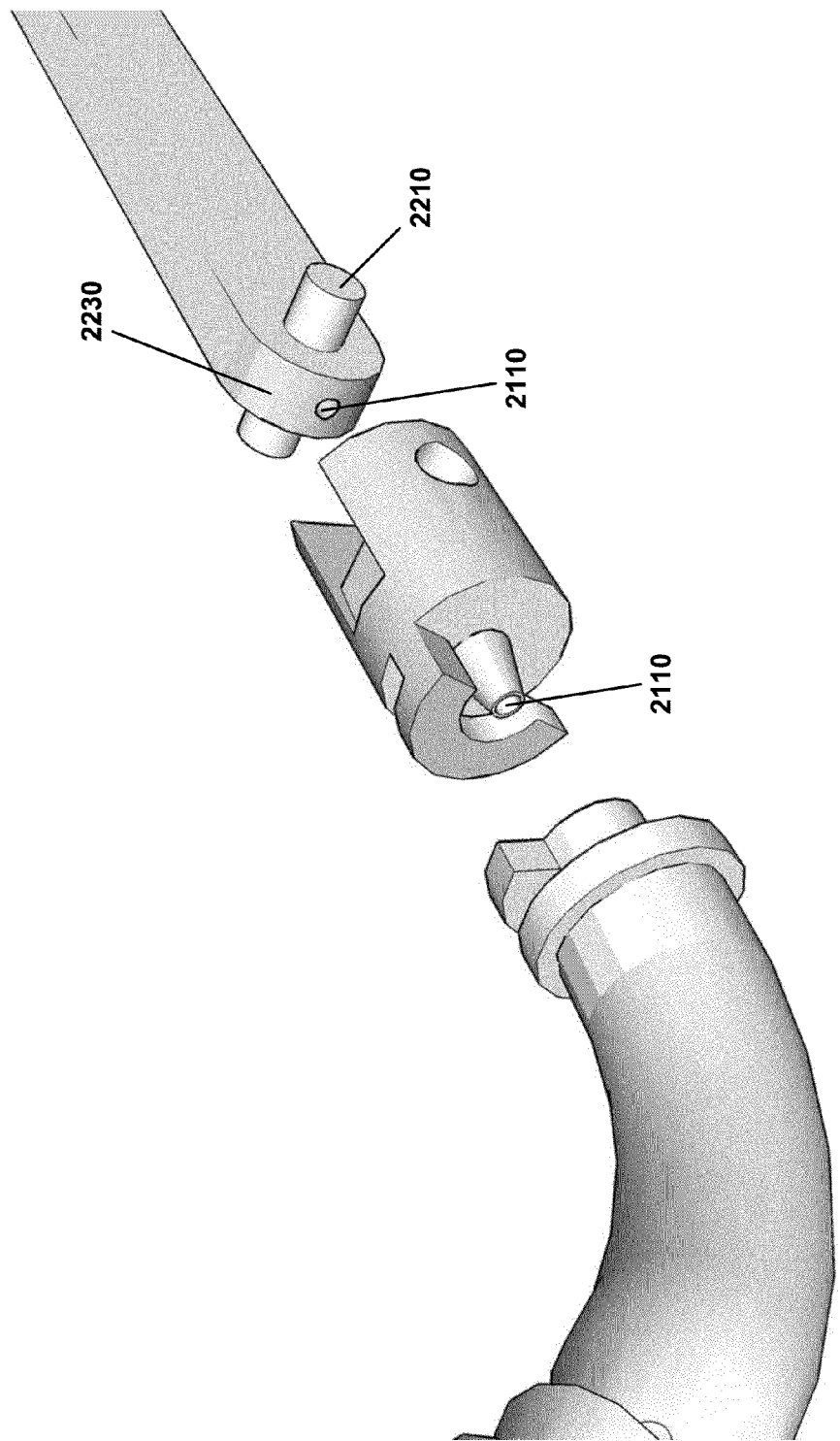

The intervening member 1920 also includes two holes that mate with the two pins of the driving member. As mentioned above, the mating allows the intervening member 1920 to pivot with the driving member 1900 and additionally couples the driving member 1900 with the intervening member 1920. FIGS. 22A-22B illustrate exploded views of the pivoting mechanism from different perspectives. As shown in these figures, the pivoting mechanism comprises protruding pegs (i.e., pins) 2210 on the distal end of the driving member shaft, and holes 2220 for engaging the pegs 2210. In some embodiments, the protruding pegs 2210, and the holes 2220 are round to allow the intervening member 1920 to pivot around the driving member 1900. In some embodiments, the distal end of the driving member shaft is rounded at the tip 2230, and fits into a rounded concave indentation 2240 of the intervening member 1920. This also facilitates the pivoting motion between the intervening member 1920 and the driving member 1900. The pivoting movement between the driving member 1900 and the intervening member 1920 facilitates the advancement of the anchoring members 1910 through the channels of the fusion member in a circular motion.

Once the anchoring member 1910 has been fully advanced through the fusion member channels and into the vertebral bodies, the pivoting mechanism aligns the driving members 1900, intervening members 1920, and the anchoring members 1910 as illustrated in FIG. 19. This alignment allows the central lumens 2110 of the driving members 1900, the intervening members 1920, and the anchoring members 1910 to align, providing an unobstructed pathway for the delivery of polymer through the driving members 1900, the intervening members 1920, and the anchoring members 1910 into the vertebral bodies.

2. Non-Pivoting Anchoring Mechanism

Figure 23A:
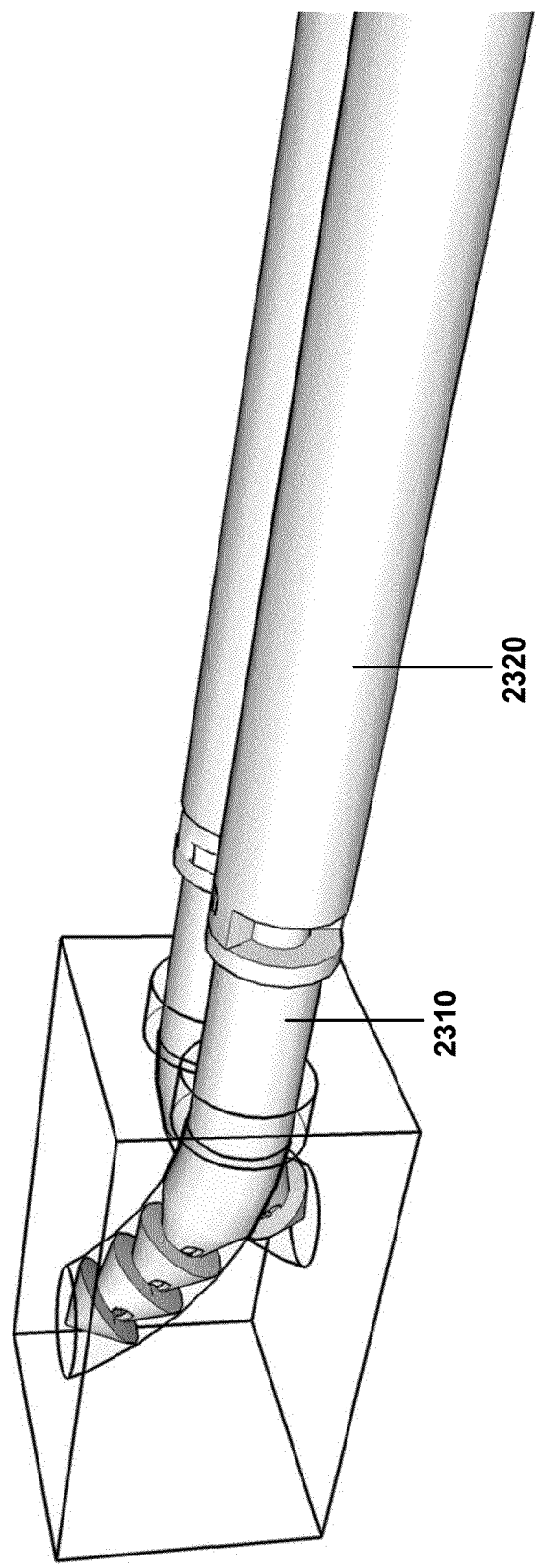
FIGS. 23A-23B shows the driving members connecting directly with the anchoring members (i.e., no intervening member).
Figure 23B:
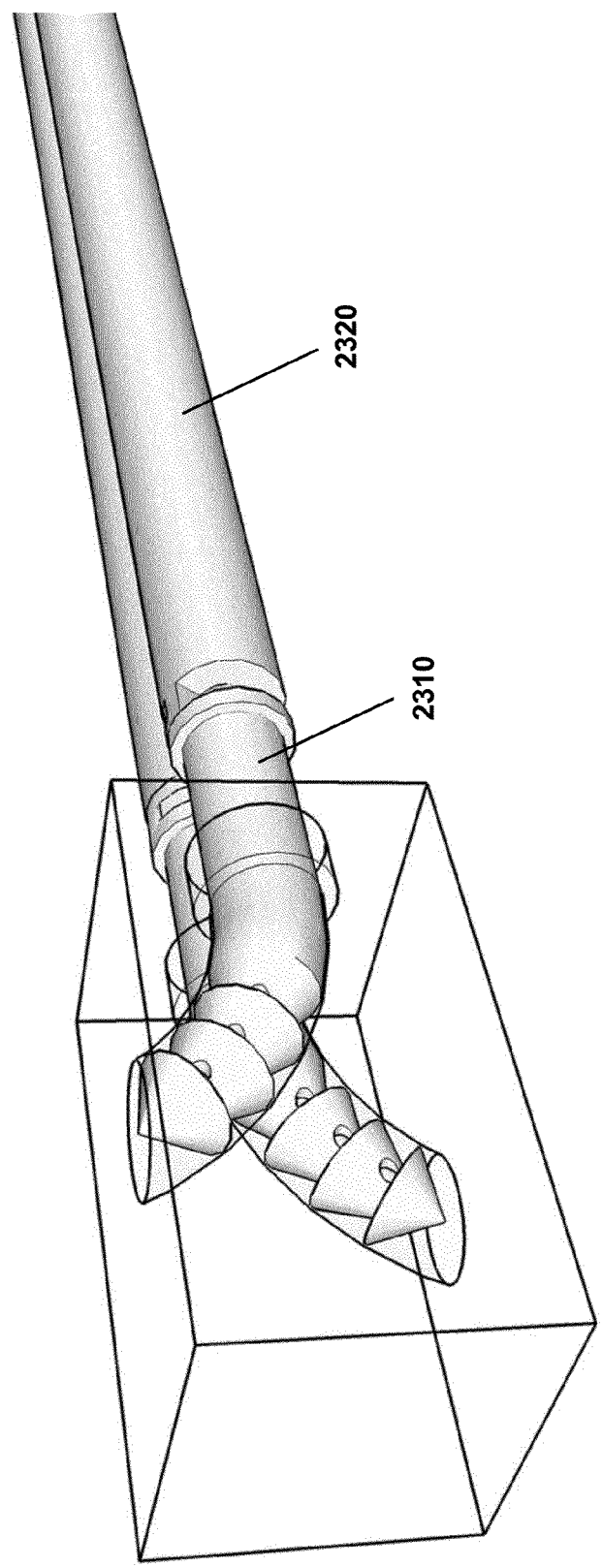

In some embodiments, the driving members 2320 connect directly to the anchoring members 2310 (i.e., no intervening member) as shown in FIGS. 23A-23B. When coupled together, the anchoring member and driving member form a unified entity, the anchoring needle. In some embodiments, the anchoring member is the embedded portion that is embedded in the vertebral bodies while the driving member is the retractable portion that is removed once the fusion member has been affixed to the vertebral bodies between which it is placed.

In the embodiment illustrated in FIGS. 23A-23B, the driving member's distal end includes the male member 2510 which directly couples with the female member 2520 of the anchoring member 2310 (the male member 2510 and female member 2520 are shown clearly in FIGS. 25A-25D). The male member 2510 of the coupling mechanism is directly integrated into the distal end of the driving member. The female member of the coupling mechanism is directly integrated into the proximal end of the anchoring member.

Figure 24A:
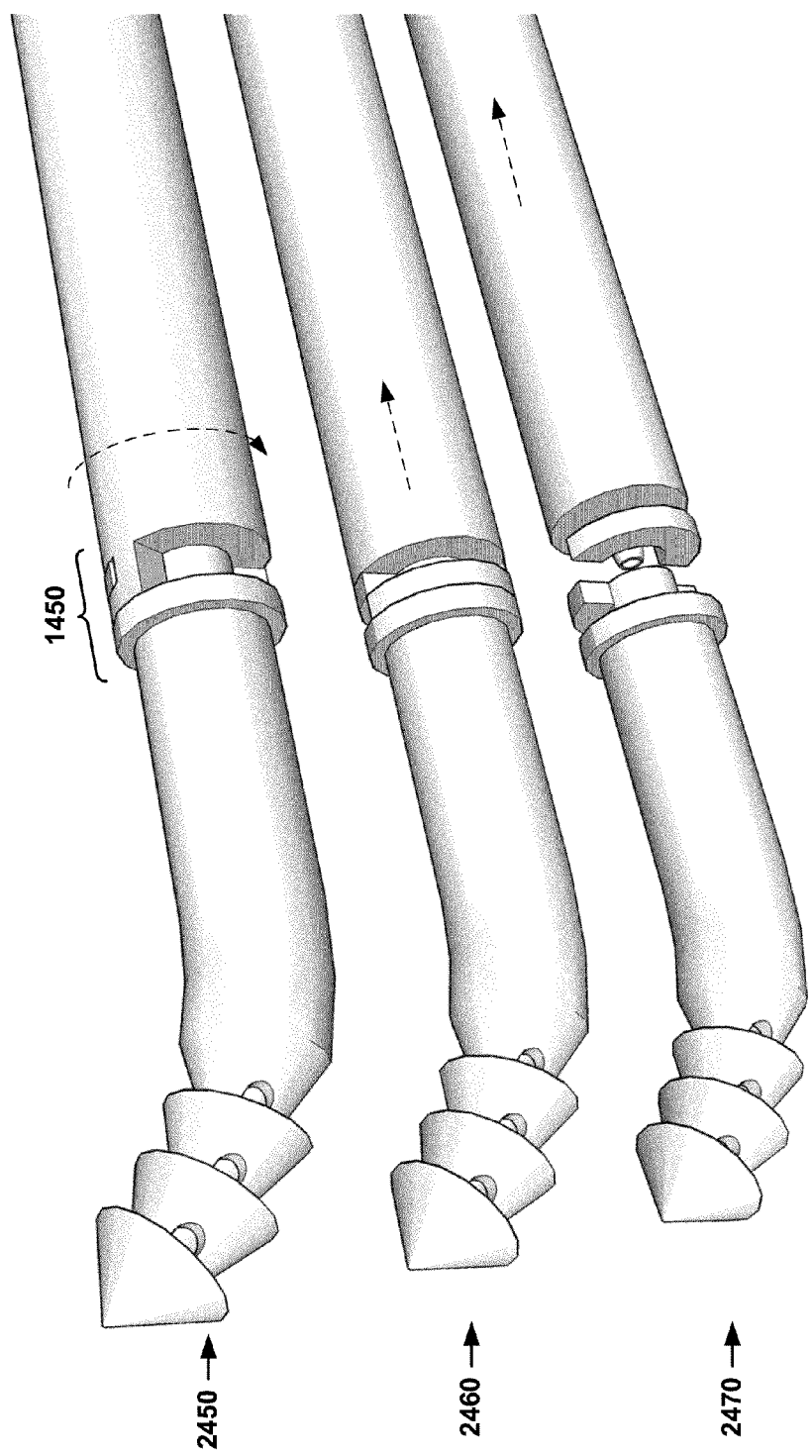
FIGS. 24A-24B shows different views and configurations of coupling mechanisms connected directly with the anchoring members and the driving members.
Figure 24B:
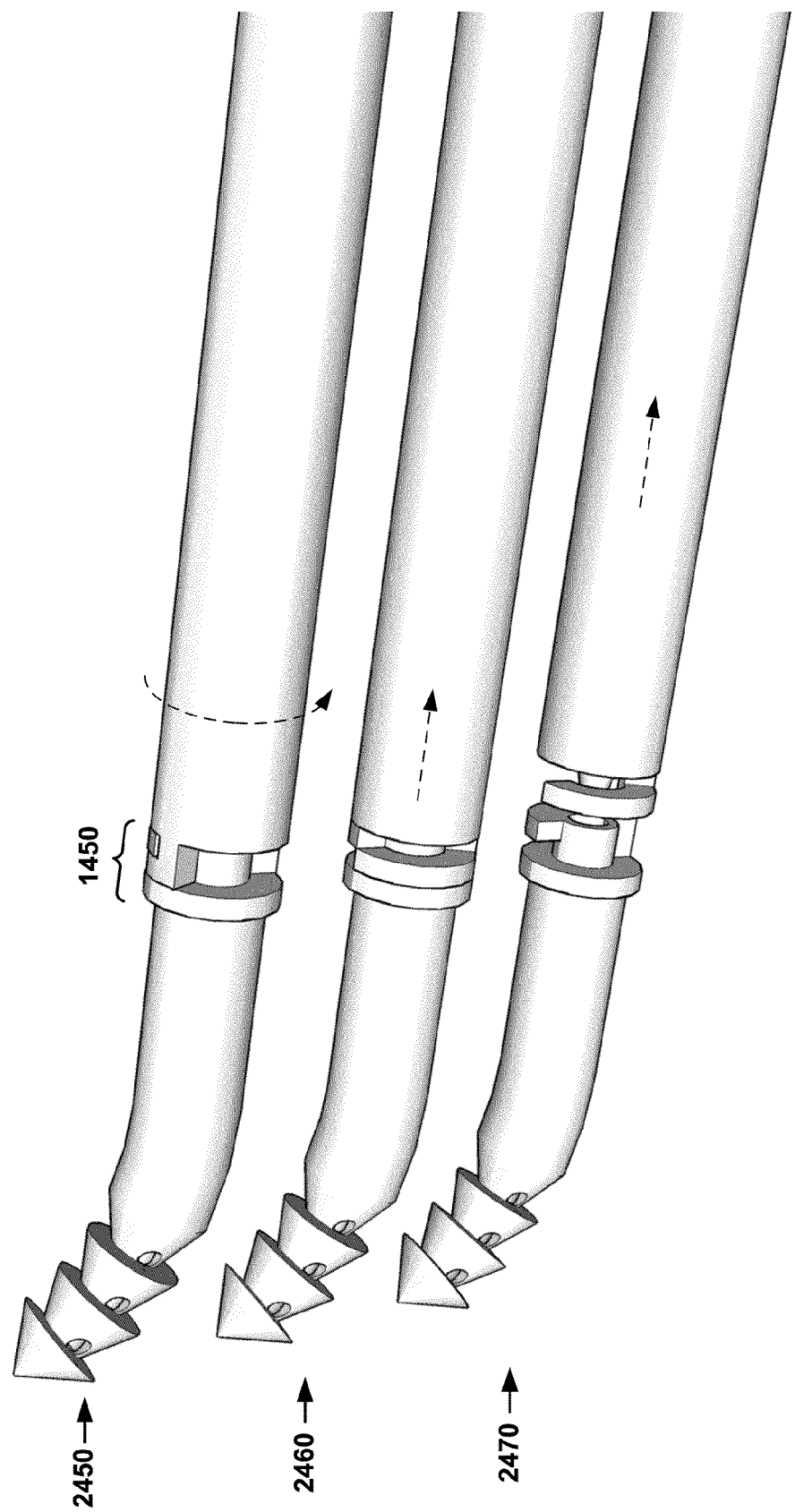
Figure 25A:
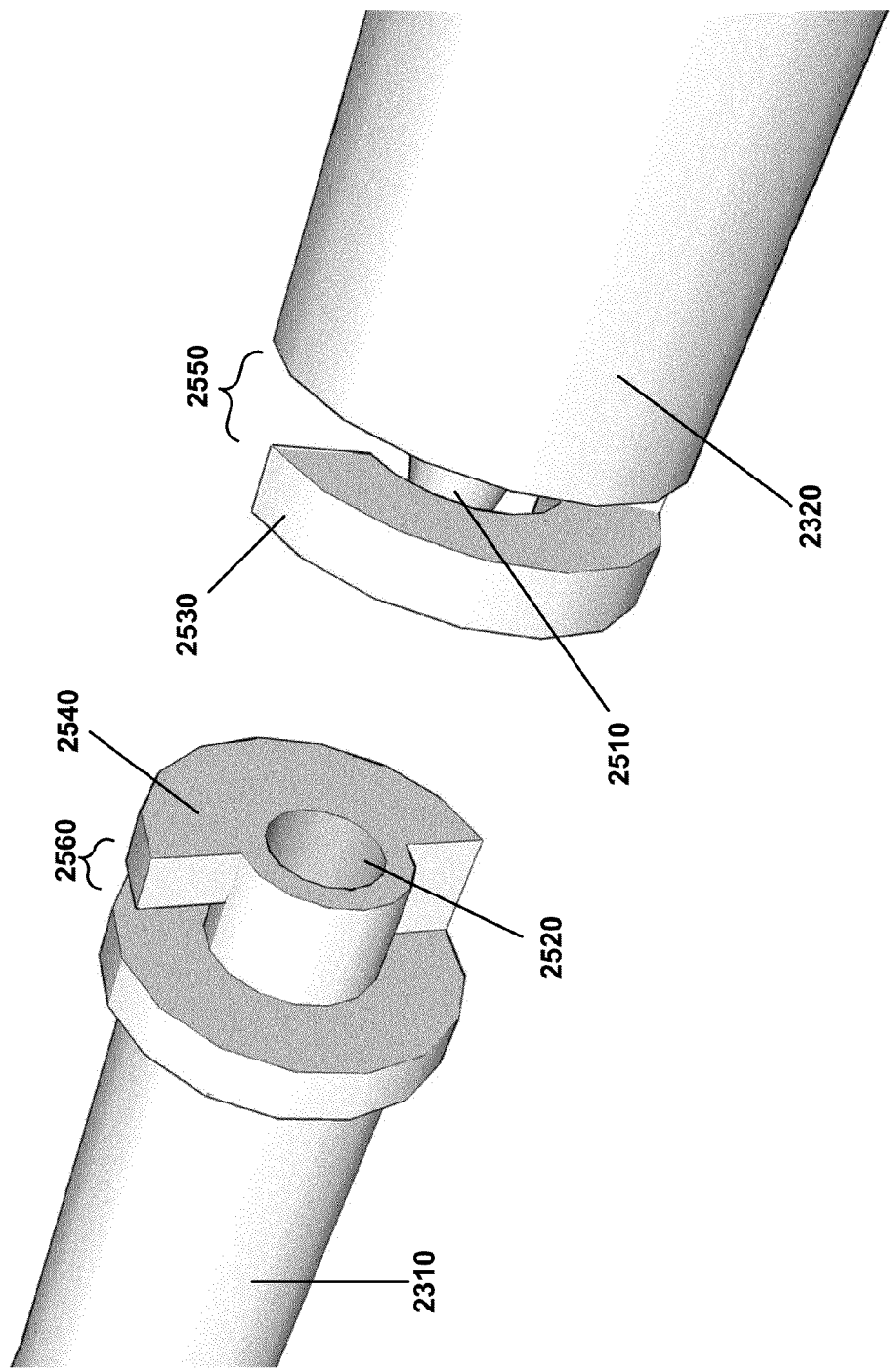
FIGS. 25A-25D provide detailed illustrations of the coupling mechanism.
Figure 25B:
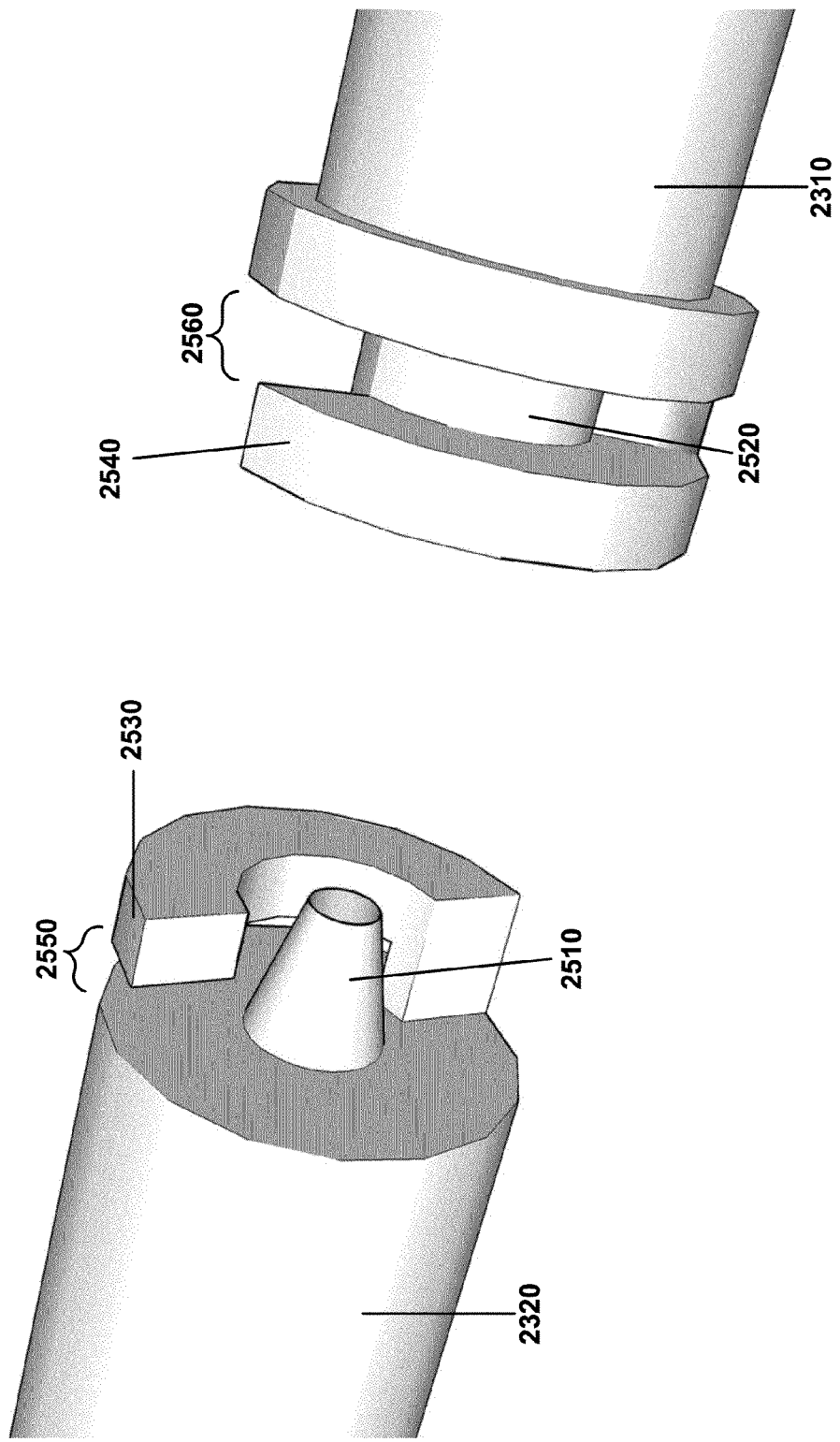
Figure 25C:
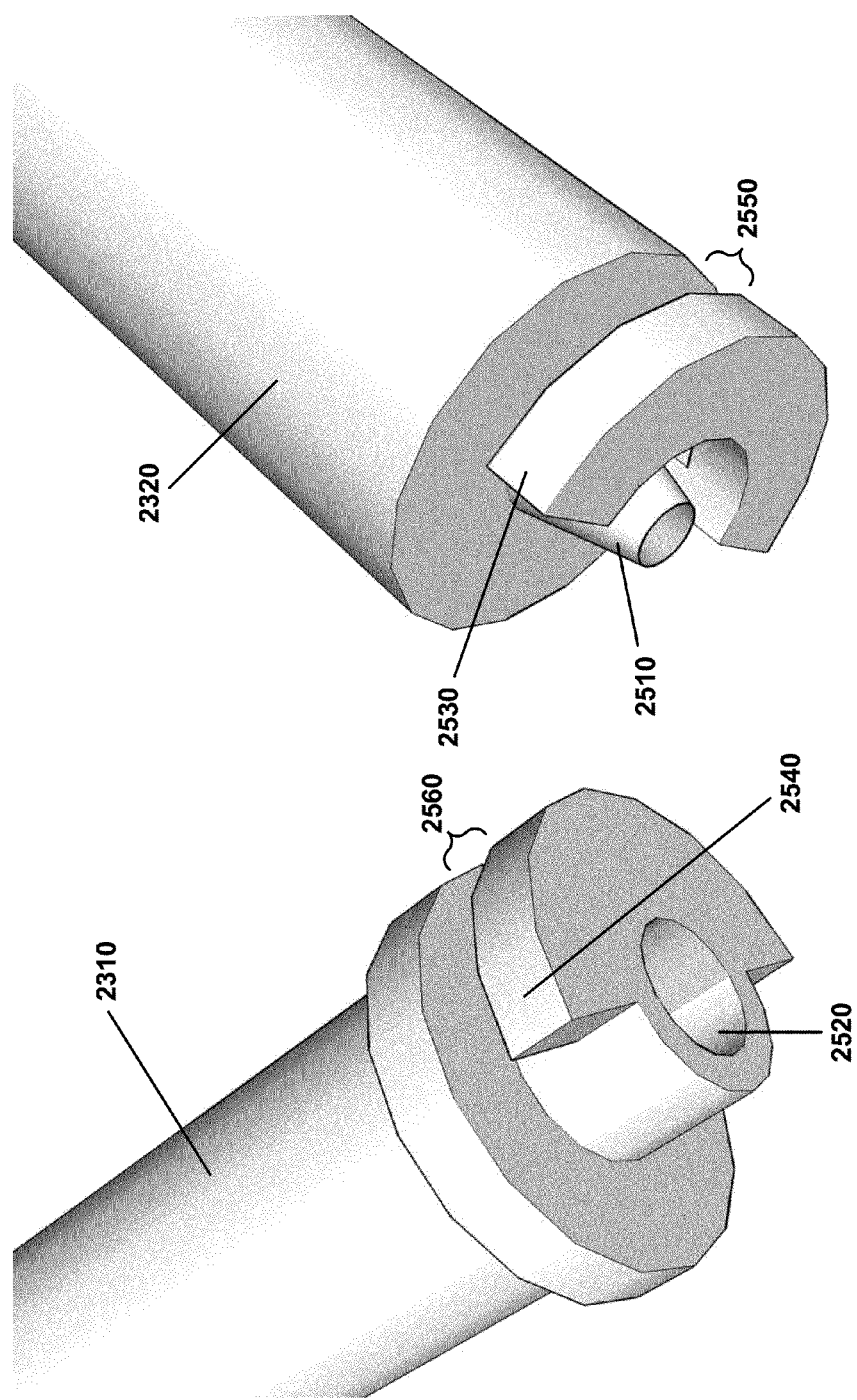
Figure 25D:
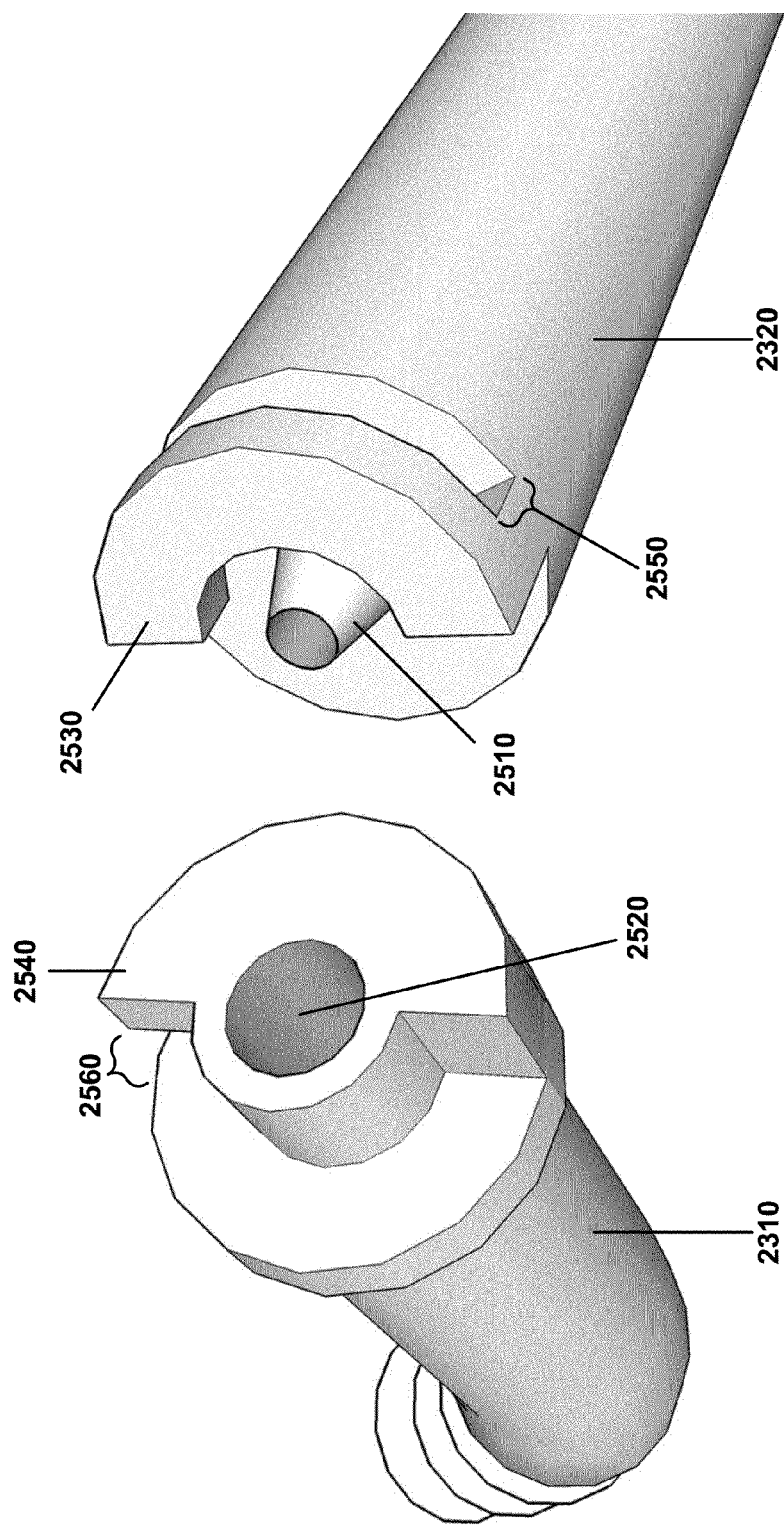

In FIGS. 24A-24B, three configurations of the coupling mechanism 1450 are shown. These figures illustrate a fully coupled configuration 2450 of the anchoring member with the driving member, a partially coupled configuration 2460, and a fully decoupled configuration 2470. FIGS. 25A-25D provide detailed illustrations of the coupling mechanism.

As shown in FIGS. 24-25, the coupling mechanism 1450 couples the anchoring member with the driving member. A similar coupling mechanism 1450 was mentioned above for coupling intervening member 1920 and anchoring member 1910 of FIG. 19. In FIGS. 24-25, the coupling mechanism includes a male member 2510 and a female member 2520. The male member includes a protruding stub encompassing the central lumen of the driving member. It also includes an arm 2530 and a slot 2550 behind the arm 2530. The female member 2520 includes an indentation that leads to the central lumen of the anchoring member. It also includes an arm 2540 and a slot 2560 behind the arm 2540 that complements and rotatably couples with the slot 2550 and the arm 2530 of the male member 2510.

As mentioned above, the coupling mechanism is integrated into the distal end of the driving member in some embodiments (e.g. anchoring needle in FIGS. 24A-24B), while other embodiments utilize the intervening member and integrate the coupling mechanism into the intervening member. In either configuration, the anchoring member may detach from the driving member or intervening member by separating the coupling mechanism. To separate the coupling mechanism, the driving member shaft may be rotated until the interlocking arms 2530-2540 exit the slots 2550-2560 in which they were inserted, and the arms 2530 of the male member 2510 and arms 2540 of the female members 2520 clear each other, as shown in the configuration 2460 of FIGS. 24A-24B. Once the interlocking arms are clear of each other, the driving member and the intervening member may be pulled away and removed from the anchoring member, as shown in the configuration 2470. The separation of the coupling mechanism occurs when the fusion member has been properly positioned and after the polymer is injected (as further described by reference to FIGS. 26-28).

As mentioned above, the delivery housing channel of some embodiments can be circular and constant in diameter throughout the entire length of the channel as described above in FIGS. 7A-7C. In some such embodiment, the flexibility of the anchoring member enables the anchoring member to be advanced through the curved channel of the fusion member.

FIGS. 26-28 illustrate an example of the injection of PMMA, or other bone cement or hardening polymer, through the anchoring members and into the vertebral bodies. Any number of known techniques/procedures for injecting PMMA into the anchoring member can be used. One such technique involves injecting or pumping PMMA into the anchoring member through use of a needle or syringe.

In this example, two anchoring members are inserted into the two channels of a fusion member. One of ordinary skill will realize that the same operations can be performed for the embodiments that use four anchoring members through a fusion block with four channels as further described in Section V.

Figure 26A:
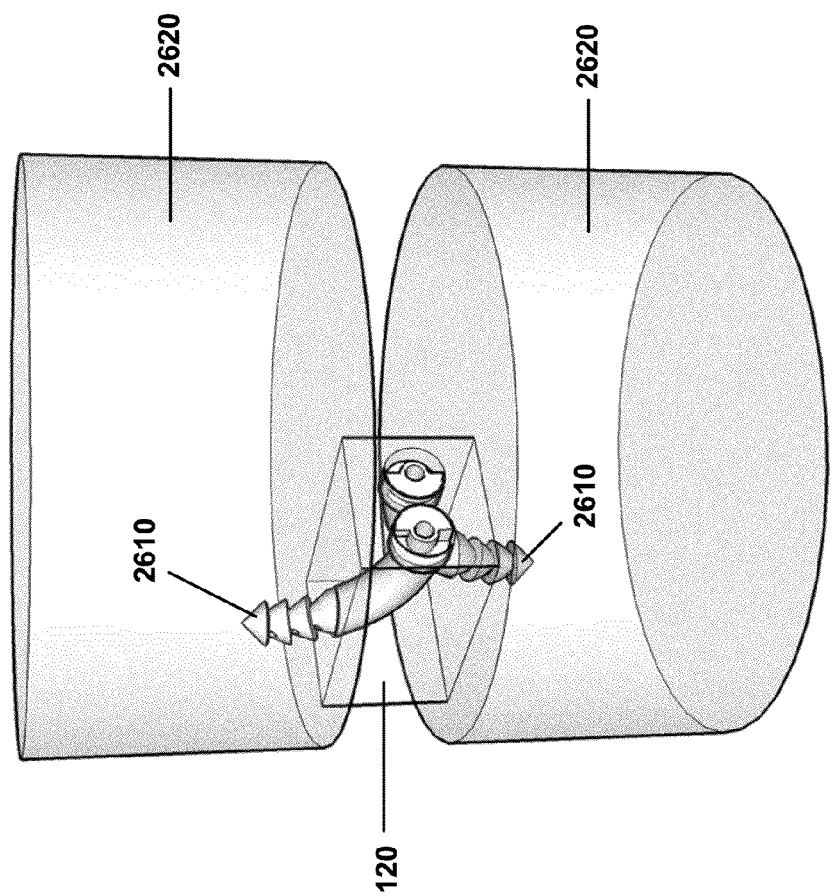
FIGS. 26A-C show two anchoring members that have been inserted through the fusion member and into the vertebral bodies.
Figure 26B:
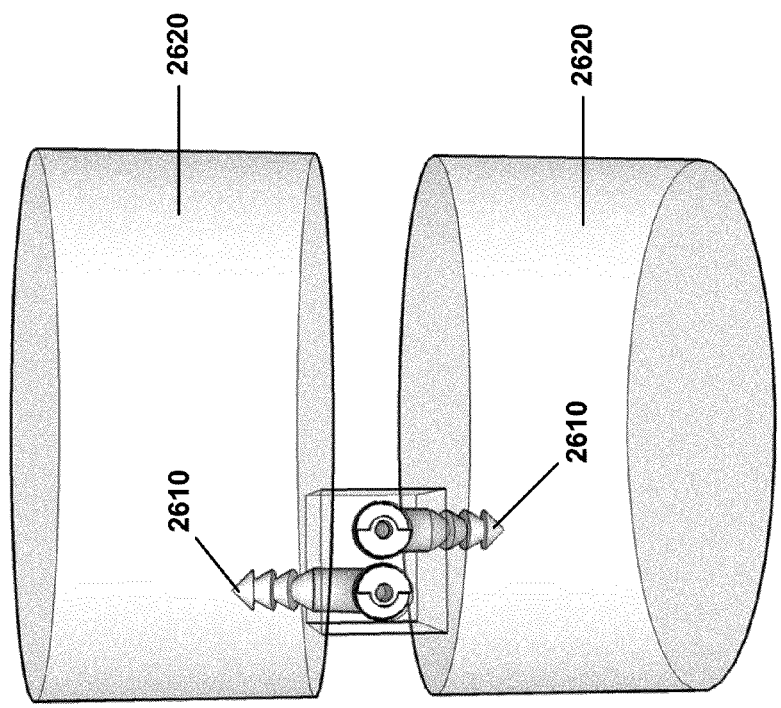
Figure 26C:
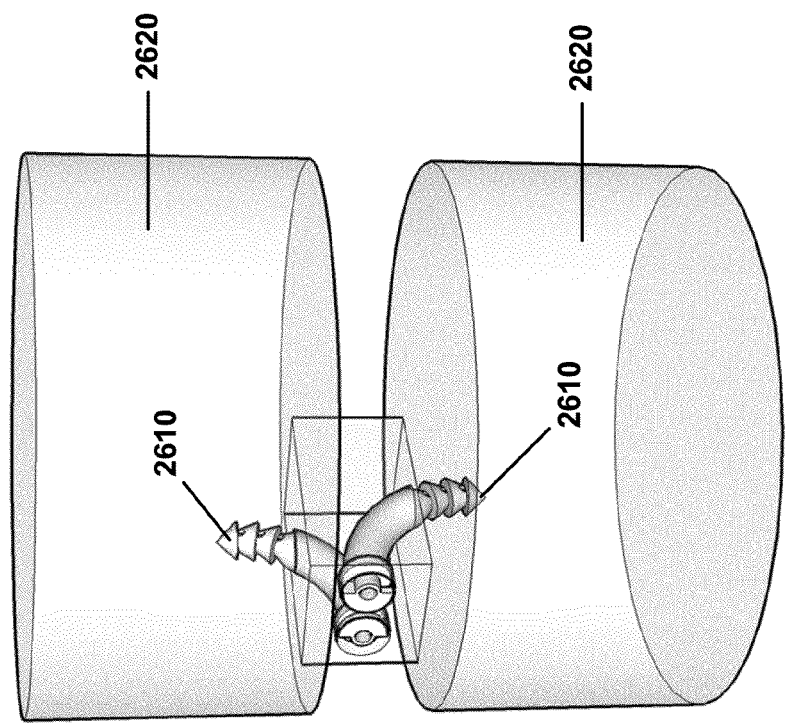
Figure 27A:
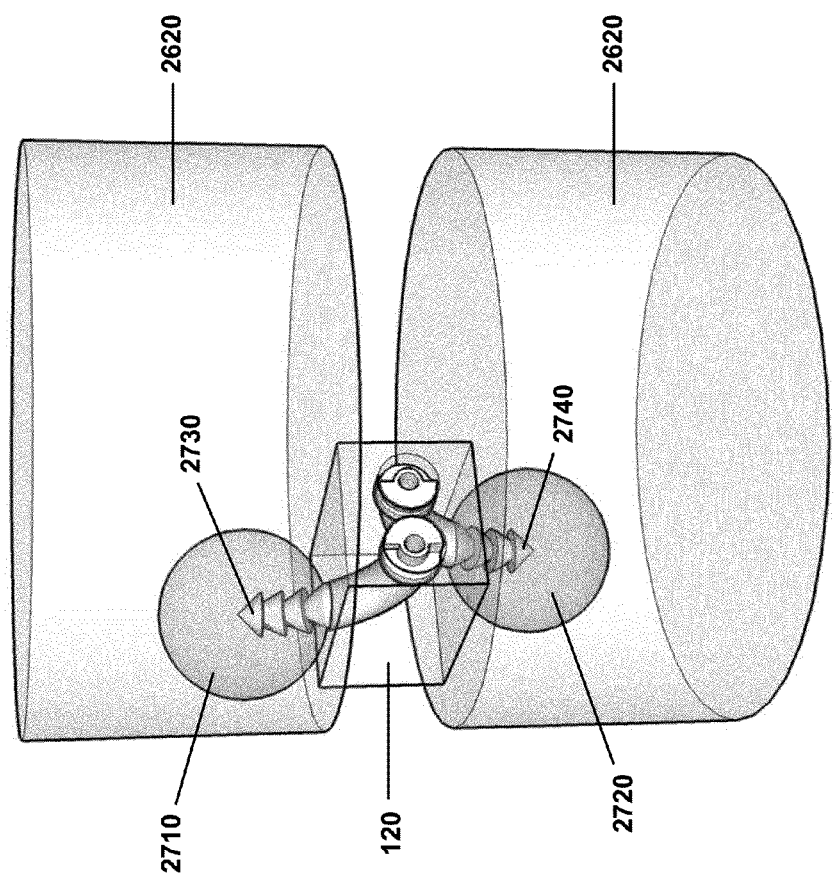
FIGS. 27A-27B depict the placement of one fusion member between adjacent vertebral bodies, a set of two anchoring members that have affixed the fusion member to the vertebral bodies, and the coalescence of the polymer collections that resulted following injections of the polymers via anchoring members.
Figure 27B:
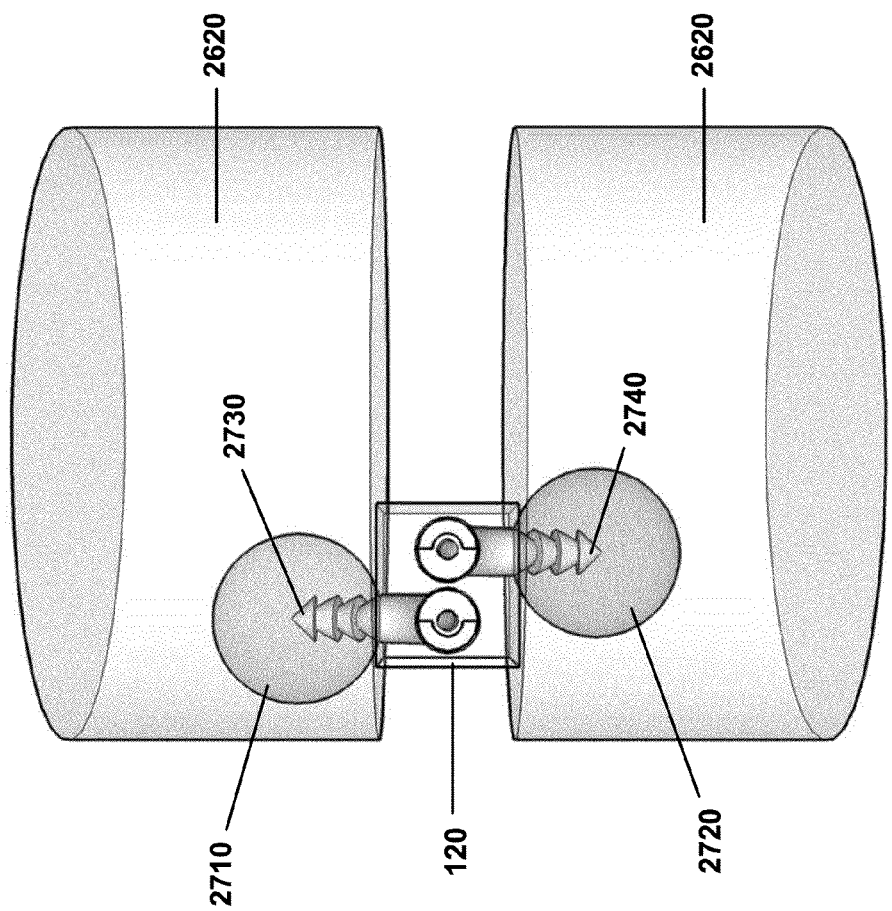

In FIGS. 26A-26C provide different views of two anchoring members 2610 that are fully advanced through the fusion member channels and into the marrow space of adjacent vertebral bodies 2620 immediately above and below the fusion member 120. Polymer can be injected through the central lumen of the anchoring members and out of the perforations of the anchoring members into the immediate surrounding area within the marrow space of the penetrated vertebrae. FIGS. 27A-27B depict different views of the coalescence of the polymer collections 2710-2720 that result following injections of these polymers via anchoring members 2610, respectively. The coalescence 2710-2720 of these polymers forms a spherical or ellipsoidal "cloud" contiguous with the tip 2730-2740 of the anchoring members 2610. In its initial state, the polymer is in a semi-fluid state or in a gel-like state that allows it to flow through the anchoring member channel and the openings of its tip to fill in the marrow space of the vertebral body and the contours of the anchoring member tip. However, within a short period of time, the polymer hardens within the marrow space, resulting in a structural union between anchoring members 2610, vertebral bodies 2620, and the fusion member 120. The contoured tips of the anchoring members in conjunction with the hardened polymer prevent withdrawal of the anchoring member 2610 from the trabecular bone and enhances the structural integrity of the fusion member 120. The final result is an intervertebral fusion member 120 anchored via multiple anchoring members 2610 to collections of hardened polymer 2710-2720 (e.g., PMMA or other bone cement) and to the trabecular bone of adjacent vertebral bodies 2620 yielding solid mechanical fusion. Once the anchoring members are in place, and the polymer has been injected into the marrow space of the vertebral bodies, the driving members may be disengaged from the anchoring members and removed from the patient.

Figure 28A:
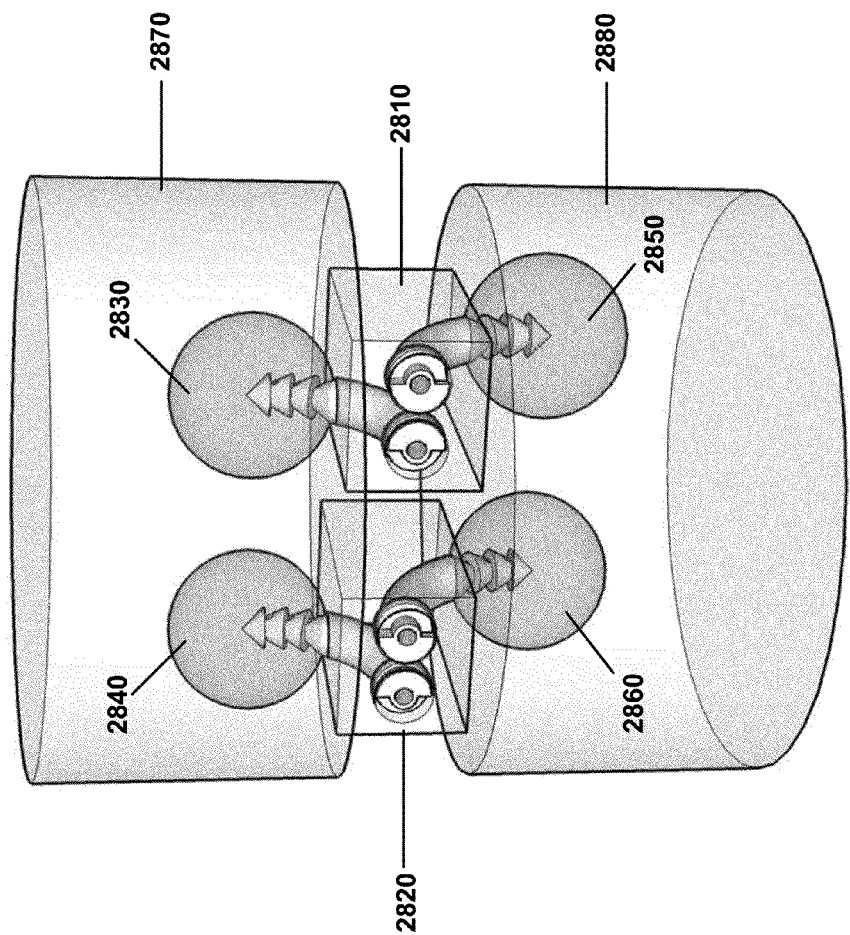
FIGS. 28A-28B depict placement of two fusion members within the right and left paramedian disc space of adjacent vertebral bodies, multiple sets of anchoring members that have affixed the two fusion members to the vertebral bodies, and the coalescence of polymer clouds following the polymer injections.
Figure 28B:
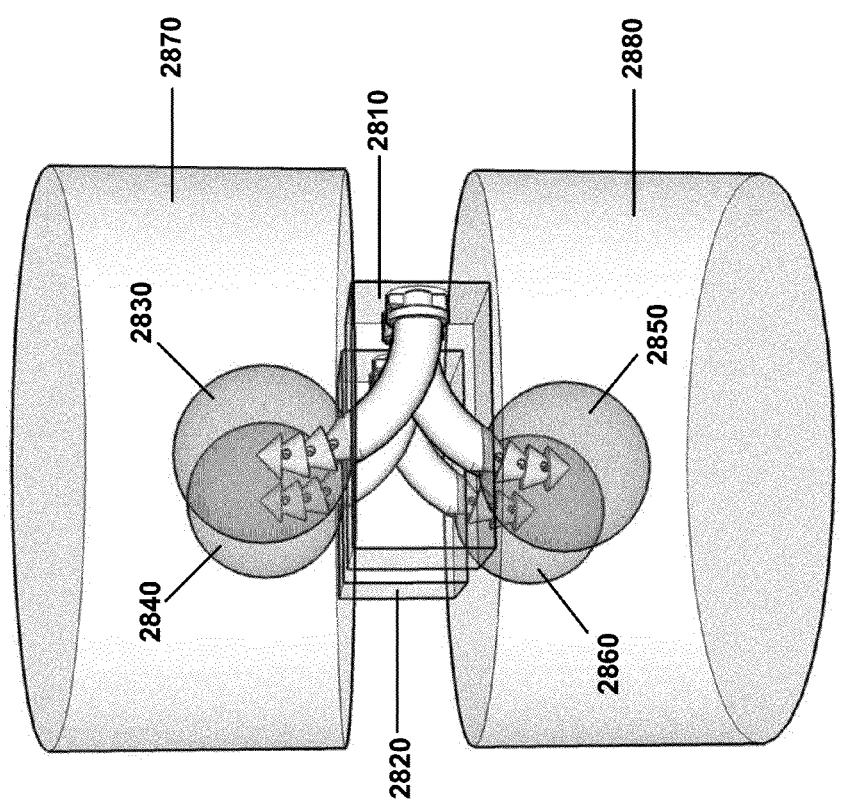

Some embodiments insert more than one fusion member between a pair of adjacent vertebral bodies. One such example is illustrated in FIGS. 28A-28B. These figures depict (1) placement of two fusion members 2810-2820 within the right and left paramedian disc space of vertebral bodies 2870-2880, (2) multiple sets of anchoring members into the vertebral bodies 2870-2880, and (3) coalescence of polymer "clouds" 2830-2860 following the polymer injections. The resultant polymer clouds from adjacent tips of anchoring members may form upon polymerization. The clouds along with multiple contoured and perforated anchoring members lock the fusion members 2810-2820 to the trabecular bone of vertebral bodies 2870-2880.

3. Anchoring Member

As mentioned above in reference to FIG. 18, the anchoring member can be composed of a material or a combination of materials that provides flexibility as shown in. To provide flexibility, the anchoring member can be composed of materials such as nitinol, stainless steel, titanium or other metals, metallic alloys, or high density polymers, carbon fiber, collagen or other biological materials, completely absorbable or partially absorbable material, or of a combination of these materials. In some embodiments, the tip of the anchoring member may be open or closed.

In some embodiments, the anchoring member can be composed of a bio-absorbable polymer (such as collagen). Bio-absorbable polymer (e.g., collagen) allows the anchoring member to be resorbed by the patient (e.g., three to four months in the case of collagen) after the anchoring member has been inserted into the vertebral body of the patient. Some such bio-absorbable material (like collagen) also provides flexibility to allow the anchoring member to have a range of motion from 0 to 90 degrees. In some embodiments, the shaft of the anchoring member can be composed of bio-absorbable material (e.g., collagen) while the tip of the anchoring member can be composed of another material (e.g., nitinol) to facilitate penetration of the anchoring member into the vertebral body.

D. Fusion Apparatus

In some embodiments, the intervertebral fusion apparatus that includes the anchoring member, fusion member, and delivery member is already pre-assembled. In some embodiments, the delivery housing and the retention rods are assembled to form the delivery mechanism. The fusion member is coupled to the delivery mechanism by the retention rods. The anchoring member is coupled to the driving member to form the anchoring mechanism.

However, in different embodiments, the fusion apparatus may be pre-assembled to different degrees. For instance, in some embodiments, the anchoring mechanism may be pre-assembled to varying degrees in relation to the fusion member and the delivery mechanism. In some embodiments, the tip of the anchoring member of the anchoring mechanism is partially inserted in the fusion member channel. In other embodiments, the tip of the anchoring member is inserted into the channel of the delivery housing but not in the fusion member channel. Yet, in other embodiments, the anchoring mechanism is not inserted at all in the fusion member channel or in the delivery housing channel and may be inserted into the apparatus when needed.

IV. Example of a Fusion Procedure

Figure 29:
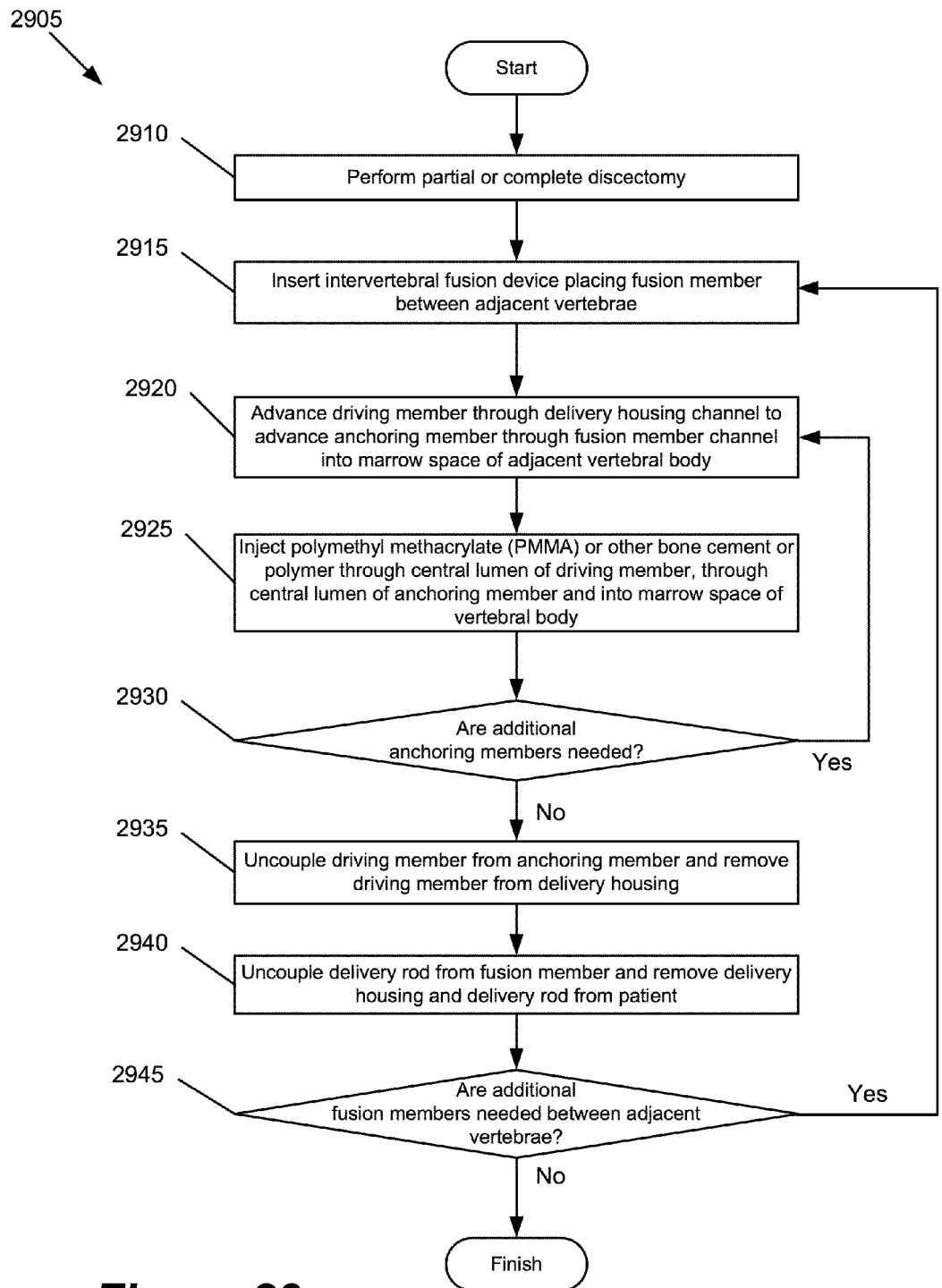
FIG. 29 depicts a medical procedure that involves the insertion of the apparatus of some embodiments.
Figure 30:
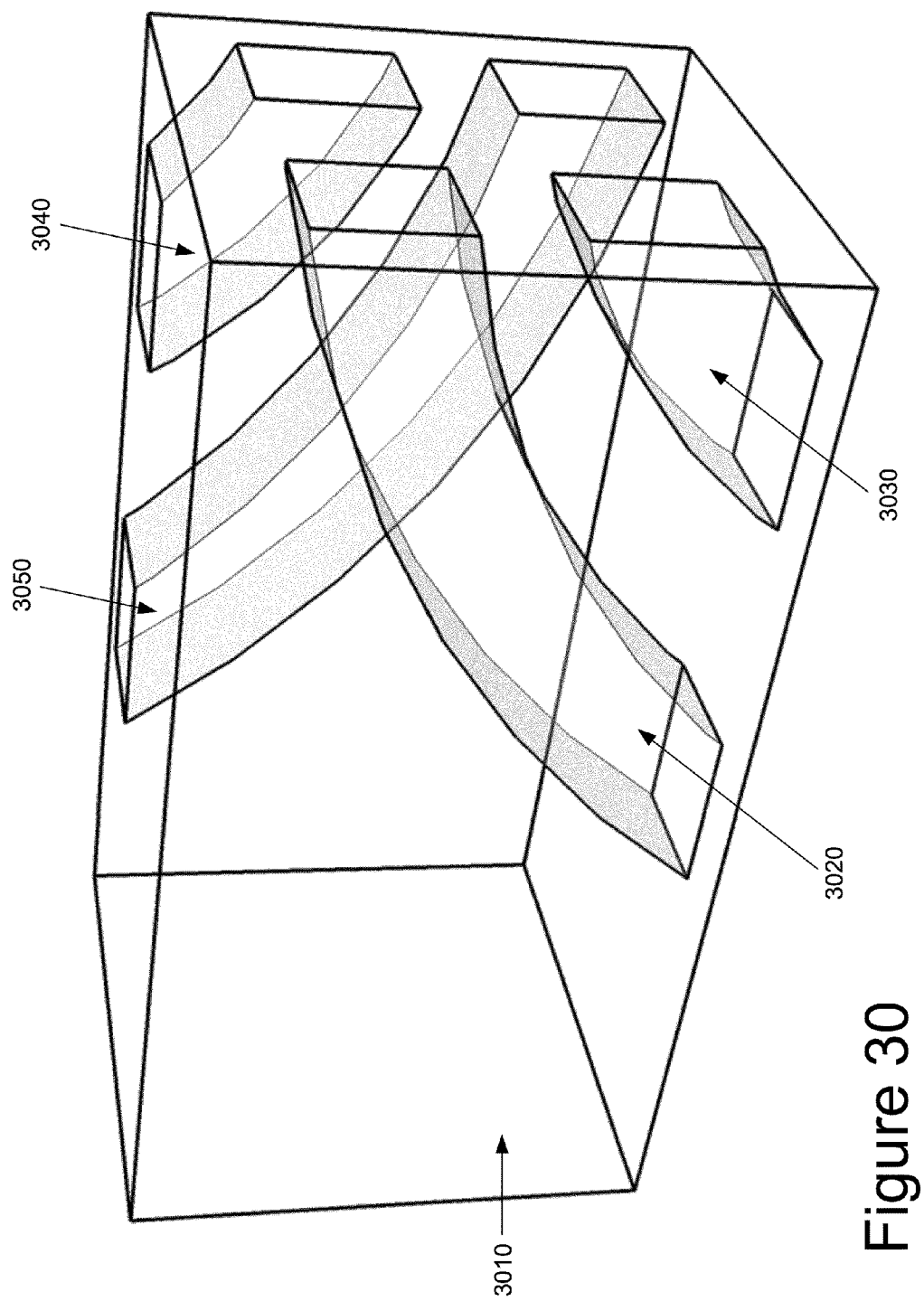
FIGS. 30-33 illustrate different views of an interbody fusion member comprising curved tubular channels with distal openings on the superior block face and inferior block face.
Figure 31:
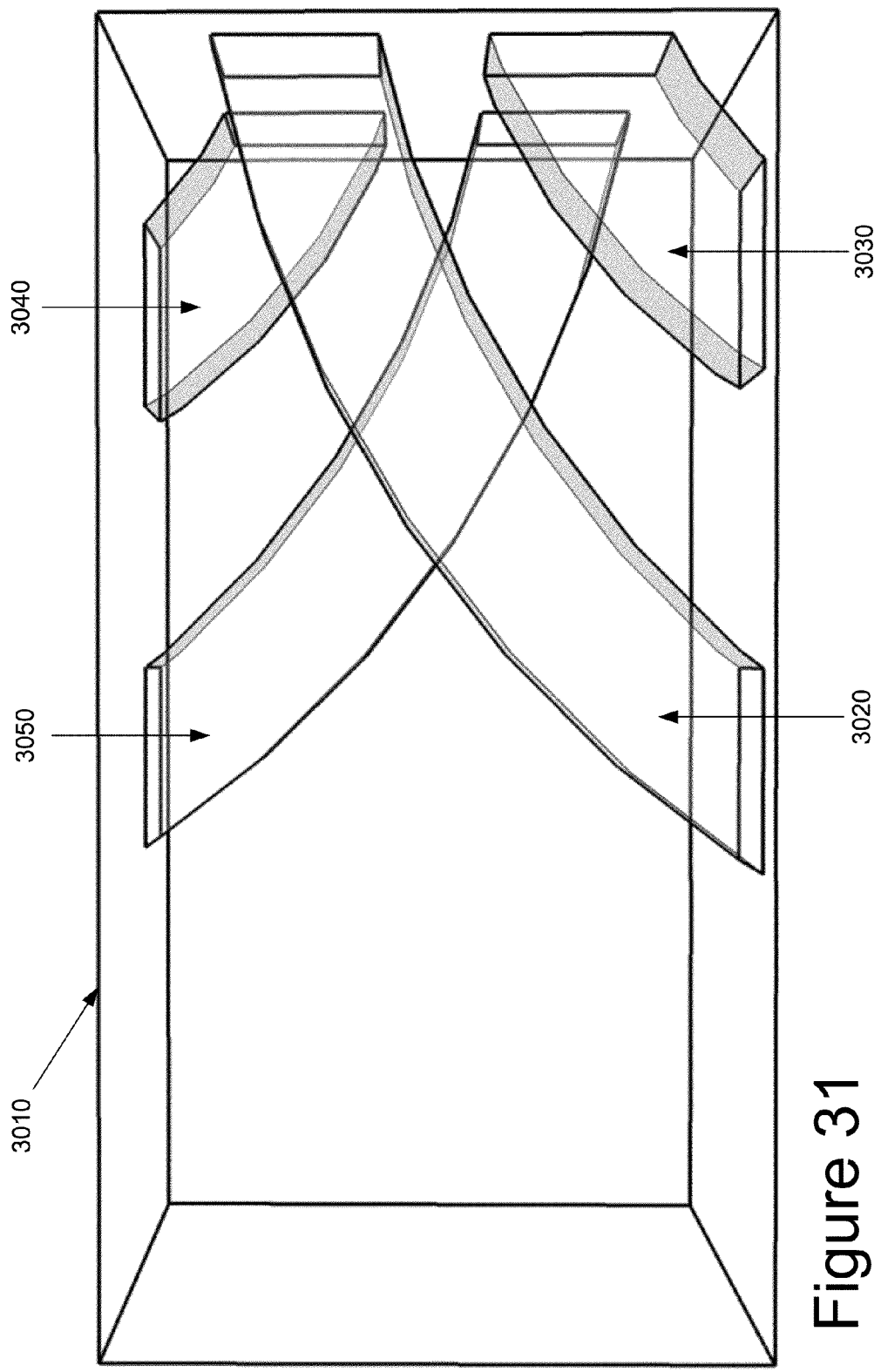

The operation of apparatus 110 will now be described. FIG. 29 depicts a medical procedure 2905 that involves the insertion of the apparatus 110 of some embodiments of the invention. In this procedure, a medical practitioner (e.g., a physician) initially performs (at 2910) a partial or complete discectomy, which typically involves making an incision in a patient and removing some or all of the fibrocartilaginous disc between two adjacent vertebral bodies. Any number of known techniques/procedures can be used to remove the disc at 2910.

Next, the medical practitioner inserts the intervertebral fusion device (at 2915) and positions (at 2915) the fusion member (e.g., one of the blocks described above) between the endplates of adjacent vertebrae. Any number of known techniques/procedures for inserting a fusion member between two adjacent vertebrae can be used (at 2915) to insert the intervertebral fusion device and position the interbody fusion member between adjacent vertebrae. One technique for inserting the fusion member involves the use of one of the delivery mechanisms (e.g., apparatus 110 described above). In some embodiments, a radiograph or x-ray of the patient may be taken (at 2915) to determine if the fusion member is placed at an appropriate position between two vertebral bodies. If not, the medical practitioner can use (at 2915) the delivery mechanism to reposition the fusion member to the desired location.

Once the fusion member has been properly positioned, the medical practitioner passes (at 2920) at least one anchoring member (e.g., large gauge needle) through the fusion member channels (at 2915) and advances the anchoring member into the marrow space of the adjacent vertebral body by applying force on the proximal end of the driving member. In some embodiments, a flange at the base of each anchoring member fits into a recess of increased diameter where the tubular channel meets the exposed surface of the fusion member, in order to lock the anchoring member's position, anchoring it to the fusion member, as described above.

In some embodiments, the medical practitioner exerts force on the driving member by tapping, hammering, or simply pushing at its proximal end to advance the anchoring member into the vertebral body, which the anchoring member encounters as it exits the fusion member channel in which it is inserted. To facilitate this penetration, the medical practitioner in some embodiments inserts a smaller gauge anchoring member into the channel of the fusion member and into the marrow space of the adjacent vertebral body before inserting the anchoring member at 2920. This creates a guide to help ensure the anchoring member will be advanced into the proper position within the trabecular bone of the vertebral body. In some embodiments, a radiograph may be taken of the anchoring members in relation to the marrow space of the vertebral bodies to determine if the anchoring members need to be repositioned. In other embodiments, a robotic arm may be used to advance the anchoring member into the vertebral body.

Once the anchoring member is in position, the medical practitioner (at 2925) injects polymethyl methacrylate (PMMA), other bone cement, or polymer through the central channels of the driving member, intervening member (if any) and the anchoring member, through the anchoring member's openings/perforations, and into the marrow space of the vertebral body. Ideally, the injected material forms a spherical or ellipsoidal cloud of polymer material (e.g., PMMA) contiguous with the tip of the anchoring member.

In some embodiments, multiple anchoring members coupled with the driving member(s) may be advanced through multiple channels of the delivery housing and the fusion member into the same vertebral body. PMMA or other bone cement or polymer may be injected through the central lumen of these additional anchoring members. Accordingly, after 2925, the medical practitioner determines (at 2930) whether additional anchoring members need to be inserted into the fusion member inserted (at 2920). If so, the medical practitioner inserts (at 2920) additional anchoring member(s) through another channel of the fusion member, and injects (at 2925) polymer material through the central lumen of the additional anchoring member and through its openings/perforations into the marrow space of vertebral body. The resultant polymer (PMMA) clouds from adjacent tips of the anchoring member may unite to form a single larger cloud upon polymerization, with multiple contoured and perforated anchoring members locked to the fusion member and anchored to the solid PMMA and trabecular bone of the vertebral body. The final result is an intervertebral fusion member anchored via multiple contoured, perforated anchoring members to collections of PMMA and to the trabecular bone of adjacent vertebral bodies yielding solid mechanical fusion.

When a determination has been made that the insertion of additional anchoring members is not necessary, the medical practitioner (at 2935) uncouples the driving member from the anchoring member and removes the driving member from the delivery housing and from the patient. In some embodiments, robotic arms may be used to uncouple the driving member from the anchoring member and remove the driving member from the delivery housing.

Once the driving member has been removed from the patient and the delivery housing is no longer needed, the medical practitioner uncouples the retention rods from the fusion member. In some embodiments, this is achieved by rotating the retention rods 180 degrees so that the retention teeth of the retention rods disengage (at 2940) from the retention grooves of the fusion member. Once uncoupled, the retention rods may be separated from the fusion member, and the delivery housing along with the retention rods may then be removed (at 2940) from the patient. In some embodiments, robotic arms may be used to uncouple the retention rods from the fusion member and remove the retention rods from the delivery housing.

In some embodiments, more than one fusion member is inserted between two adjacent vertebral bodies. Accordingly, the medical practitioner determines (at 2945) whether another fusion member needs to be inserted between the vertebral bodies between which the last fusion member was inserted (at 2915). If so, the medical procedure is repeated from 2915 to 2940. Also, in some embodiments, the medical procedure 2905 is performed multiple times to replace multiple discs between multiple pairs of vertebral bodies.

V. Alternatives Shapes and Structures

A. Arc Shaped Fusion Member Channels Traversing in a Parallel Cross-Sectional Plane The shape and composition of the fusion members and the anchoring members are different in different embodiments of the invention. For instance, in some embodiments, the anchoring members and the fusion-member channels are in shape of an arc as depicted in FIGS. 30-33. In these figures, one set of tubular fusion member channels 3020 and 3030 follow concentric semi-circular arcs to reach the inferior face of fusion member 3010. The second set of tubular fusion member channels 3040 and 3050 follow concentric semi-circular arcs to reach the superior face of the fusion member 3010. Each set of concentric arcs traverse along a cross-sectional plane that runs parallel to one of the fusion member surfaces.

Figure 32:
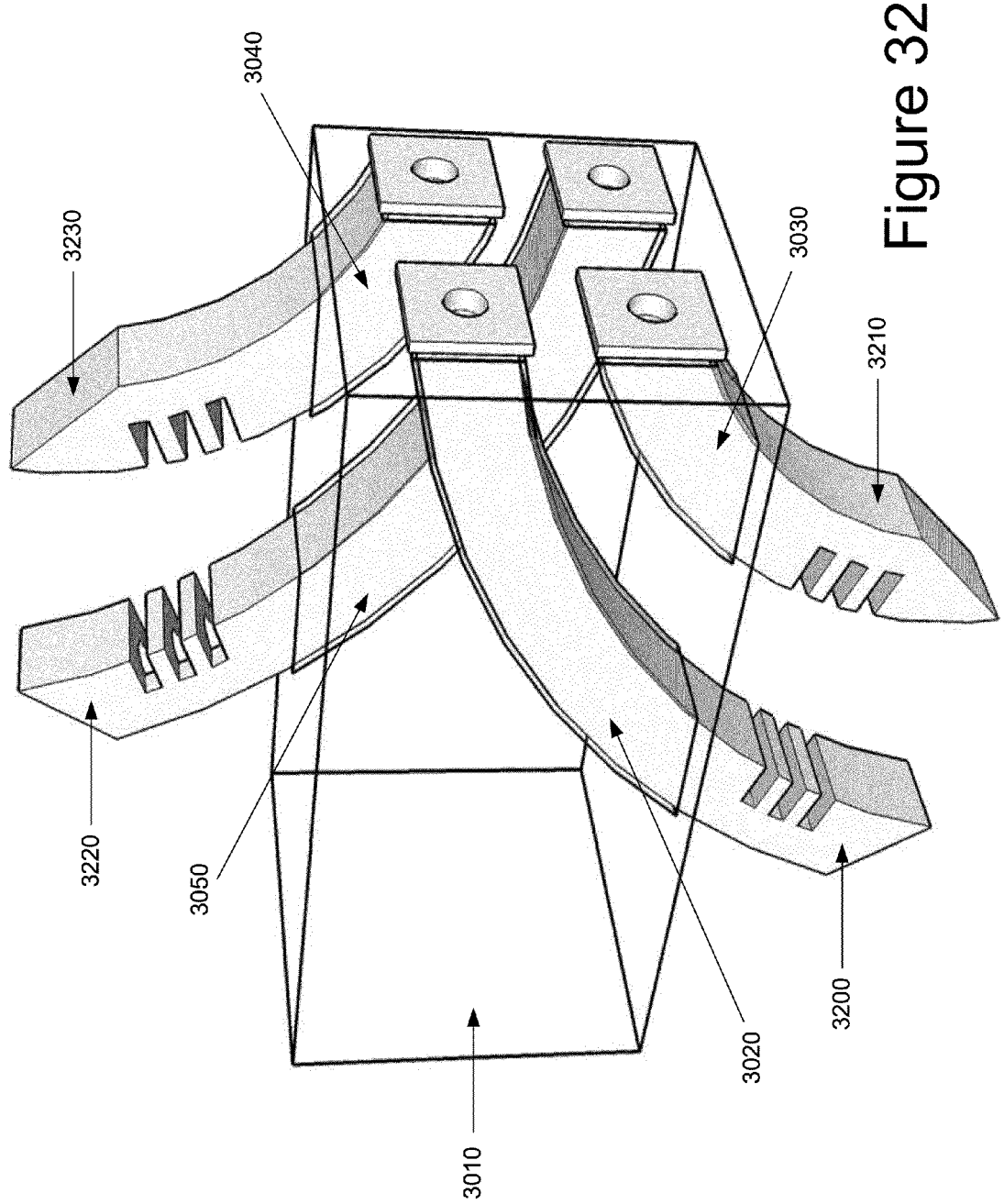
Figure 33:
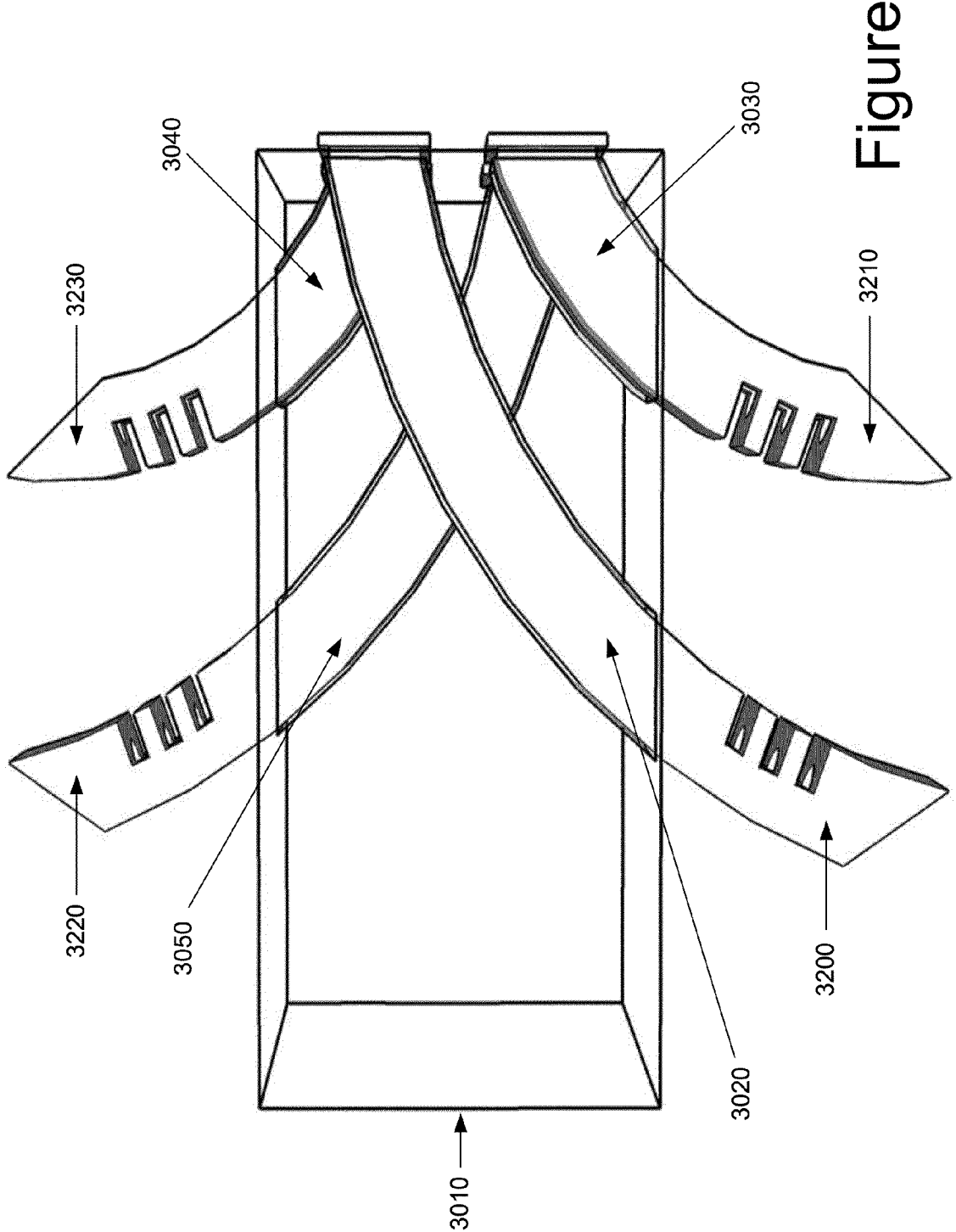

These channels can be traversed by semi-circular arc shaped anchoring members, as illustrated in FIGS. 32-33. Specifically, FIGS. 32-33 show passage of anchoring members through these semicircular tubular channels with anchoring members 3200 and 3210 passing into the marrow space of the vertebral body (not pictured) beneath the fusion member, and anchoring members 3220 and 3230 passing into the vertebral body contiguous with the superior face of the fusion member (not pictured). Semi-circular arc-shaped channels and anchoring members simplify the process of inserting anchoring members into the channels, given the small space in which the fusion member is inserted between the vertebral bodies and the difficulty in accessing the proximal openings of the fusion member within the confines of the operative field. The anchoring members 3200-3230 are flexible in some embodiments, while being rigid in other embodiments.

Figure 34:
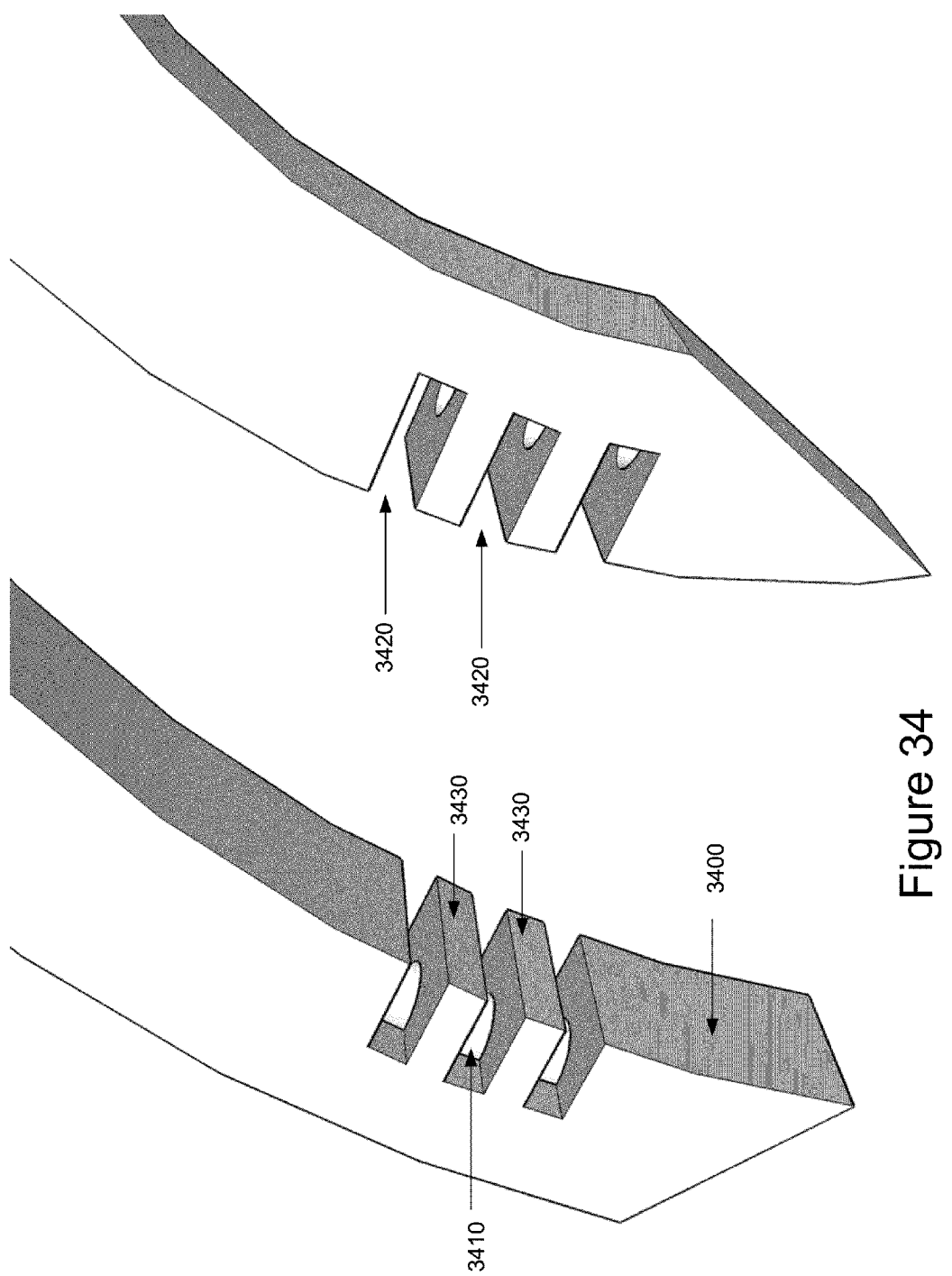
FIG. 34 illustrates a detailed view of the anchoring member tips of one embodiment.

FIG. 34 provides a detailed view of an anchoring member tip 3400 of some of the arc-shaped embodiments. As shown in this figure, a central lumen 3410 of the arc-shaped anchoring member of some embodiments is in direct communication with perforations 3420 along the anchoring member shaft as well as the "teeth" or retention ridges 3430. This allows the polymer material to be delivered to the area adjacent to and between the angled teeth or retention ridges 3430, such that these surface contours can engage the polymer materials when it hardens, locking the anchoring member in position within the trabecular bone, thereby locking the fusion member to the vertebral body.

Figure 35:
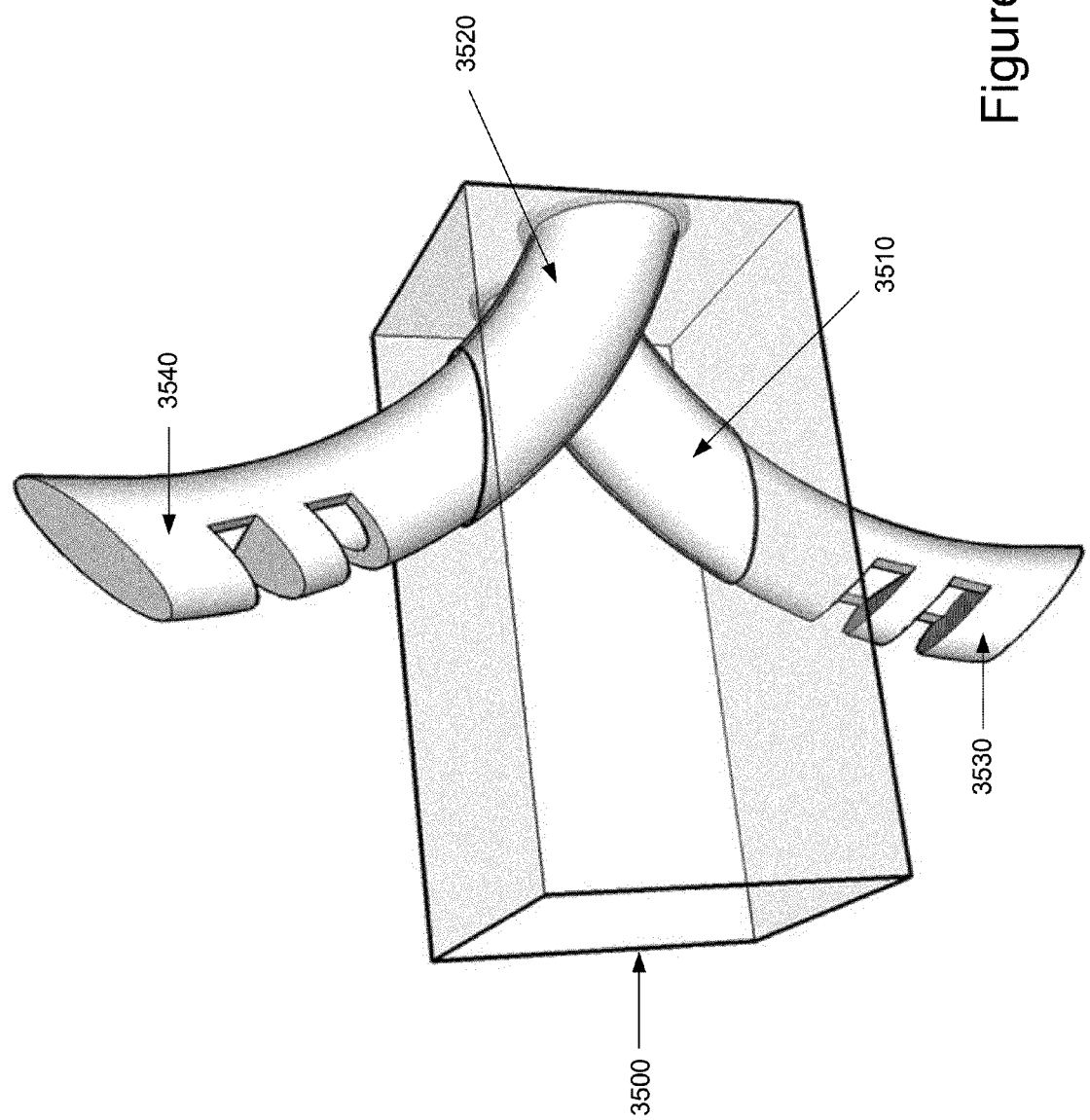
FIGS. 35-36 illustrate different views of anchoring members that have been advanced through the semicircular tubular channels of the fusion member into the marrow space of the vertebral bodies.
Figure 36:
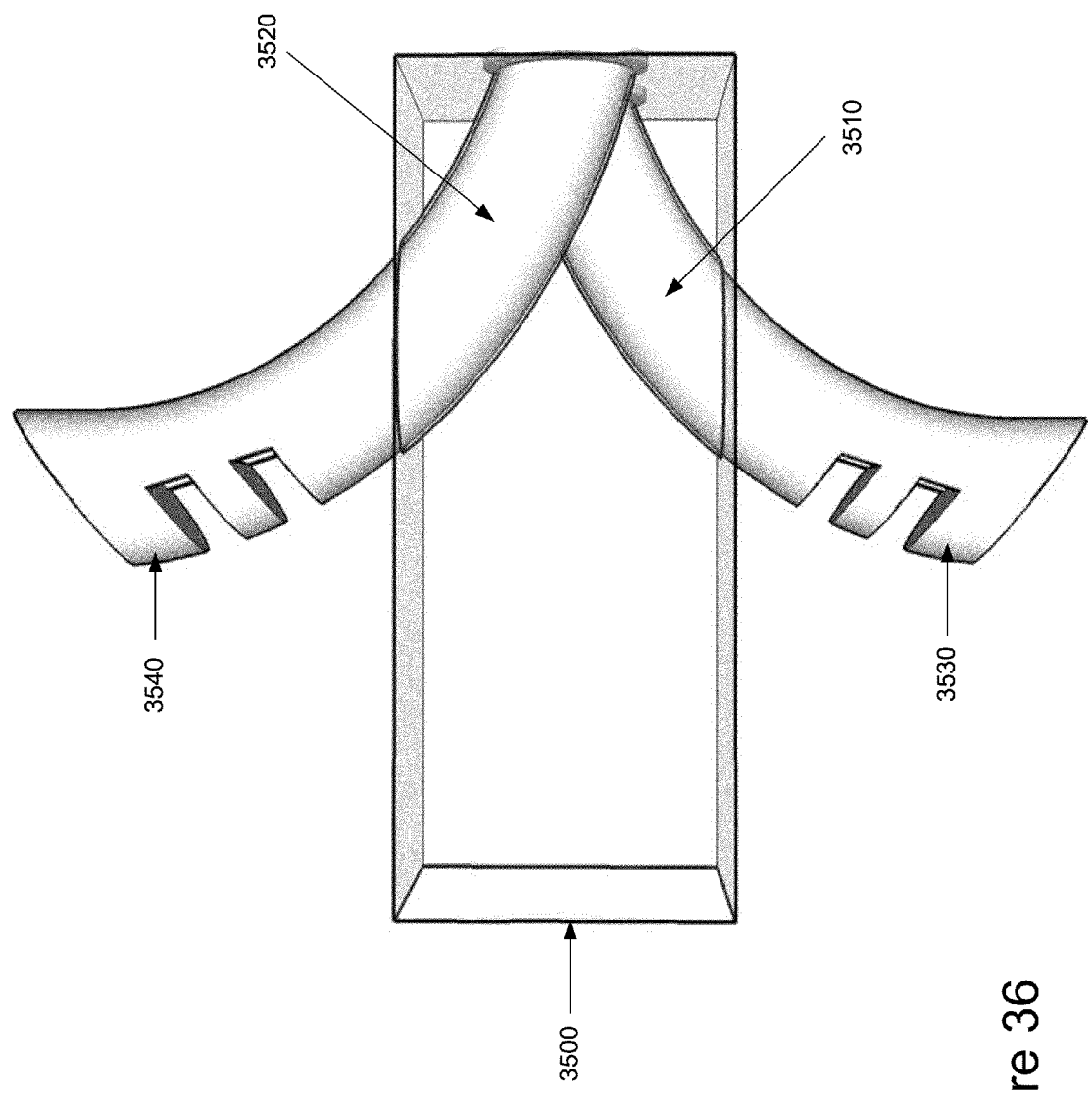
Figure 37:
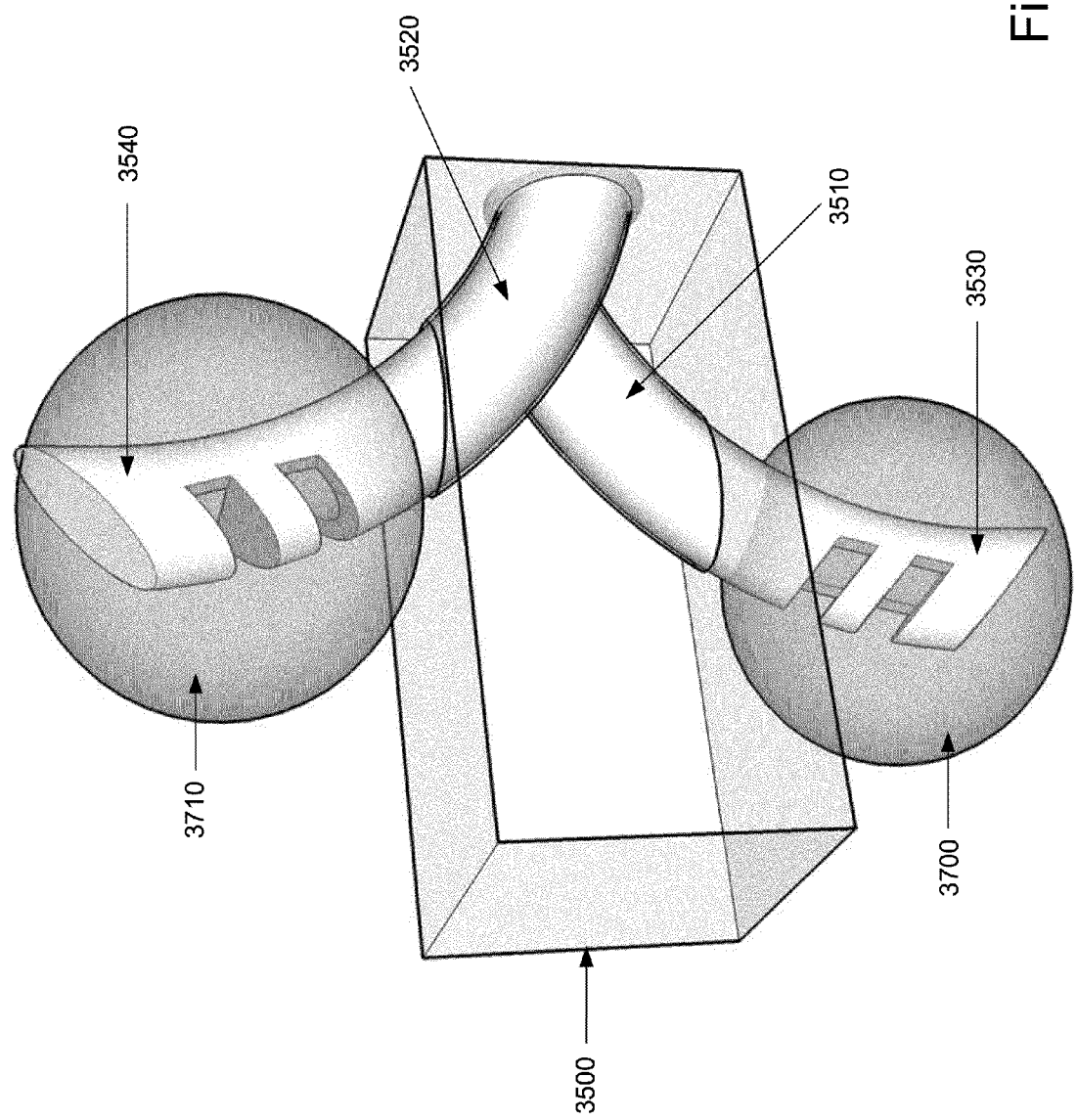
FIG. 37 illustrates PMMA injections through the anchoring members above and below the fusion member.

In FIGS. 35-37, an embodiment of the fusion member 3500 includes two curved semicircular channels 3510 and 3520. This figure shows curved anchoring members 3530 and 3540 fully advanced through these channels and into the marrow spaces of the vertebral bodies (not pictured) below and above the fusion member. In FIG. 37, a polymer has been injected to form "clouds" 3700 and 3710 adjacent to the perforated, contoured tips of anchoring members 3530 and 3540 within the marrow spaces of the adjacent vertebral bodies (not pictured). In this series of figures, channels 3510 and 3520 traverse cross-sectional planes parallel to one another as well as the lateral fusion member surfaces.

B. Fusion Member Channels Traversing in Non-Parallel Cross-Sectional Planes

Figure 38:
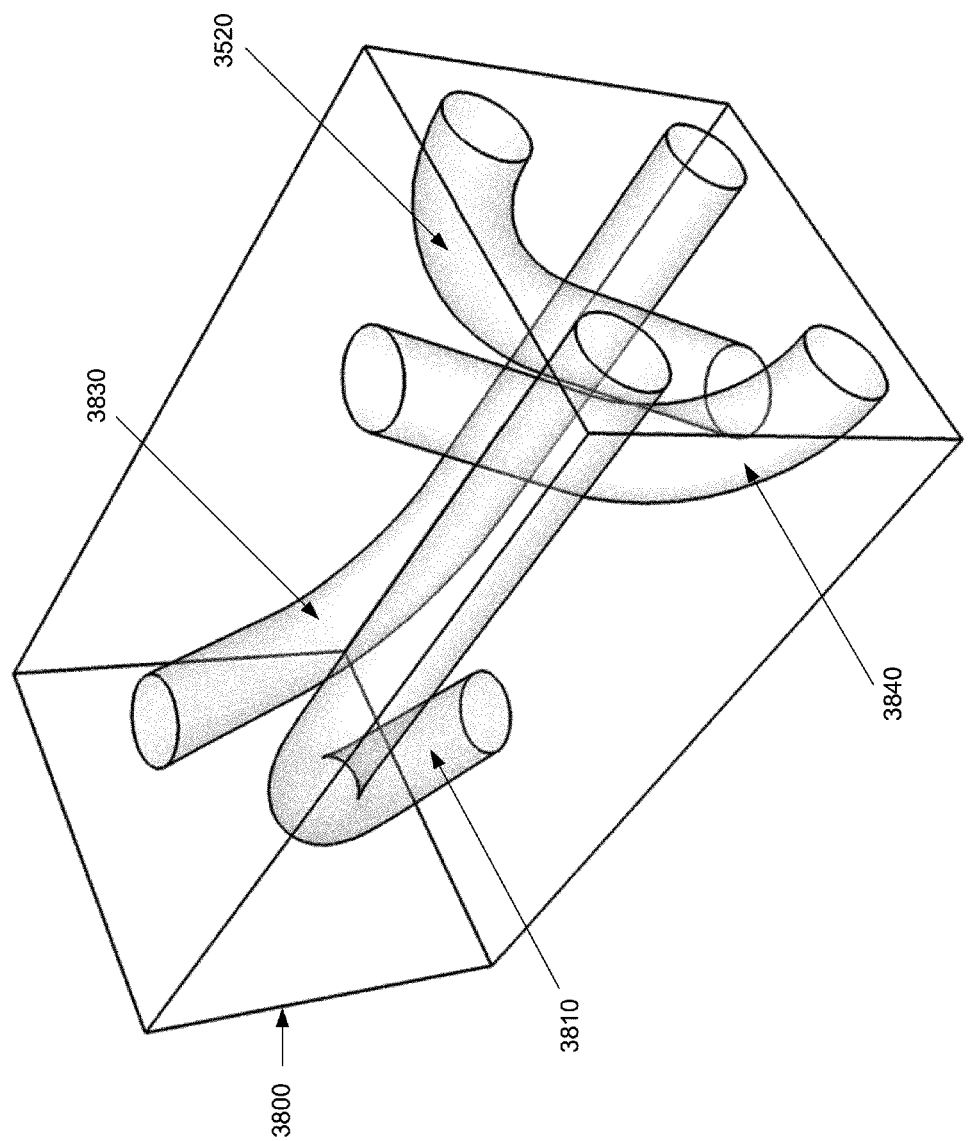
FIGS. 38-40 illustrate different views of an alternative fusion member embodiment with nonparallel angled curved channels extending to the inferior and superior block faces.
Figure 39:
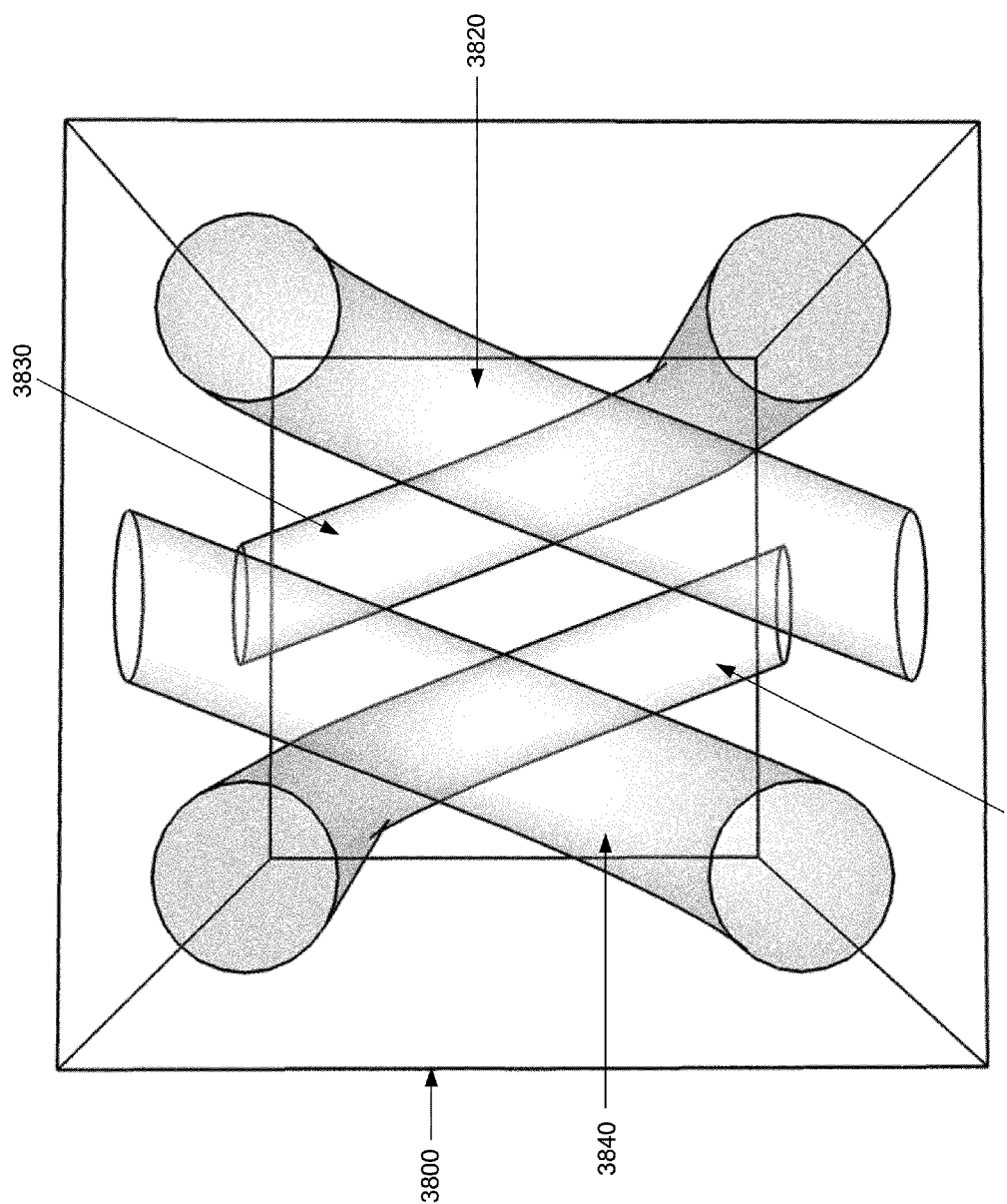
Figure 40:
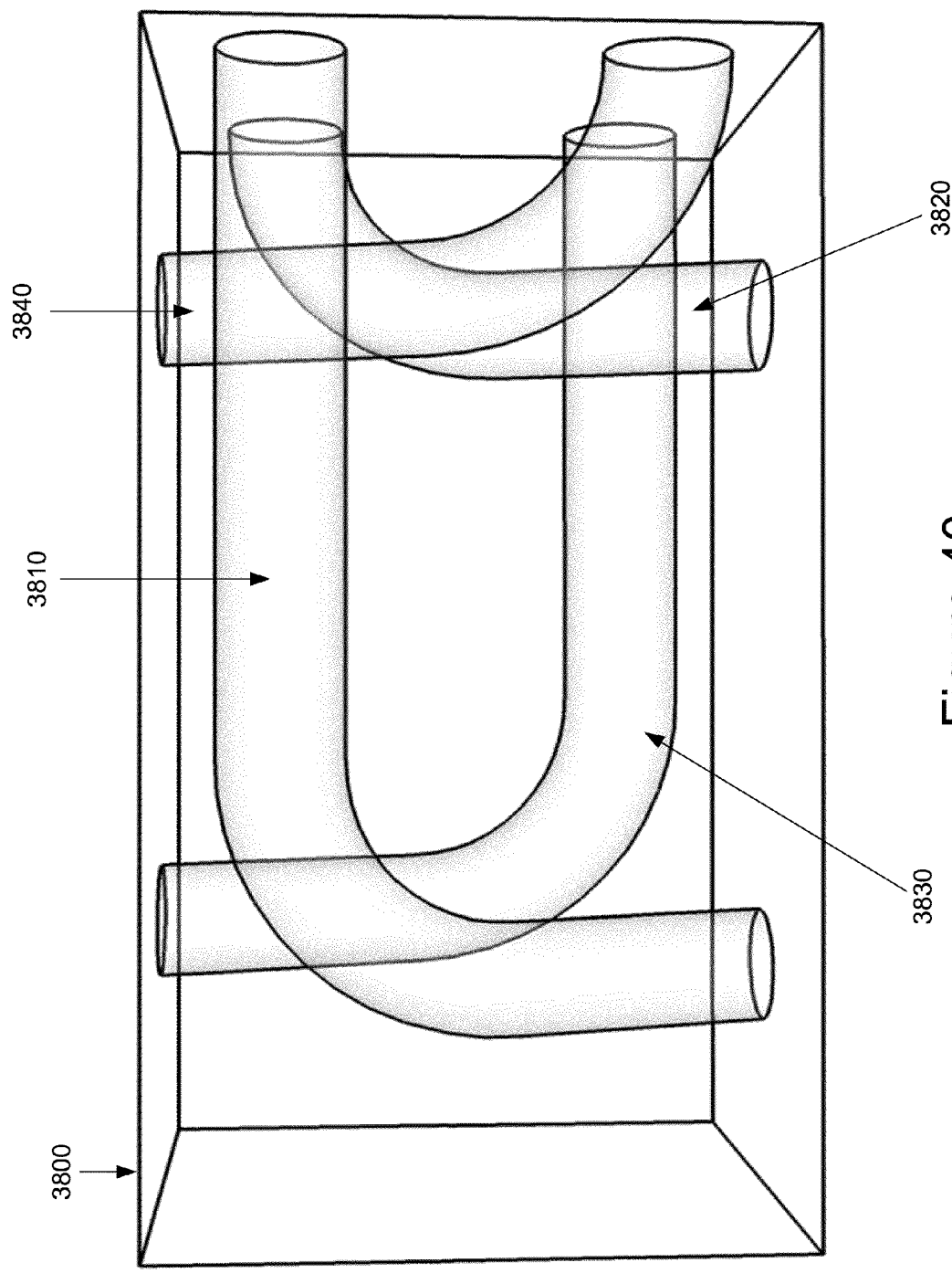

One of ordinary skill in the art will realize that different configurations of the fusion member channels can traverse in x-, y-, and z-directions. FIGS. 38-40 depict an alternate embodiment of the fusion member 3800 with curved channels 3810 and 3820 and curved channels 3830 and 3840 extending to inferior and superior faces of the fusion member, respectively. Channels 3820 and 3840 traverse cross-sectional planes parallel to one another, as do channels 3810 and 3830. Both sets of channels traverse planes that are not parallel with any fusion member surface.

Figure 41:
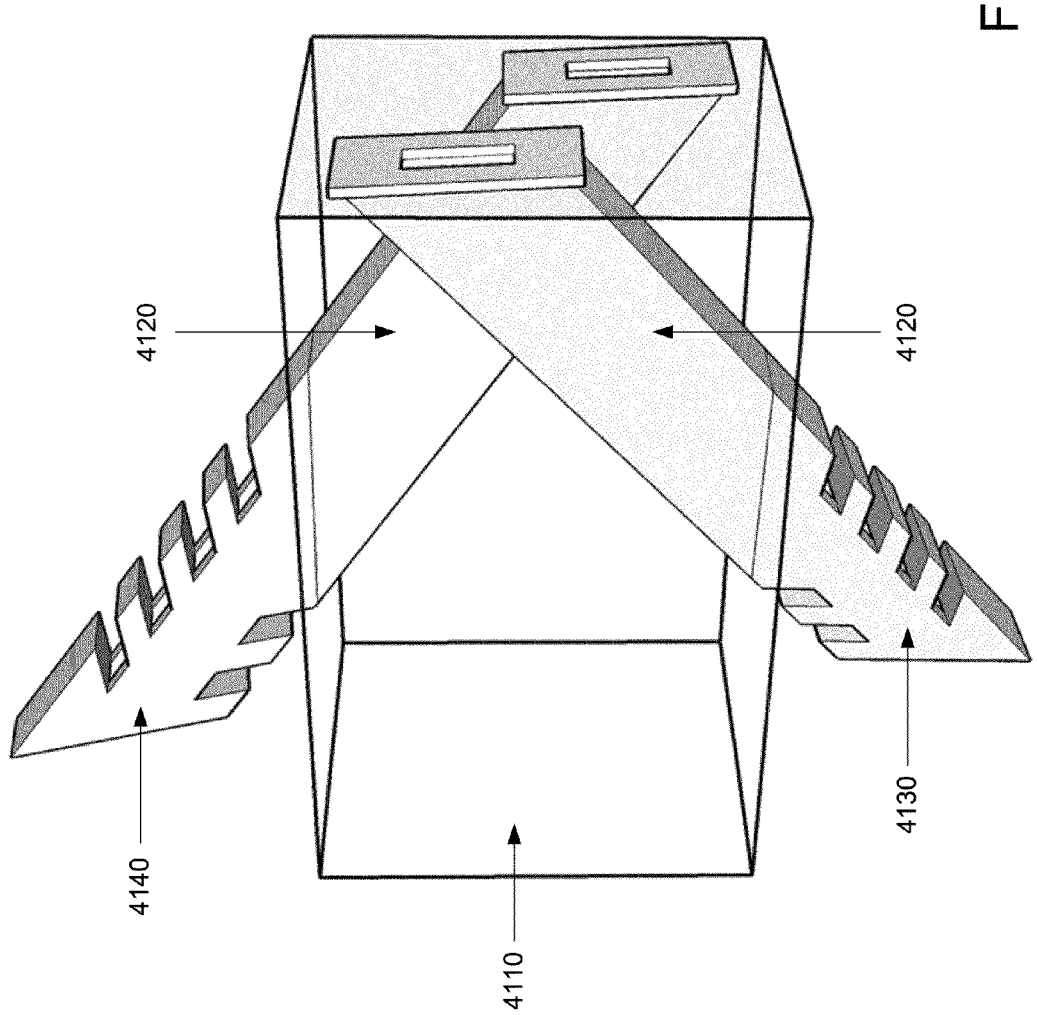
FIGS. 41-42 illustrate different views of an alternative fusion member embodiment comprising oblique linear channels that are traversed by straight anchoring members which are rectangular in cross-sectional profile.
Figure 42:
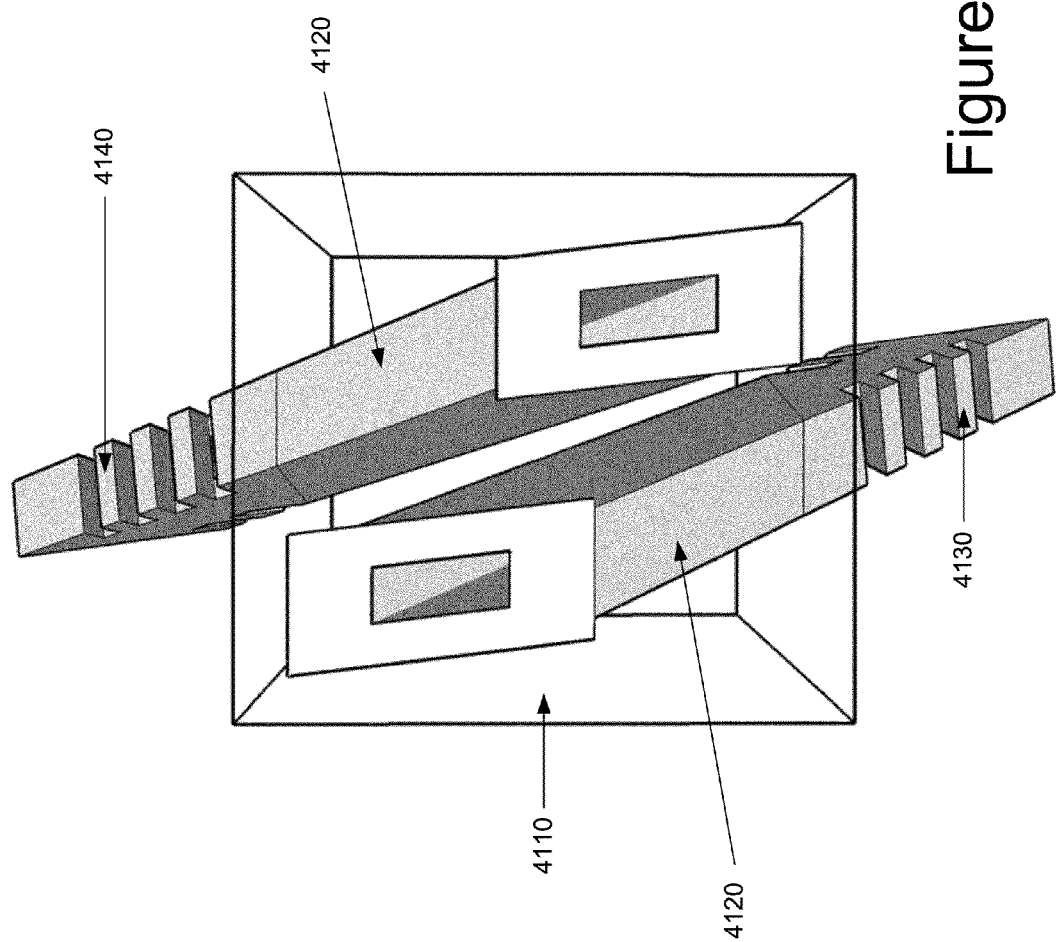
Figure 43:
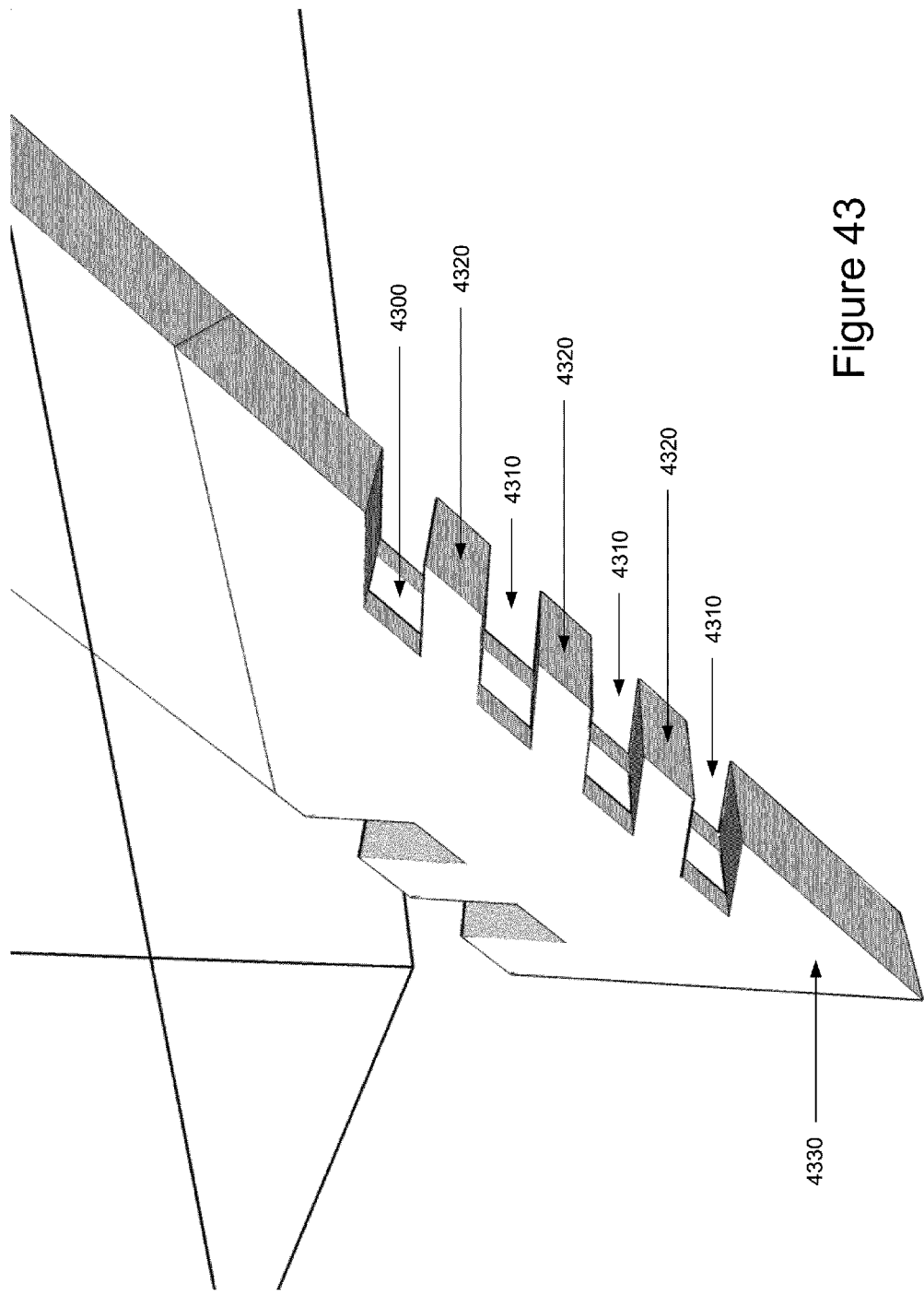
FIG. 43 illustrates the tip of the straight anchoring members which are rectangular in cross-sectional profile.
Figure 44:
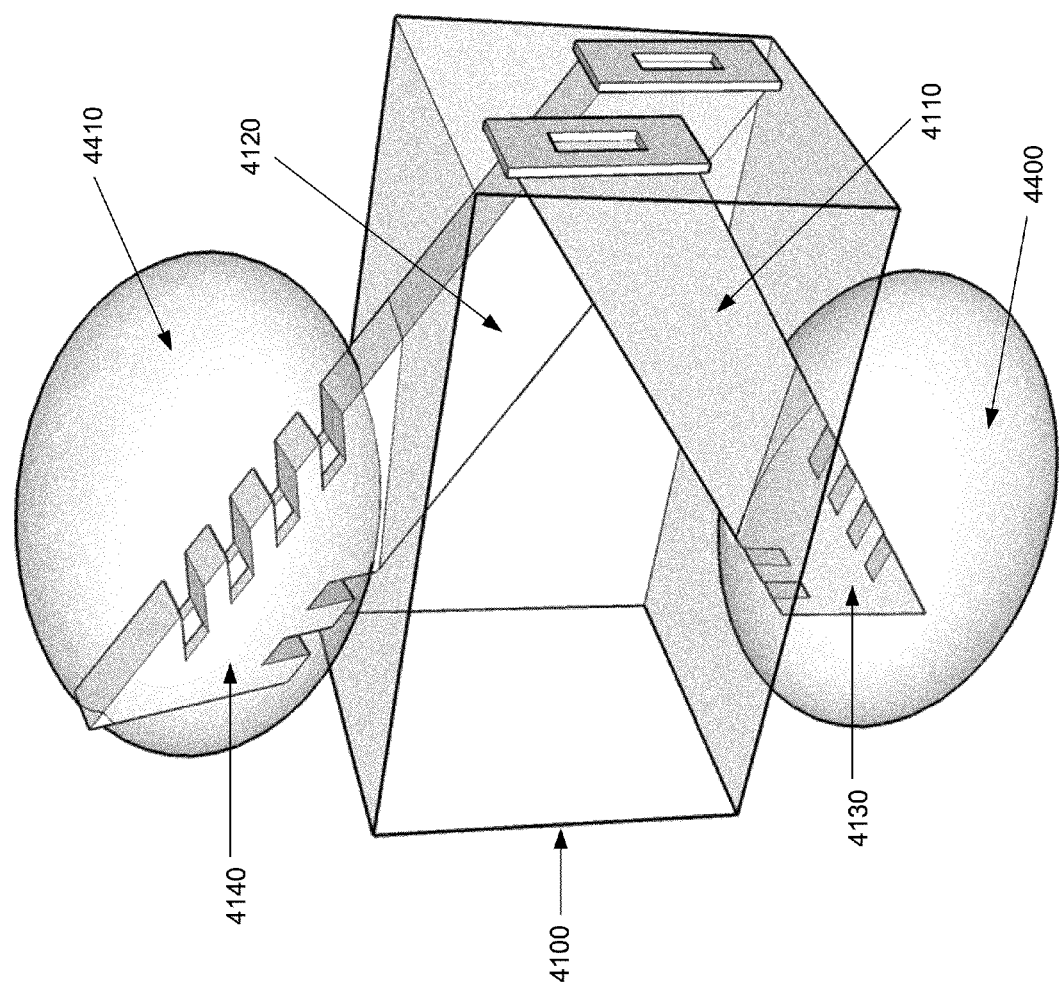

FIGS. 41-42 depict an alternate embodiment of a fusion member that includes straight uncurled channels 4120. These channels traverse cross-sectional planes that are non-parallel with any surface of the fusion member, and additionally, traverse cross-sectional planes that are non-parallel with each other. The distal openings of these oblique, nonparallel channels 4120 are located at or near the geometric centers of the inferior and superior faces of the fusion member. As shown in these figures, the fusion member 4110 includes two channels 4120 that are traversed by anchoring members 4130 and 4140, which are rectangular in cross-sectional profile to match the cross-sectional profile of the channels. FIG. 43 provides a detailed view of the anchoring members depicting the direct communication of the central anchoring member lumen 4300 with perforations 4310 along the anchoring member shaft as well as the "teeth" or retention ridges 4320 and a beveled tip 4330. In FIGS. 44-45, polymer has been injected and forms "clouds" 4400 and 4410 contiguous with the perforated, contoured tips of anchoring members 4130 and 4140 within the marrow spaces of adjacent vertebral bodies (not pictured).

Figure 46A:
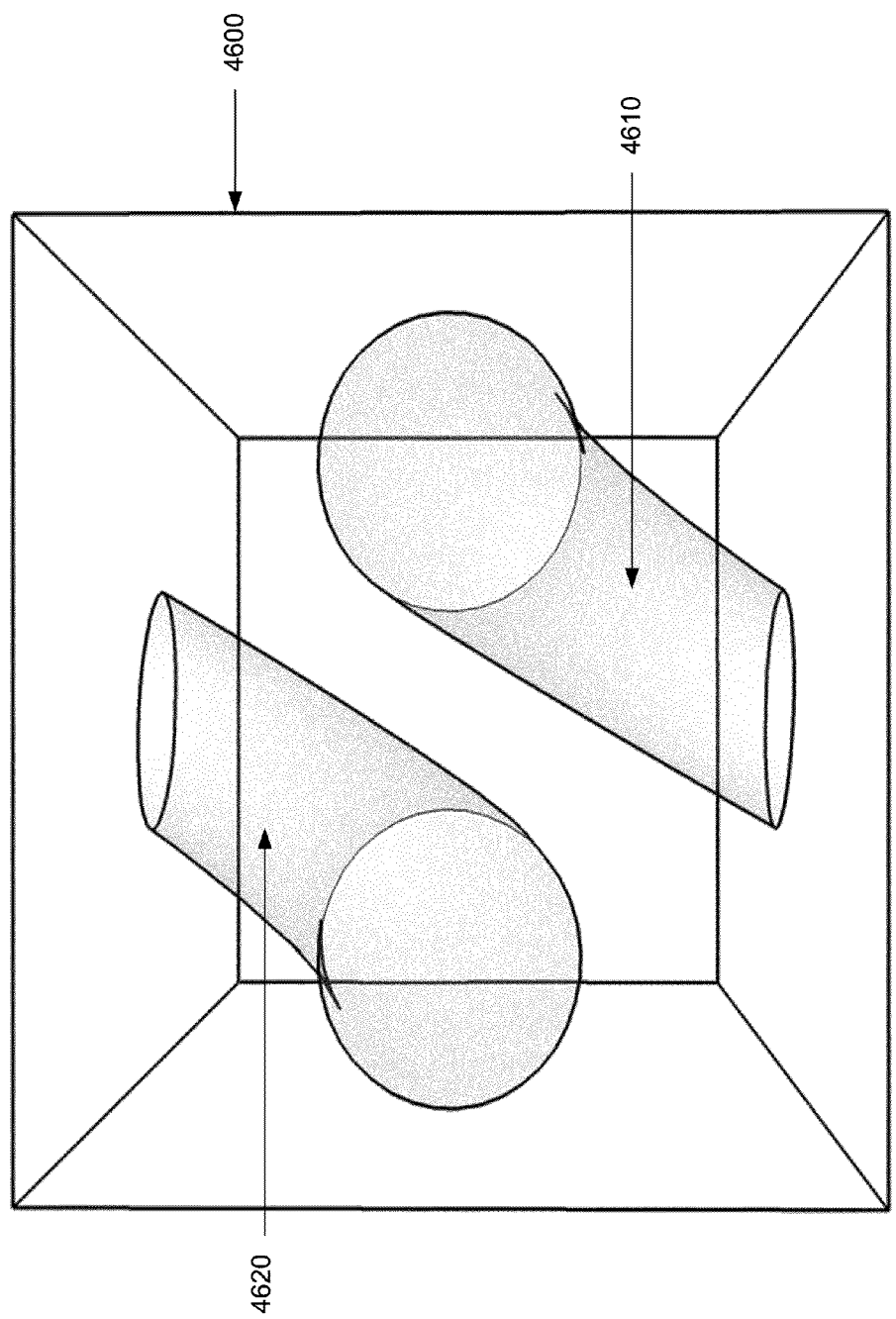
Figure 47:
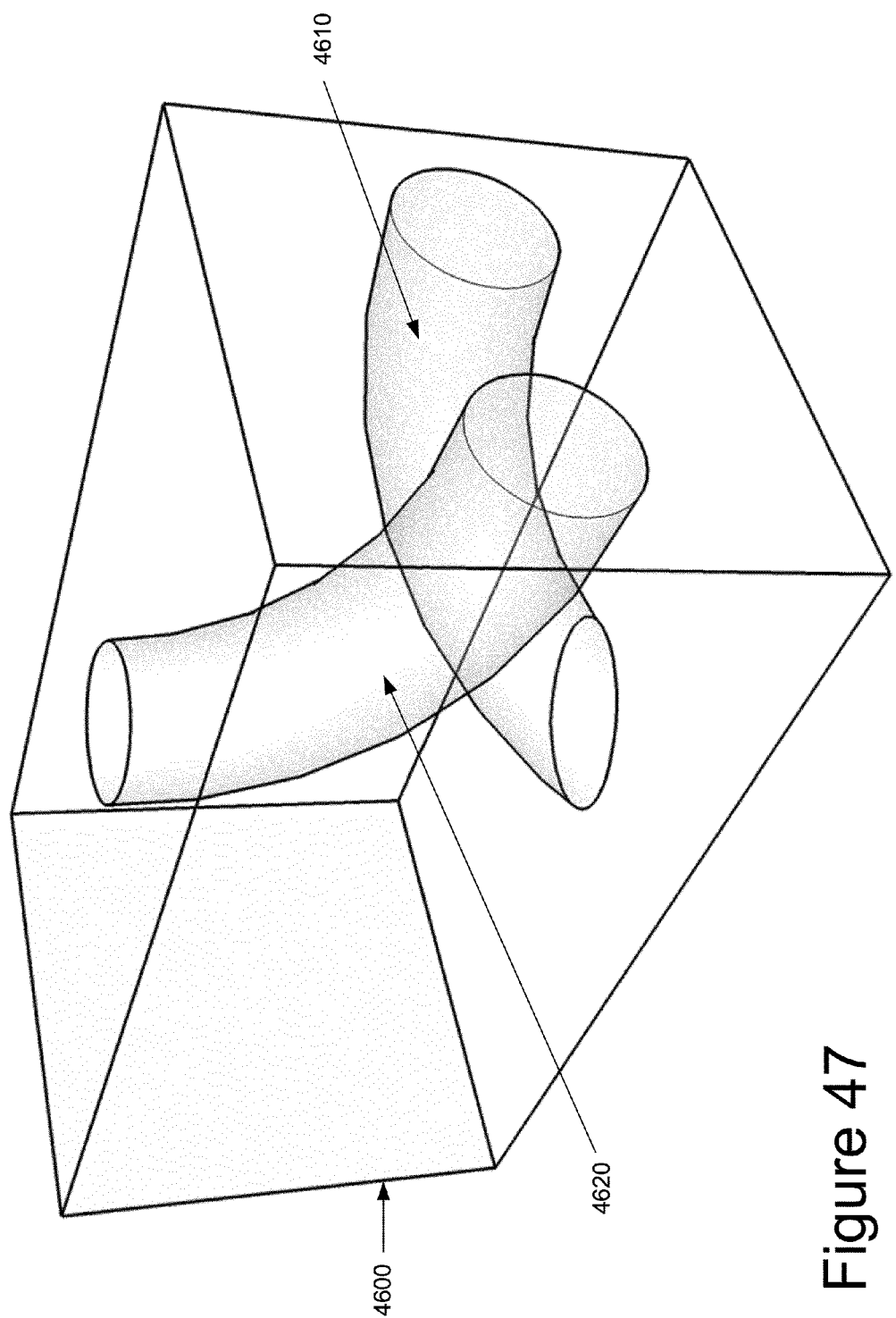

FIGS. 46A, 46B, and 47 depict an alternate embodiment of the fusion member. Specifically, these figures depict a fusion member 4600, which is similar to the fusion member 120 of FIG. 4. Channels 4610 and 4620 traverse in parallel cross-sectional planes with respect to each other but are non-parallel with respect to the faces of the fusion member. FIG. 46B illustrates that each of the channels 4610 and 4620 trace circular arcs that are a portion of two conceptual circles which traverse planes that are parallel to each other and non-parallel to all faces of the fusion member. These channels are traversed by curved anchoring members (not pictured). Although this embodiment provides for channels and anchoring members that trace the arcs of conceptual circles, other embodiments provide for alternative curved conceptual shapes (e.g. ellipses, parabolas, etc.). The distal openings of the channels 4610 and 4620 may be located at or near the geometric centers of the inferior and superior faces of the fusion member.

C. Alternative Anchoring Member Tips and Structures

Figure 48B:
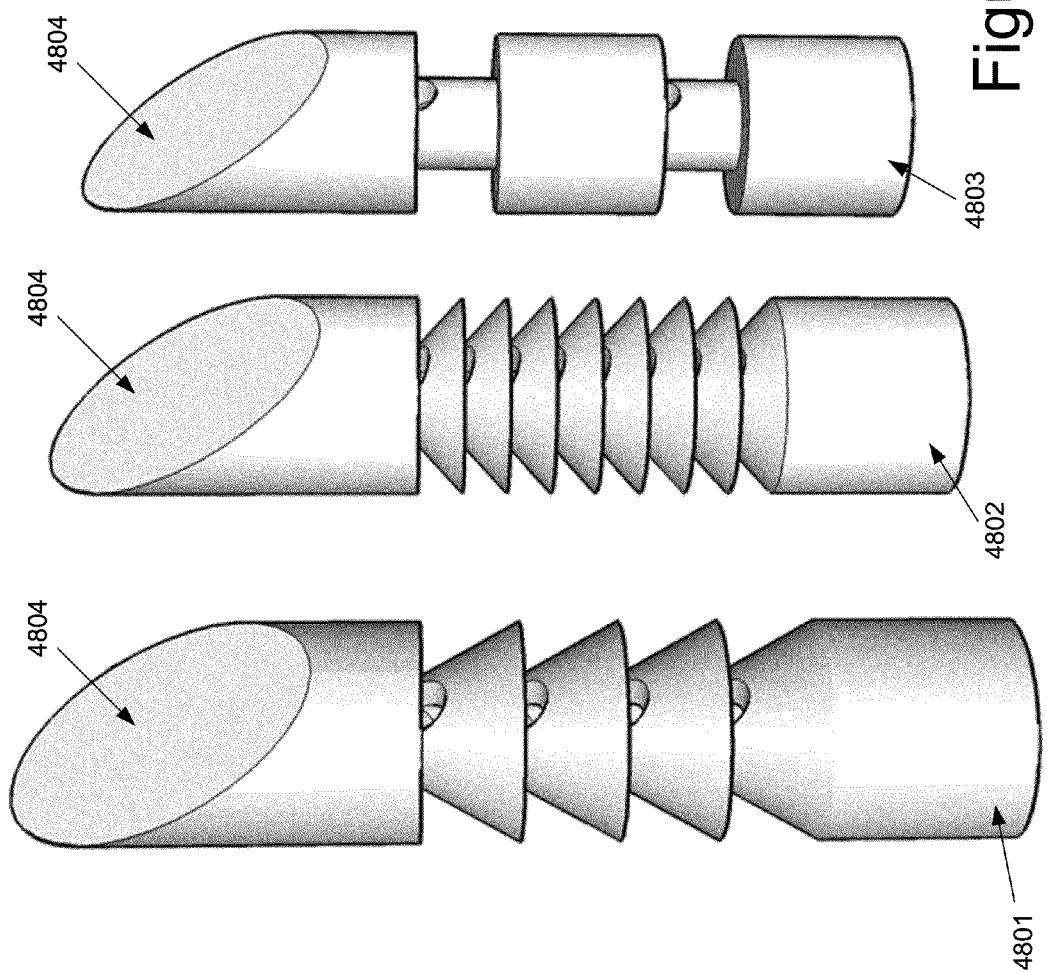

As shown above, different embodiments use different shapes for the anchoring members (e.g., arc-shape, angled-shape, semi-circular shape, straight, etc.). Different embodiments also use different types of anchoring members. FIGS. 48A-48B provide a detailed view of alternative embodiments 4801, 4802, and 4803 of anchoring member tips. As shown in the figures, the central lumen 4800-4810 of the anchoring members are in direct communication with perforations 4815, 4820, and 4825 along the anchoring member shaft as well as the "teeth", or retention ridges, 4830, 4835, and 4840. FIG. 48B illustrates that in some embodiments, the anchoring members have beveled tips 4804.

In some embodiments, the maximum diameter or circumference of the segment of the anchoring member that includes retention ridges or other surface features intended to engage the polymer material (e.g., PMMA or bone cement) is less than or equal to the diameter or circumference of proximal and distal anchoring member segments. This allows the anchoring member to be hammered, tapped, or simply pushed into position within the marrow space of the vertebral bodies rather than being screwed into place.

Figure 48C:
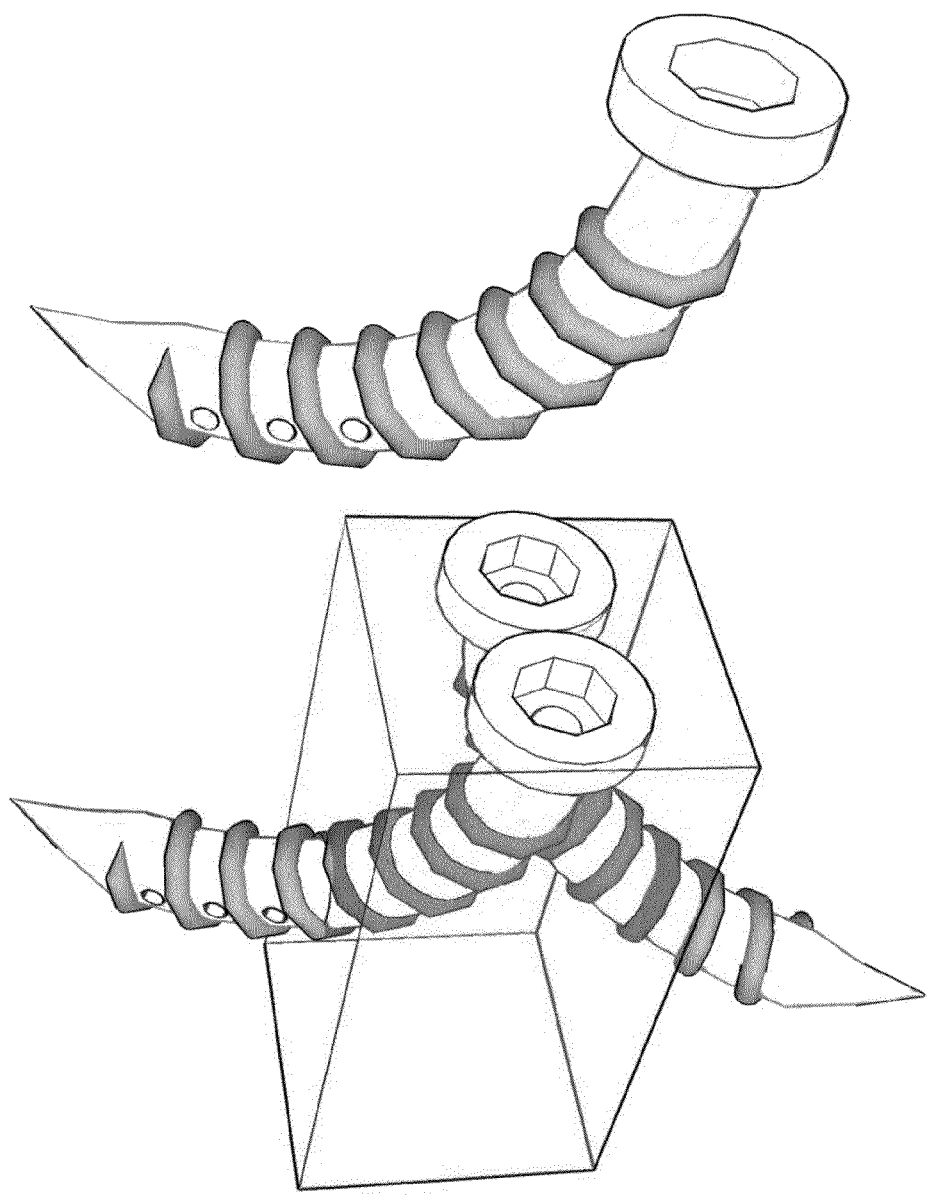
Figure 48D:
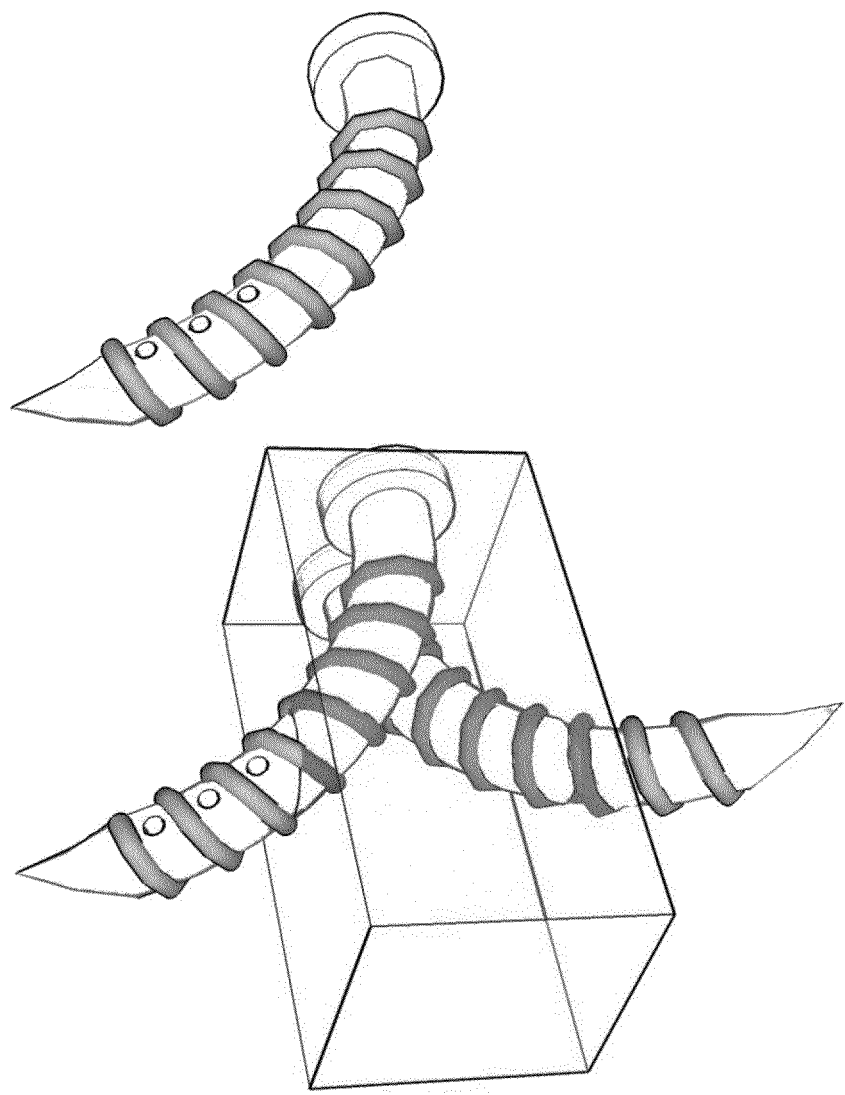

FIGS. 48C-48D illustrate that the anchoring members of some embodiments have threads. As shown, the threads may run the entire length of the anchoring member, from the base of the anchoring member to the tip of the anchoring member. In other embodiments (not shown), the threads run through only a segment of the anchoring member (i.e., less than the entire length of the anchoring member). The threads allow the anchoring members to be screwed into the desired position within the marrow space of the vertebral bodies. In some embodiments, the fusion member channels into which the anchoring members are advanced include grooves that compliment the threads of the anchoring members.

D. Fusion Members with Ridges and Additional Bone-Grafting Channels

Figure 49:
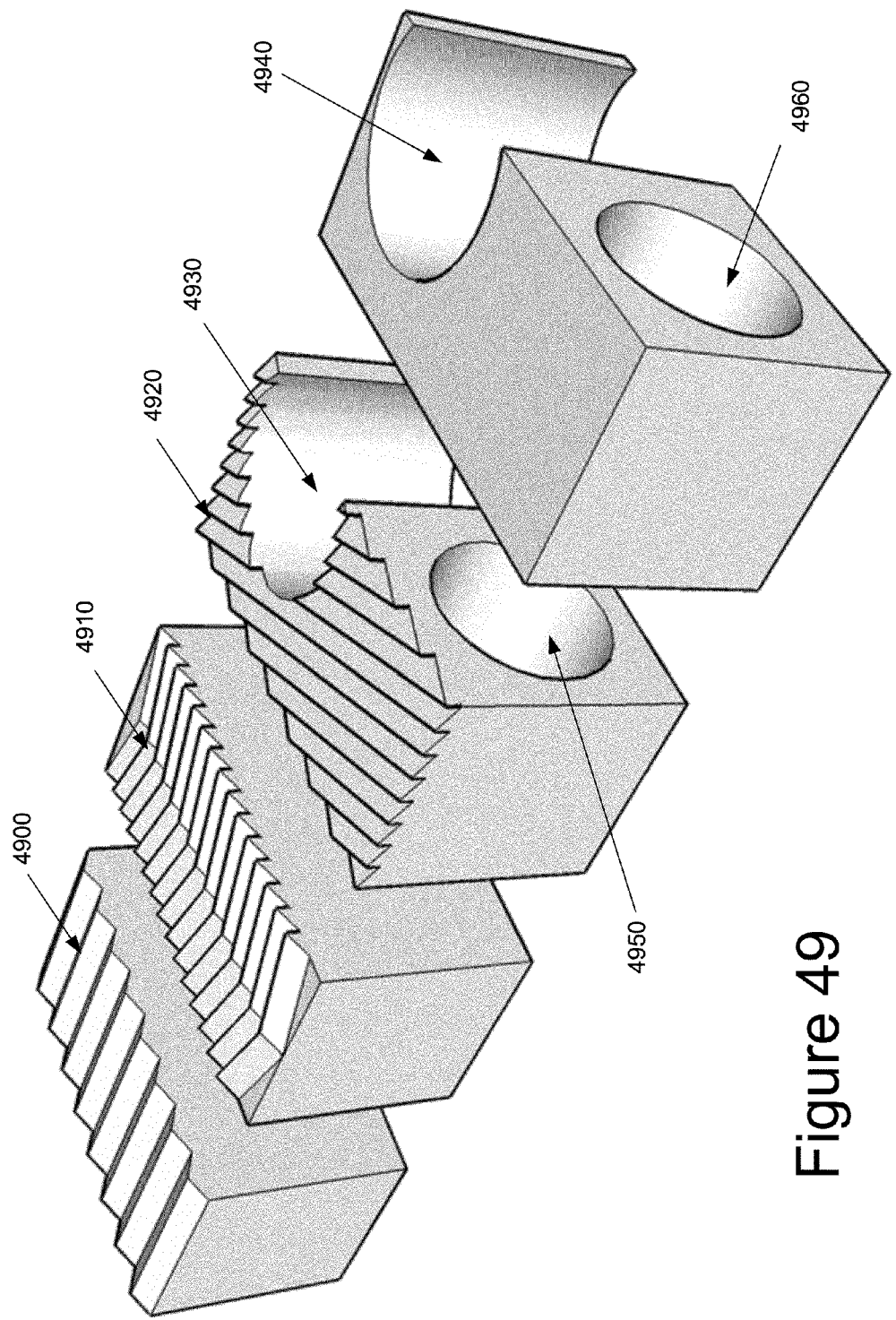
FIG. 49 illustrates various surface contours of the fusion member.

FIG. 49 depicts various fusion member surface contour features including orthogonal ridges 4900, angled ridges 4910, and oblique parallel ridges 4920. Longitudinal channels 4930 and 4940 and transverse channels 4950 and 4960 for positioning and retention of bone graft material are also illustrated. These surface contours and retention channels may be combined with any of the fusion member channel configurations previously described. Bone grafting channels may be of any size and position and allow for the positioning of bone grafting material between and in contact with the opposed endplates of the adjacent vertebral bodies as well as extending from one lateral face to another lateral face of the fusion member. Placement of the bone graft material in the disc space surrounding the fusion member permits the progressive solid bony fusion between the fusion member and the adjacent vertebral bodies.

E. Retention Teeth and Retention Grooves of Variable Dimensions

Figure 50:
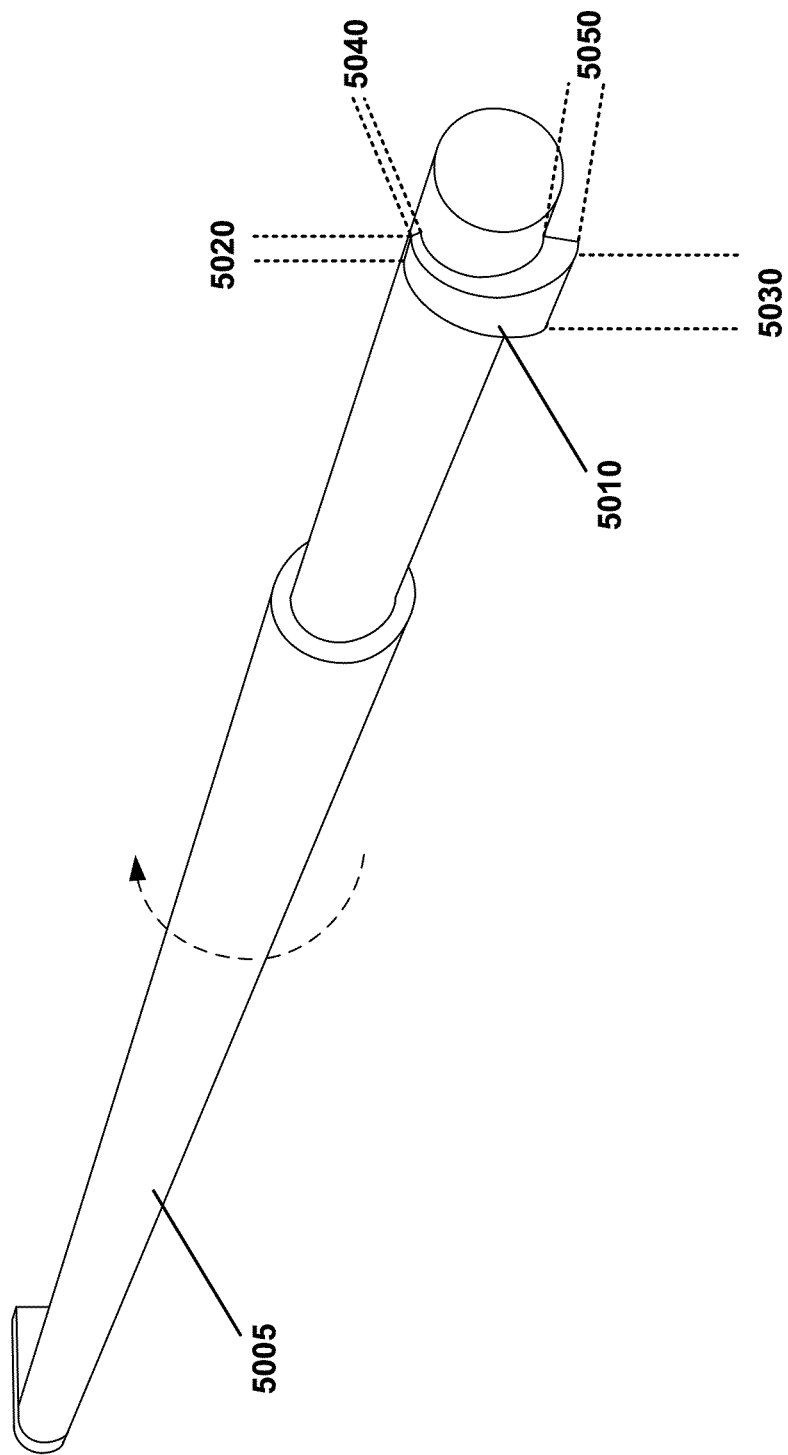
FIG. 50 illustrates an alternative retention rod with retention teeth of variable dimensions.
Figure 51:
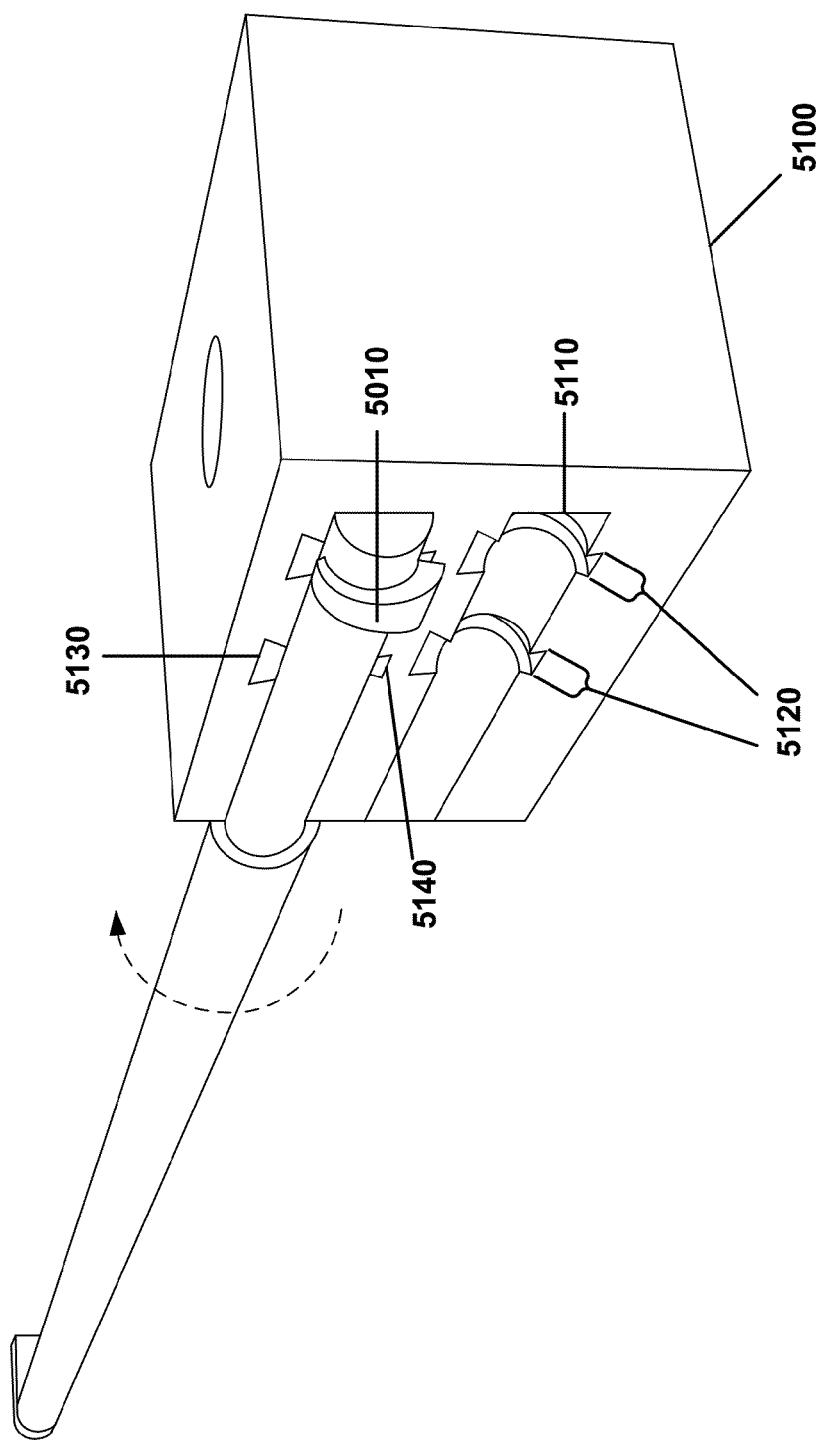
FIG. 51 illustrates an alternative retention rod with retention teeth of variable dimensions engaging retention grooves of matching profile in a fusion member.

In some embodiments, retention teeth and retention grooves are of variable width and height. FIGS. 50 and 51 illustrate a retention rod 5005 with retention teeth (only one tooth 5010 is shown) that engage with a set of larger diameter retention grooves 5120 of a retention groove set 5110 of a fusion member 5100. In FIG. 50, the retention tooth 5010 includes a directional decrease in tooth height and a directional decrease in tooth width when traversing the contour of the tooth in the indicated direction of rotation. The width 5020 of the retention tooth's leading edge is less than the width 5030 of the retention tooth's trailing edge. The height 5040 of the retention tooth's leading edge is less than the height 5050 of the retention tooth's trailing edge. The retention tooth tapers in two directions. Specifically the retention tooth (1) tapers in the radial direction (i.e. height), and (2) tapers in the lateral direction (i.e. width) when traversing the circumference of the tooth.

In FIG. 51, the set of larger diameter retention grooves 5120 of the retention groove set 5110 also decreases in height and width when traversing the contour of the groove in the indicated direction of engagement to match the profile of the retention tooth 5010. Specifically, the retention tooth 5010 is inserted first into opening 5130, which exhibits greater height and width compared to opening 5140. When the tooth's leading edge with smaller dimensions is fully engaged with the opening 5140 with smaller dimensions and the tooth's trailing edge with larger dimensions is fully engaged with the opening 5130 with larger dimensions, the retention rod can no longer be rotated. The tooth's flared shape and matching flared profile of the larger-diameter retention grooves 5120 of the retention groove set 5110 prevent the retention rod from being withdrawn laterally from the fusion member 5100. When decoupling the retention rod from the fusion member 5100, the retention tooth's trailing edge with smaller dimensions is the last to clear the larger diameter retention grooves, facilitating clearance and removal of the retention rod.

F. Various Configurations of Fusion Members and Anchoring Members

Figure 52:
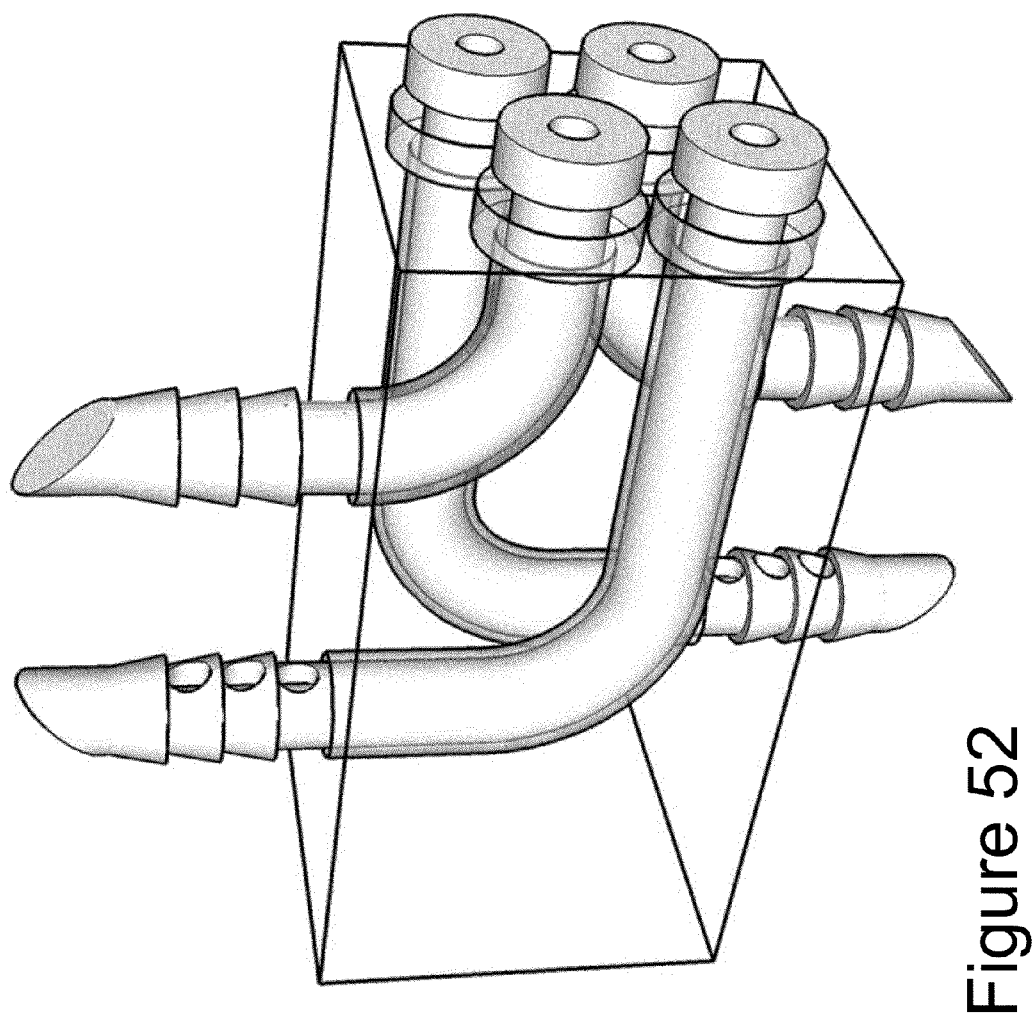
FIG. 52 shows a fusion member with four channels and four anchoring members that are advanced into these fusion member channels.

As mentioned above, some embodiments of the invention provide a fusion member with four channels and four anchoring members that are advanced into these fusion member channels as shown in FIG. 52.

Figure 53:
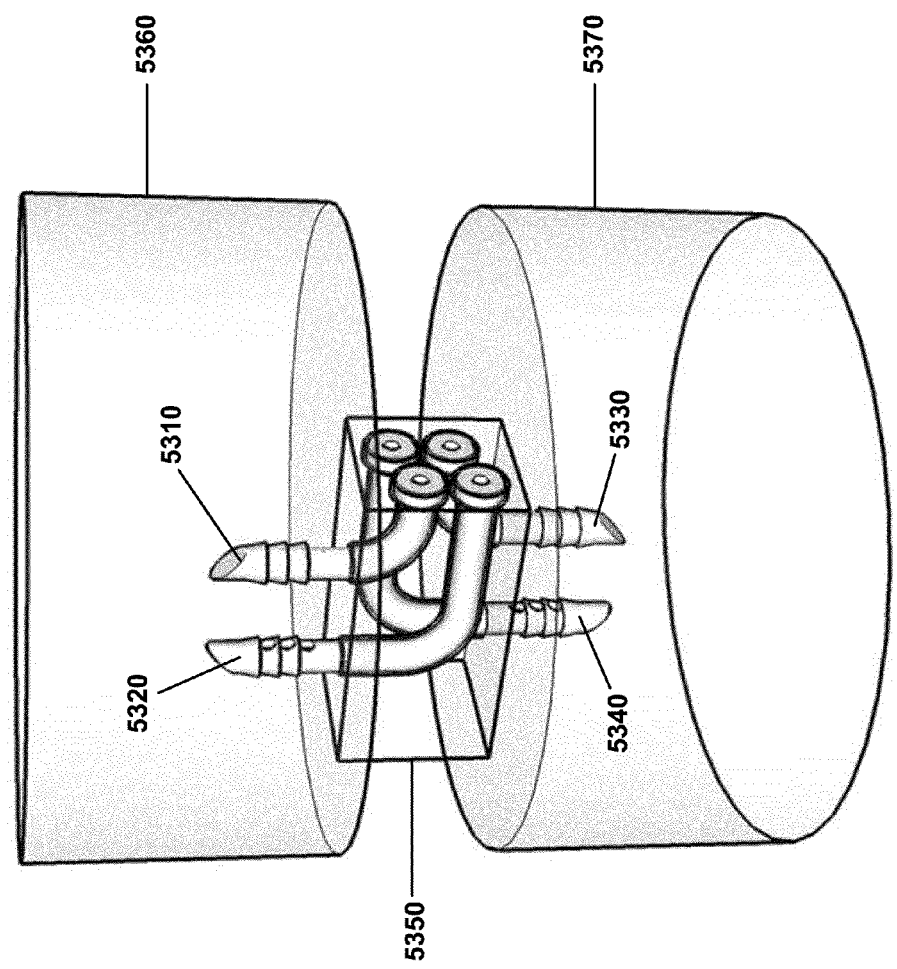
FIG. 53 shows four anchoring members that have been inserted through the fusion member and into the vertebral bodies.
Figure 54:
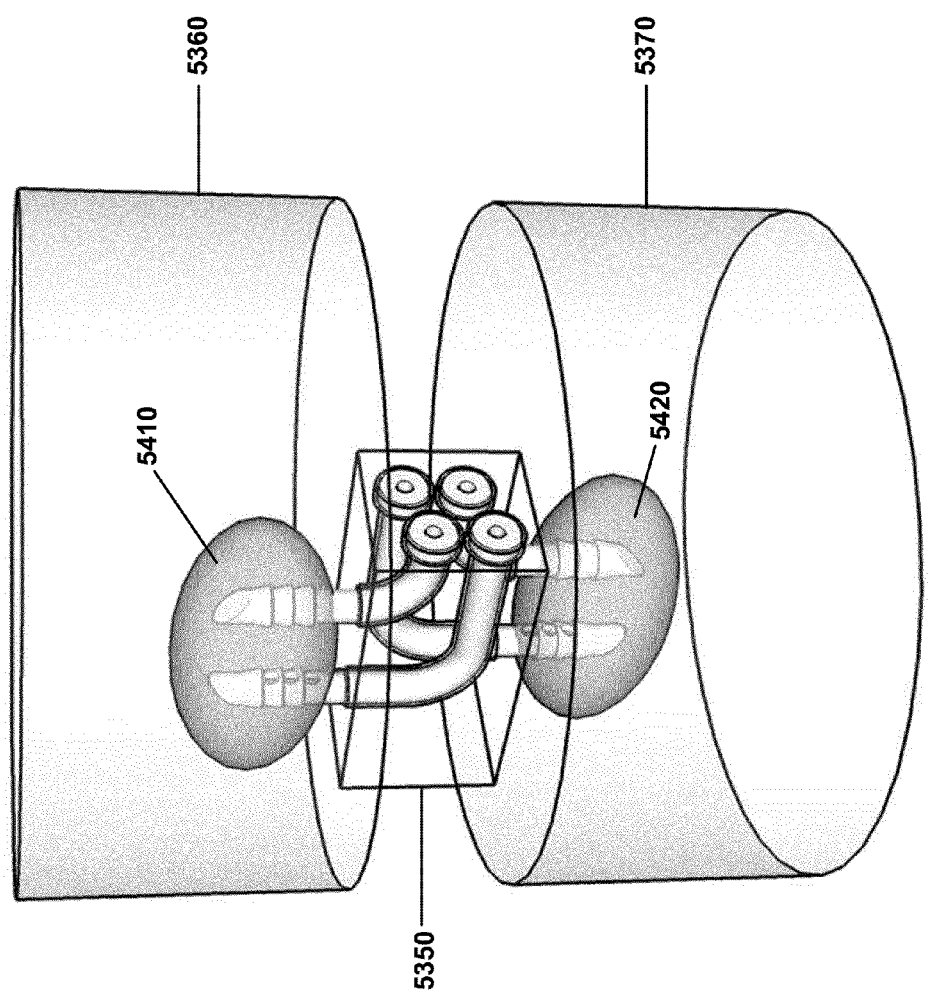
FIG. 54 depicts the placement of one fusion member between adjacent vertebral bodies, a set of four anchoring members that have affixed the fusion member to the vertebral bodies, and the coalescence of the polymer collections that resulted following injections of the polymers via anchoring members.
Figure 55:
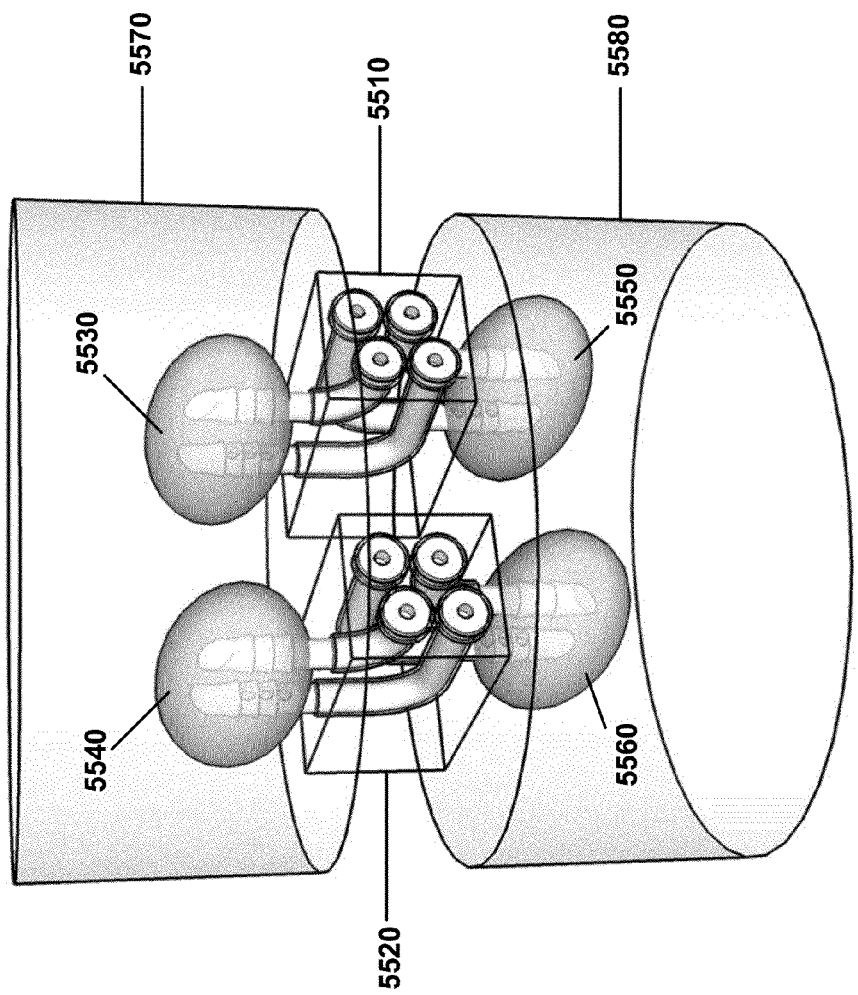
FIG. 55 depicts placement of two fusion members within the right and left paramedian disc space of adjacent vertebral bodies, multiple sets of anchoring members that have affixed the two fusion members to the vertebral bodies, and the coalescence of polymer clouds following the polymer injections.

FIGS. 53-55 illustrate an example of the injection of PMMA, or other bone cement or hardening polymer, through the anchoring members and into the vertebral bodies. In this example, four anchoring members are inserted into the four channels of a fusion block. One of ordinary skill will realize that the same operations can be performed for the embodiments that use two anchoring members through a fusion block with two channels.

In FIG. 53, anchoring members 5310-5340 are fully advanced through the fusion member channels and into the marrow space of adjacent vertebral bodies 5360-5370 immediately above and below the fusion member 5350. Polymer can be injected through the central lumen of the anchoring members and out of the perforations of the anchoring members into the immediate surrounding area within the marrow space of the penetrated vertebrae. FIG. 54 depicts the coalescence of the polymer collections 5410-5420 that result following injections of these polymers via anchoring members 5310-5340, respectively. The coalescence 5410-5420 of these polymers forms a spherical or ellipsoidal "cloud" contiguous with the tip of the anchoring members 5310-5340. The polymer hardens within the marrow space, resulting in a structural union between anchoring members 5310-5340 in addition to anchoring each vertebral body 5360-5370 to the fusion member 5350. The contoured tips of the anchoring members in conjunction with the hardened polymer prevent withdrawal of the anchoring members 5310-5340 from the trabecular bone and enhances the structural integrity of the fusion member 5350. The final result is an intervertebral fusion member 5350 anchored via multiple anchoring members 5310-5340 to collections of hardened polymer (e.g., PMMA or other bone cement) and to the trabecular bone of adjacent vertebral bodies 5360-5370 yielding solid mechanical fusion. Once the anchoring members 5310-5340 are in place, and the polymer has been injected into the marrow space of the vertebral bodies, the driving members may be disengaged from the anchoring members and removed from the patient.

Some embodiments insert more than one fusion member between a pair of adjacent vertebral bodies. One such example is illustrated in FIG. 55. This figure depicts placement of two fusion members 5510-5520 within the right and left paramedian disc space of vertebral bodies 5570-5580, multiple sets of anchoring members advanced into the vertebral bodies 5570-5580, and coalescence of polymer "clouds" 5530-5560 following the polymer injections. The resultant polymer clouds from adjacent tips of anchoring members may unite to form a single larger cloud upon polymerization. The united cloud along with multiple contoured and perforated anchoring members locks the fusion members 5510-5520 to the trabecular bone of vertebral bodies 5570-5580.

VI. Embodiments That do not Use Polymer Materials

While the invention has been described with reference to numerous specific details, one of ordinary skill in the art will recognize that the invention can be embodied in other specific forms without departing from the spirit of the invention. In some embodiments, the anchoring members may be without a central lumen or perforations along their shaft. In some embodiments, angled teeth, back-facing ridges, and other surface retention ridges may be greater in circumference or diameter than the more proximal or distal anchoring member segments. In these instances, after the anchoring members are advanced into the marrow space of the vertebral bodies, injection of polymer materials may not be needed to anchor the vertebral bodies to the fusion member. The surface contours of the anchoring members will anchor the vertebral bodies to the fusion member.

Also, in several of the above-described embodiments, the channels and anchoring members have circular-arc cross-sectional profiles. However, in other embodiments, the channels and anchoring members have alternative curved arc shapes.

I claim:

1. A method for attaching a fusion device, the method comprising:
   positioning a fusion member between two vertebral bodies, the fusion member having at least one channel;
   affixing the fusion member to one of the vertebral bodies using a needle, the needle comprising (i) an embedding member having a first mating member and (ii) a retractable member having a second mating member, the affixing comprising:
     coupling the embedding member with the retractable member in order to form a unified needle by rotating, in a first direction, the retractable member with respect to the embedding member such that the first and second mating members interlock together;
     applying force on the retractable member in order to push the embedding member through the channel of the fusion member into the vertebral body; and
     anchoring the embedding member within the vertebral body and to the fusion member;

decoupling the retractable member from the embedding member by rotating the retractable member in a second direction that is opposite to the first direction; and retracting the retractable member.

2. The method of claim 1, wherein the embedding member is partially within the fusion member when the embedding member anchors within the vertebral body, wherein the retractable member and the embedding member both have hollow interiors for receiving hardening material.

3. The method of claim 2, wherein anchoring the embedding member within the vertebral body comprises depositing the hardening material within the vertebral body at a location about which the embedding member anchors within the vertebral body.

4. The method of claim 1, wherein applying force on the retractable member comprises pushing the retractable member without rotating the retractable member about the embedding member's longitudinal axis.

5. The method of claim 1, wherein applying force on the retractable member further comprises tapping one end of the retractable member.

6. The method of claim 1, wherein applying force on the retractable member comprises pushing the retractable member towards the embedding member in order to push the embedding member into the vertebral body.

7. The method of claim 1, wherein positioning the fusion member between the vertebral bodies further comprises coupling the fusion member to a retention rod.

8. The method of claim 1, wherein anchoring the embedding member to the fusion member further comprises fitting a flanged end of the embedding member into a cavity of the fusion member.

9. The method of claim 1, wherein both the first and second mating members comprise an arm and a slot.

10. The method of claim 1 further comprising driving a smaller gauge guiding member through the channel of the fusion member to create a guide in the vertebral body, wherein pushing the embedding member through the channel comprises driving the embedding member into the created guide in the vertebral body.

11. The method of claim 1, wherein decoupling the retractable member is done using robotic arms.

12. The method of claim 1 further comprising affixing the fusion member to the other vertebral body.

13. A needle for affixing a fusion member to a vertebral body, said needle comprising:
    an embedding member configured to penetrate and anchor within the vertebral body in a patient, wherein the embedding member comprises a first mating member; and
    a retractable member comprising a second mating member, the retractable member configured to (i) couple to the embedding member by rotating the retractable member in a first direction with respect to the embedding member such that the first and second mating members interlock together, (ii) drive the embedding member into the vertebral body through the fusion member, (iii) decouple from the embedding member by rotating the retractable member in a second direction that is opposite to the first direction, and (iv) retract from the patient while leaving the embedding member embedded in the vertebral body,
    wherein when the embedding member and retractable member couple to each other, said members form a single unified needle.

14. The needle of claim 13, wherein both the first mating member and the second mating member comprise an arm and a slot.

15. The needle of claim 13, wherein when the embedding member and retractable member are coupled, the retractable member is engaged to tap the embedding member into the vertebral body.

16. The needle of claim 13, wherein when the embedding and retractable members are coupled, the retractable member is engaged to push the embedding member into the vertebral body.

17. The needle of claim 13, wherein the embedding member is curved.

18. The needle of claim 13, wherein the embedding member is partially within the fusion member when the embedding member anchors within the vertebral body,
    wherein the retractable and embedding members both have hollow interiors for receiving hardening material for depositing within the vertebral body at a location about which the embedding member anchors within the vertebral body, wherein said deposited hardening material hardens to solidify the anchoring of the embedding member within the fusion member to the vertebral body.

19. The needle of claim 18,
    wherein the retractable and embedding members hingably couple so that as the retractable member pushes the embedding member, the embedding member follows an angular path through the fusion member and into the vertebral body,
    wherein when said embedding member is in a desired position within the vertebral body, said hollow interiors of said members align to form a passageway for directing hardening material through the retractable member's hollow interior and into the embedding member's hollow interior.

20. The needle of claim 13, wherein the retractable and embedding members hingably couple so that as the retractable member pushes the embedding member, the embedding member follows an angular path through the fusion member and into the vertebral body.

* * * * *